(12) United States Patent
Chuprakov et al.

(10) Patent No.: US 12,187,810 B2
(45) Date of Patent: Jan. 7, 2025

(54) GLYCOSIDE DUAL-CLEAVAGE LINKERS FOR ANTIBODY-DRUG CONJUGATES

(71) Applicant: R.P. Scherer Technologies, LLC, Carson City, NV (US)

(72) Inventors: Stepan Chuprakov, Emeryville, CA (US); Ayodele O. Ogunkoya, Berkeley, CA (US)

(73) Assignee: R.P. Scherer Technologies, LLC, Carson City, NV (US)

( * ) Notice: Subject to any disclaimer, the term of this patent is extended or adjusted under 35 U.S.C. 154(b) by 216 days.

(21) Appl. No.: 17/531,343

(22) Filed: Nov. 19, 2021

(65) Prior Publication Data
US 2022/0249686 A1    Aug. 11, 2022

Related U.S. Application Data

(60) Provisional application No. 63/139,685, filed on Jan. 20, 2021, provisional application No. 63/116,632, filed on Nov. 20, 2020.

(51) Int. Cl.
*A61K 47/68* (2017.01)
*A61P 35/00* (2006.01)
*C07K 5/062* (2006.01)

(52) U.S. Cl.
CPC .... *C07K 5/06034* (2013.01); *A61K 47/68031* (2023.08); *A61K 47/68033* (2023.08); *A61K 47/6813* (2017.08); *A61K 47/6817* (2017.08); *A61K 47/6829* (2017.08); *A61K 47/6831* (2017.08); *A61K 47/6889* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 4,935,496 A | 6/1990 | Kudo et al. |
| 5,200,534 A | 4/1993 | Rao |
| 5,202,448 A | 4/1993 | Carver et al. |
| 5,225,539 A | 7/1993 | Winter |

(Continued)

FOREIGN PATENT DOCUMENTS

| | | |
|---|---|---|
| EP | 0239400 | 8/1994 |
| EP | 0590267 | 5/2002 |

(Continued)

OTHER PUBLICATIONS

Lu et al., Int. J. Mol. Sci. 2016, 17, 561 (Year: 2016).*

(Continued)

*Primary Examiner* — Karl J Puttlitz
(74) *Attorney, Agent, or Firm* — Rudy J. Ng; Melissa Nakamoto; Bozicevic, Field & Francis LLP

(57) ABSTRACT

The present disclosure provides antibody-drug conjugate structures, which include a cleavable linker that links the antibody to the drug and has a first enzymatically cleavable moiety and a second enzymatically cleavable moiety which includes a glycoside selected from a galactoside, a glucoside, a mannoside, a fucoside, O-GlcNAc, and O-GalNAc. The disclosure also encompasses compounds and methods for production of such conjugates, as well as methods of using the conjugates.

15 Claims, 20 Drawing Sheets

Specification includes a Sequence Listing.

(56) References Cited

U.S. PATENT DOCUMENTS

| | | | |
|---|---|---|---|
| 5,229,529 | A | 7/1993 | Ueno et al. |
| 5,274,137 | A | 12/1993 | Nicolaou et al. |
| 5,279,949 | A | 1/1994 | Nair |
| 5,283,253 | A | 2/1994 | Holton et al. |
| 5,294,637 | A | 3/1994 | Chen et al. |
| 5,415,869 | A | 5/1995 | Straubiner et al. |
| 5,502,167 | A | 3/1996 | Waldmann et al. |
| 5,530,101 | A | 6/1996 | Queen et al. |
| 5,558,864 | A | 9/1996 | Bendig et al. |
| 5,565,332 | A | 10/1996 | Hoogenboom et al. |
| 5,585,089 | A | 12/1996 | Queen et al. |
| 5,693,493 | A | 12/1997 | Robinson et al. |
| 5,698,417 | A | 12/1997 | Robinson et al. |
| 5,705,154 | A | 1/1998 | Dalie et al. |
| 5,750,078 | A | 5/1998 | Shitara et al. |
| 5,770,403 | A | 6/1998 | Dalie et al. |
| 5,821,263 | A | 10/1998 | Scola et al. |
| 5,824,701 | A | 10/1998 | Greenwald et al. |
| 5,869,680 | A | 2/1999 | Mas et al. |
| 6,323,315 | B1 | 11/2001 | Pettit et al. |
| 6,570,040 | B2 | 5/2003 | Saxon et al. |
| 7,985,783 | B2 | 7/2011 | Carrico et al. |
| 8,729,232 | B2 | 5/2014 | Rush et al. |
| 9,310,374 | B2 | 4/2016 | Kudirka et al. |
| 9,493,413 | B2 | 11/2016 | Rabuka et al. |
| 10,973,920 | B2 | 4/2021 | Helin et al. |
| 2004/0086979 | A1 | 5/2004 | Zhang et al. |
| 2005/0033031 | A1 | 2/2005 | Couto |
| 2016/0339117 | A1* | 11/2016 | Ackler ............... A61K 47/6889 |
| 2019/0314509 | A1 | 10/2019 | Kudirka et al. |
| 2020/0323995 | A1 | 10/2020 | Satomaa et al. |
| 2022/0226490 | A1* | 7/2022 | Rabuka ............... A61K 47/6889 |

FOREIGN PATENT DOCUMENTS

| | | |
|---|---|---|
| EP | 1391213 | 2/2004 |
| EP | 0592106 | 11/2004 |
| EP | 0519596 | 2/2005 |
| WO | WO1991009967 | 7/1991 |
| WO | WO1993010076 | 5/1993 |
| WO | WO1993023555 | 11/1993 |
| WO | WO1994007876 | 4/1994 |
| WO | WO1994007880 | 4/1994 |
| WO | WO1994007881 | 4/1994 |
| WO | WO1994007882 | 4/1994 |
| WO | WO1996014856 | 5/1996 |
| WO | WO1996033212 | 10/1996 |
| WO | WO1998013059 | 4/1998 |
| WO | WO1998022451 | 5/1998 |
| WO | WO1998028288 | 7/1998 |
| WO | WO1998045331 | 10/1998 |
| WO | WO1998045332 | 10/1998 |
| WO | WO1998058927 | 12/1998 |
| WO | WO1999009021 | 2/1999 |
| WO | WO1999014209 | 3/1999 |
| WO | WO1999018113 | 4/1999 |
| WO | WO2019118411 | 6/2019 |
| WO | WO2020096775 | 5/2020 |
| WO | 2020154437 * | 7/2020 |
| WO | WO 2022/175595 | 8/2022 |

OTHER PUBLICATIONS https://en.wikipedia.org/wiki/Lysosome downloaded Sep. 14, 2023; citing Kumar P, Mina U (2013). Life Sciences: Fundamentals and practice (3rd ed.). New Delhi: Pathfinder Academy (Year: 2013).*

Padlan, (1991) "A possible procedure for reducing the immunogenicity of antibody variable domains while preserving their ligand-binding properties," Molecular Immunology, vol. 28, Nos. 4 and 5, pp. 489-498.

Studnicka et al., (1994) "Human-engineered monoclonal antibodies retain full specific binding activity by preserving hon-CDR complementarity modulating residues," Protein Engineering, vol. 7, No. 6, pp. 805-814.

Roguska et al., (1994) "Humanization of murine monoclonal antibodies through variable domain resurfacing," PNAS, vol. 91, pp. 969-973.

Riechmann et al., (1988) "Reshaping human antibodies for therapy," Nature, vol. 332, No. 24, pp. 323-327.

Jefferis et al., (2009) "Human immunoglobulin allotypes," mABs, vol. 1, No. 4, pp. 332-338.

Liu et al., (1996) "Eradication of large colon tumor xenografts by targeted delivery of maytansinoids," Proc. Natl. Acad. Sci. USA, vol. 93, pp. 8618-8623.

* cited by examiner

| # | Time | Area | Height | Width | Area% | Symmerty |
|---|------|------|--------|-------|-------|----------|
| 1 | 3.806 | 795.6 | 40.6 | 0.3269 | 6.971 | 0.617 |
| 2 | 5.733 | 2300.4 | 61 | 0.6287 | 20.155 | 0.512 |
| 3 | 7.372 | 8317.1 | 524.7 | 0.2642 | 72.873 | 0.748 |

| # | Time | Area | Height | Width | Area% | Symmerty |
|---|------|------|--------|-------|-------|----------|
| 1 | 6.424 | 358.3 | 8.1 | 0.7355 | 2.354 | 0 |
| 2 | 7.564 | 14860 | 345.8 | 0.7161 | 97.646 | 0.43 |

| # | Time | Type | Area | Height | Width | Area% | Symmerty |
|---|------|------|------|--------|-------|-------|----------|
| 1 | 4.804 | MM | 988.5 | 43.2 | 0.381 | 8.493 | 0.39 |
| 2 | 7.118 | MF | 1474.7 | 43.2 | 0.5685 | 12.670 | 1.385 |
| 3 | 8.174 | FM | 9176.2 | 531.8 | 0.2876 | 78.837 | 0.716 |

| # | Time | Type | Area | Height | Width | Area% | Symmerty |
|---|------|------|------|--------|-------|-------|----------|
| 1 | 6.826 | MF | 476.7 | 13.2 | 0.6022 | 4.111 | 0 |
| 2 | 8.049 | FM | 11120.6 | 350.7 | 0.5285 | 95.889 | 0.564 |

| # | Time | Type | Area | Height | Width | Area% | Symmerty |
|---|------|------|------|--------|-------|-------|----------|
| 1 | 4.989 | MM | 441.4 | 17.8 | 0.4125 | 5.278 | 0.532 |
| 2 | 7.245 | MF | 849.6 | 26.6 | 0.5321 | 10.159 | 1.814 |
| 3 | 8.167 | FM | 7071.9 | 453.2 | 0.2601 | 84.562 | 0.623 |

| # | Time | Type | Area | Height | Width | Area% | Symmerty |
|---|------|------|------|--------|-------|-------|----------|
| 1 | 6.808 | MF | 452.5 | 10.3 | 0.7353 | 3.854 | 0 |
| 2 | 8.14 | FM | 11289 | 347.2 | 0.542 | 96.146 | 0.56 |

SEQUENCE LISTING

```
<160> NUMBER OF SEQ ID NOS: 23

<210> SEQ ID NO 1
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 1

Leu Cys Thr Pro Ser Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 2

Met Cys Thr Pro Ser Arg
1               5

<210> SEQ ID NO 3
<211> LENGTH: 6
<212> TYPE: PRT
```

```
<213> ORGANISM: Artificial Sequence
<220> FEATURE:
<223> OTHER INFORMATION: Synthetic Sequence

<400> SEQUENCE: 3

Val Cys Thr Pro Ser Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 4

Leu Cys Ser Pro Ser Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 5

Leu Cys Ala Pro Ser Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 6

Leu Cys Val Pro Ser Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 7

Leu Cys Gly Pro Ser Arg
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 8

Ile Cys Thr Pro Ala Arg
1               5

<210> SEQ ID NO 9
<211> LENGTH: 6
<212> TYPE: PRT
<213> ORGANISM: Artificial Sequence
```

```
<220> FEATURE:
<223> OTHER INFORMATION: Synthetic Sequence

<400> SEQUENCE: 9

Leu Cys Thr Pro Ser Lys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 10

Met Cys Thr Pro Ser Lys
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 11

Val Cys Thr Pro Ser Lys
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 12

Leu Cys Ser Pro Ser Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 13

Leu Cys Ala Pro Ser Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 14

Leu Cys Val Pro Ser Lys
1               5

<210> SEQ ID NO 15
<211> LENGTH: 6
<212> TYPE: PRT
<213> ORGANISM: Artificial Sequence
<220> FEATURE:
```

```
<223> OTHER INFORMATION: Synthetic Sequence

<400> SEQUENCE: 15

Leu Cys Gly Pro Ser Lys
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 16

Leu Cys Thr Pro Ser Ala
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 17

Ile Cys Thr Pro Ala Ala
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 18

Met Cys Thr Pro Ser Ala
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 19

Val Cys Thr Pro Ser Ala
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 20

Leu Cys Ser Pro Ser Ala
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Sequence
```

```
<400> SEQUENCE: 21

Leu Cys Ala Pro Ser Ala
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 22

Leu Cys Val Pro Ser Ala
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 23

Leu Cys Gly Pro Ser Ala
1               5
```

GLYCOSIDE DUAL-CLEAVAGE LINKERS FOR ANTIBODY-DRUG CONJUGATES

CROSS-REFERENCE TO RELATED APPLICATIONS

This application claims the benefit of U.S. Provisional Application No. 63/116,632, filed Nov. 20, 2020, and U.S. Provisional Application No. 63/139,685, filed Jan. 20, 2021, the disclosures of which are incorporated herein by reference.

INTRODUCTION

The field of protein-small molecule therapeutic conjugates has advanced greatly, providing a number of clinically beneficial drugs with the promise of providing more in the years to come. Protein-conjugate therapeutics can provide several advantages, due to, for example, specificity, multiplicity of functions and relatively low off-target activity, resulting in fewer side effects. Chemical modification of proteins may extend these advantages by rendering them more potent, stable, or multimodal.

SUMMARY

The present disclosure provides antibody-drug conjugate structures, which include a cleavable linker that links the antibody to the drug and has a first enzymatically cleavable moiety and a second enzymatically cleavable moiety which includes a glycoside selected from a galactoside, a glucoside, a mannoside, a fucoside, O-GlcNAc, and O-GalNAc. The disclosure also encompasses compounds and methods for production of such conjugates, as well as methods of using the conjugates.

Aspects of the present disclosure include a conjugate that includes an antibody, a drug, and cleavable linker that links the antibody to the drug and has a first enzymatically cleavable moiety and a second enzymatically cleavable moiety which includes a glycoside selected from a galactoside, a glucoside, a mannoside, a fucoside, O-GlcNAc, and O-GalNAc.

In some embodiments, the conjugate is of formula (I):

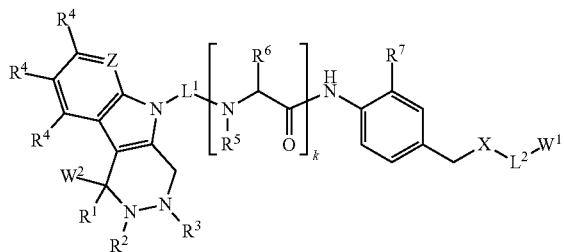

(I)

wherein

Z is $CR^4$ or N;

X is O or $NR^4$;

$R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;

each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

each $R^5$ is independently selected from hydrogen, alkyl, substituted alkyl, alkenyl, substituted alkenyl, alkynyl, and substituted alkynyl;

each $R^6$ is independently selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

k is an integer from 1 to 10;

$R^7$ comprises the second enzymatically cleavable moiety;

$L^1$ is a first linker;

$L^2$ is a second linker;

$W^1$ is the drug; and $W^2$ is the antibody.

In some embodiments, k is 2; and the conjugate is of formula (Ia):

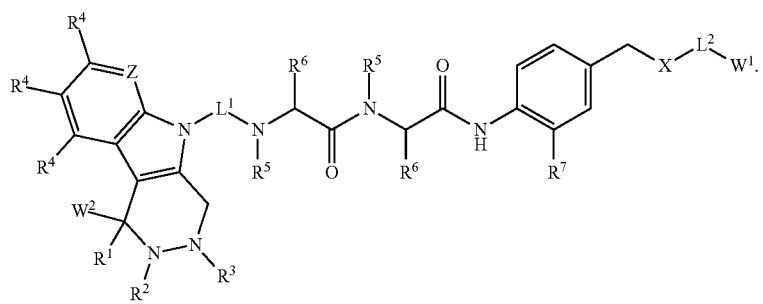

(Ia)

In some embodiments, the second enzymatically cleavable moiety comprises a galactoside. In some embodiments, the second enzymatically cleavable moiety comprises a glucoside. In some embodiments, the second enzymatically cleavable moiety comprises a mannoside. In some embodiments, the second enzymatically cleavable moiety comprises a fucisode. In some embodiments, the second enzymatically cleavable moiety comprises O-GlcNAc. In some embodiments, the second enzymatically cleavable moiety comprises O-GalNAc.

In some embodiments, the conjugate is of formula (Ib):

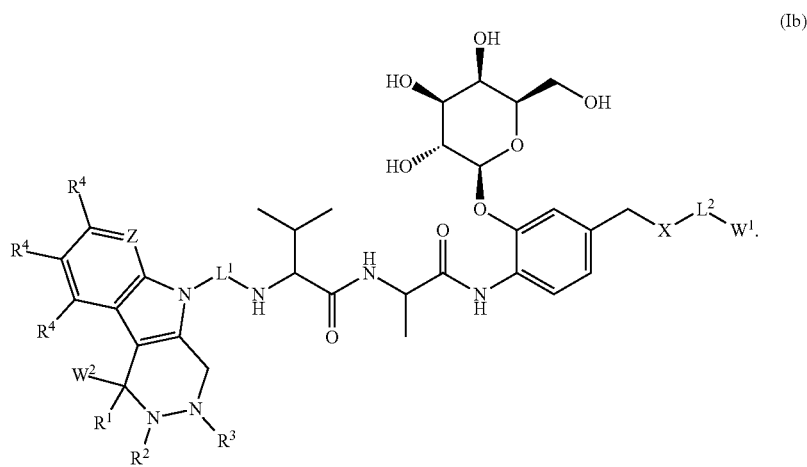

(Ib)

In some embodiments, the conjugate is of formula (Ic):

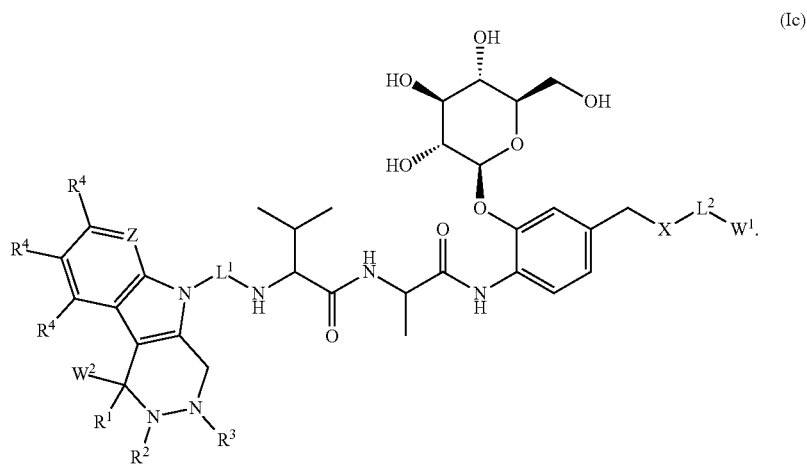

(Ic)

In some embodiments, the conjugate is of formula (Id):
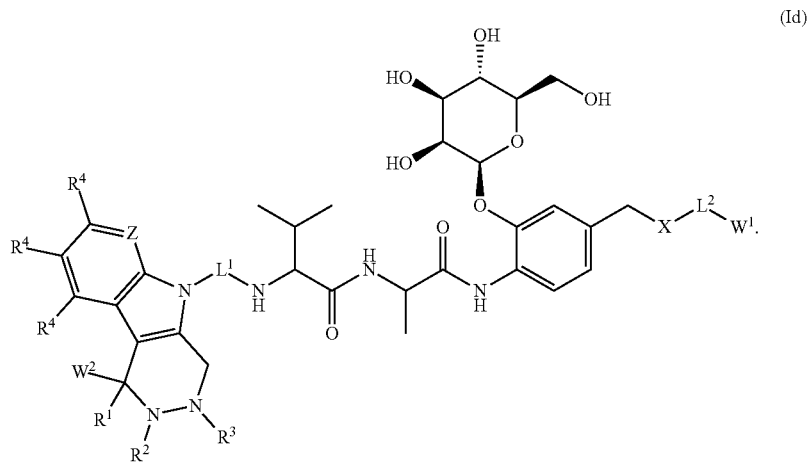
(Id)
In some embodiments, the conjugate is of formula (Ie):
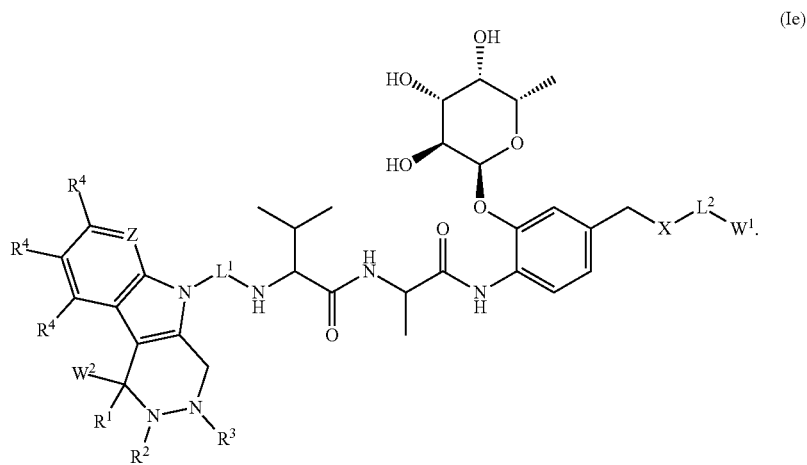
(Ie)
In some embodiments, the conjugate is of formula (If):
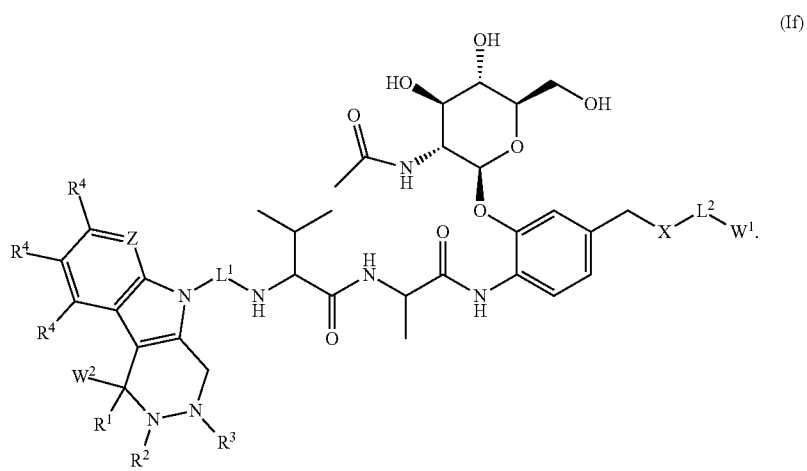
(If)

In some embodiments, the conjugate is of formula (Ig):

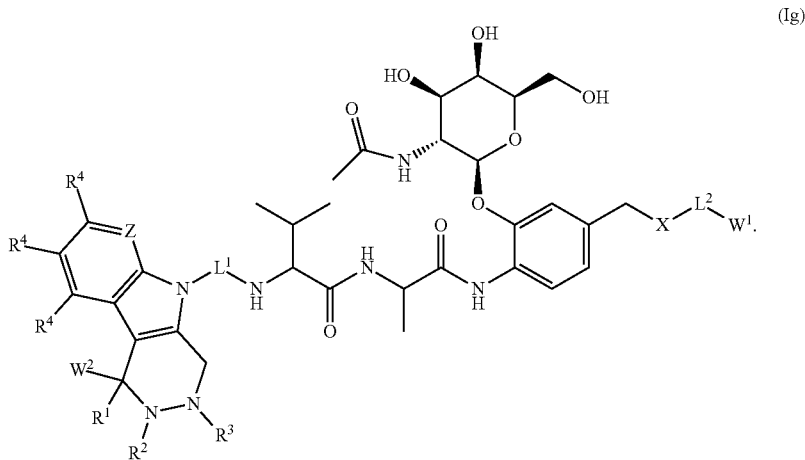

In some embodiments, $L^1$ comprises:

$-(T^1-V^1)_a-(T^2-V^2)_b-(T^3-V^3)_c-(T^4-V^4)_d-,$ wherein
- a, b, c and d are each independently 0 or 1;
- $T^1$, $T^2$, $T^3$ and $T^4$ are each independently selected from a covalent bond, $(C_1-C_{12})$alkyl, substituted $(C_1-C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, $-(CR^{13}OH)_m-$, 4-amino-piperidine (4AP), an acetal group, a hydrazine, a disulfide, and an ester, wherein EDA is an ethylene diamine moiety, PEG is a polyethylene glycol, and AA is an amino acid residue or an amino acid analog, wherein each w is an integer from 1 to 20, each n is an integer from 1 to 30, each p is an integer from 1 to 20, and each m is an integer from 1 to 12;
- $V^1$, $V^2$, $V^3$ and $V^4$ are each independently selected from the group consisting of a covalent bond, $-CO-$, $-NR^{15}-$, $-NR^{15}(CH_2)_q-$, $-NR^{15}(C_6H_4)-$, $-CONR^{15}-$, $-NR^{15}CO-$, $-C(O)O-$, $-OC(O)-$, $-O-$, $-S-$, $-S(O)-$, $-SO_2-$, $-SO_2NR^{15}-$, $-NR^{15}SO_2-$ and $-P(O)OH-$, wherein each q is an integer from 1 to 6;
- each $R^{13}$ is independently selected from hydrogen, an alkyl, a substituted alkyl, an aryl, and a substituted aryl; and
- each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In some embodiments, $L^2$ comprises:

$-(T^5-V^5)_e-(T^6-V^6)_f-(T^7-V^7)_g-(T^8-V^8)_h-,$ wherein
- e, f, g and h are each independently 0 or 1;
- $T^5$, $T^6$, $T^7$ and $T^8$ are each independently selected from a covalent bond, $(C_1-C_{12})$alkyl, substituted $(C_1-C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, $-(CR^{13}OH)_m-$, 4-amino-piperidine (4AP), an acetal group, a hydrazine, a disulfide, and an ester, wherein EDA is an ethylene diamine moiety, PEG is a polyethylene glycol, and AA is an amino acid residue or an amino acid analog, wherein each w is an integer from 1 to 20, each n is an integer from 1 to 30, each p is an integer from 1 to 20, and each m is an integer from 1 to 12;
- $V^5$, $V^6$, $V^7$ and $V^8$ are each independently selected from the group consisting of a covalent bond, $-CO-$, $-NR^{15}-$, $-NR^{15}(CH_2)_q-$, $-NR^{15}(C_6H_4)-$, $-CONR^{15}-$, $-NR^{15}CO-$, $-C(O)O-$, $-OC(O)-$, $-O-$, $-S-$, $-S(O)-$, $-SO_2-$, $-SO_2NR^{15}-$, $-NR^{15}SO_2-$ and $-P(O)OH-$, wherein each q is an integer from 1 to 6;
- each $R^{13}$ is independently selected from hydrogen, an alkyl, a substituted alkyl, an aryl, and a substituted aryl; and
- each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In some embodiments, $L^1$ is as described herein, where:
- $T^1$ is selected from a $(C_1-C_{12})$alkyl and a substituted $(C_1-C_{12})$alkyl;
- $T^2$, $T^3$, and $T^4$ are each independently selected from aryl, substituted aryl, heteroaryl, substituted heteroaryl, cycloalkyl, substituted cycloalkyl, heterocyclyl, and substituted heterocyclyl, $(EDA)_w$, $(PEG)_n$, $(C_1-C_{12})$alkyl, substituted $(C_1-C_{12})$alkyl, $(AA)_p$, $-(CR^{13}OH)_m-$, 4-amino-piperidine (4AP), an acetal group, a hydrazine, and an ester; and
- $V^1$, $V^2$, $V^3$ and $V^4$ are each independently selected from the group consisting of a covalent bond, $-CO-$, $-NR^{15}-$, $-NR^{15}(CH_2)_q-$, $-NR^{15}(C_6H_4)-$, $-CONR^{15}-$, $-NR^{15}CO-$, $-C(O)O-$, $-OC(O)-$, $-O-$, $-S-$, $-S(O)-$, $-SO_2-$, $-SO_2NR^{15}-$, $-NR^{15}SO_2-$, and $-P(O)OH-$;

wherein:

(PEG)$_n$ is

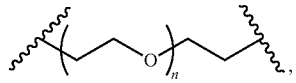

where n is an integer from 1 to 30;
EDA is an ethylene diamine moiety having the following structure:

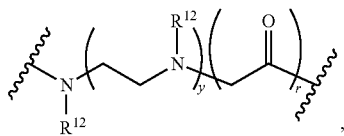

where y is an integer from 1 to 6 and r is 0 or 1;
4-amino-piperidine (4AP) is R;

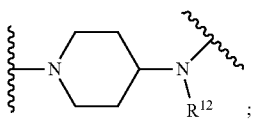

each $R^{12}$ and $R^{15}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring; and
$R^{13}$ is selected from hydrogen, an alkyl, a substituted alkyl, an aryl, and a substituted aryl.

In some embodiments, $L^1$ is as described herein, where:
$T^1$ is ($C_1$-$C_{12}$)alkyl and $V^1$ is —CO—;
$T^2$ is an amino acid analog and $V^2$ is —NH—;
$T^3$ is (PEG)$_n$ and $V^3$ is —CO—; and
d is 0.

In some embodiments, $L^2$ is as described herein, where:
$T^5$ is a covalent bond and $V^5$ is —CO—; and
f, g and h are 0.

In some embodiments, $L^2$ is as described herein, where:
$T^5$ is a covalent bond and $V^5$ is —CONR$^{15}$—;
$T^6$ is ($C_1$-$C_{12}$)alkyl and $V^6$ is —CO—; and
g and h are 0.

In some embodiments, the drug is selected from a cytotoxin, a kinase inhibitor, an immunostimulatory agent, a toll-like receptor (TLR) agonist, an oligonucleotide, an aptamer, a cytokine, a steroid, and a peptide. In some embodiments, the drug is selected from an auristatin, a maytansine, and a duocarmycin. In some embodiments, the drug is selected from Tubulysin M, Calicheamicin, SN-38, Exatecan, a STAT3 inhibitor, alpha-Amanitin, an aurora kinase inhibitor, belotecan, 9-aminocamptothecin (9-AC), and an anthracycline.

Aspects of the present disclosure include a compound that includes a cleavable linker for linking an antibody to a drug, where the cleavable linker includes a first enzymatically cleavable moiety and a second enzymatically cleavable moiety having a glycoside selected from a galactoside, a glucoside, a mannoside, a fucoside, O-GlcNAc, and O-GalNAc.

In some embodiments, the compound is of formula (II):

(II)

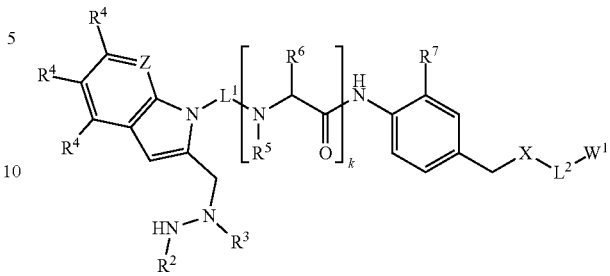

wherein
Z is $CR^4$ or N;
X is O or $NR^4$;
$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;
each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
each $R^5$ is independently selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
each $R^6$ is independently selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
k is an integer from 1 to 10;
$R^7$ comprises the second enzymatically cleavable moiety;
$L^1$ is a first linker;
$L^2$ is a second linker; and
$W^1$ is a drug.

In some embodiments, k is 2, and the compound is of formula (IIa):

(IIa)

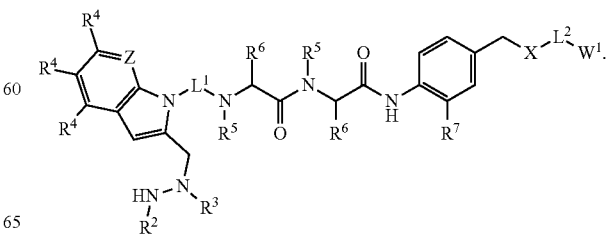

In some embodiments, the second cleavable moiety comprises a galactoside. In some embodiments, the second cleavable moiety comprises a glucoside. In some embodiments, the second cleavable moiety comprises a mannoside. In some embodiments, the second enzymatically cleavable moiety comprises a fucisode. In some embodiments, the second enzymatically cleavable moiety comprises O-GlcNAc. In some embodiments, the second enzymatically cleavable moiety comprises O-GalNAc.

In some embodiments, the compound is of formula (IIb):

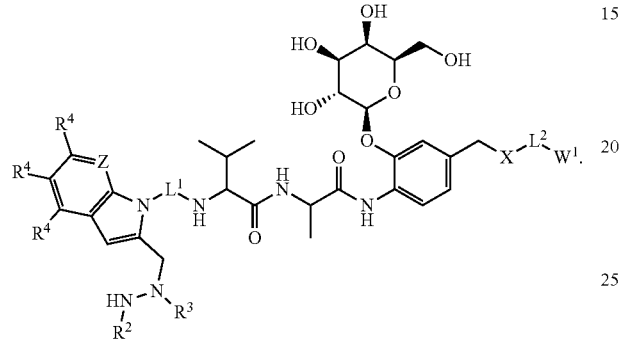

(IIb)

In some embodiments, the compound is of formula (IIc):

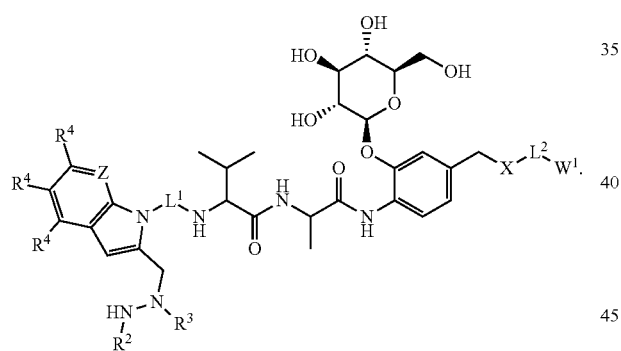

(IIc)

In some embodiments, the compound is of formula (IId):

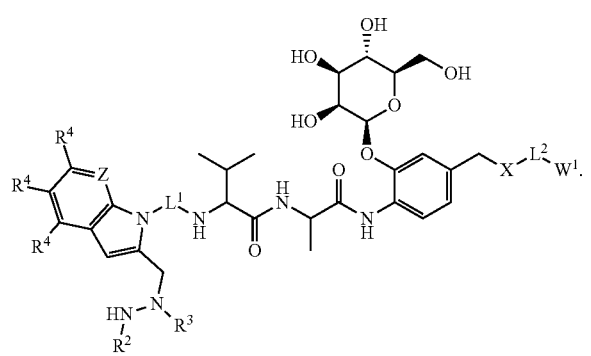

(IId)

In some embodiments the compound is of formula (IIe).

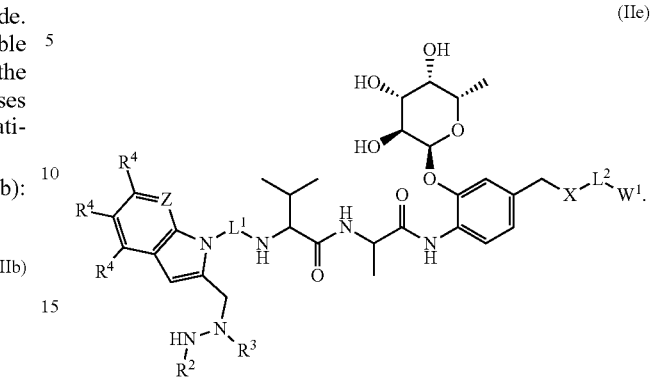

(IIe)

In some embodiments, the compound is of formula (IIf):

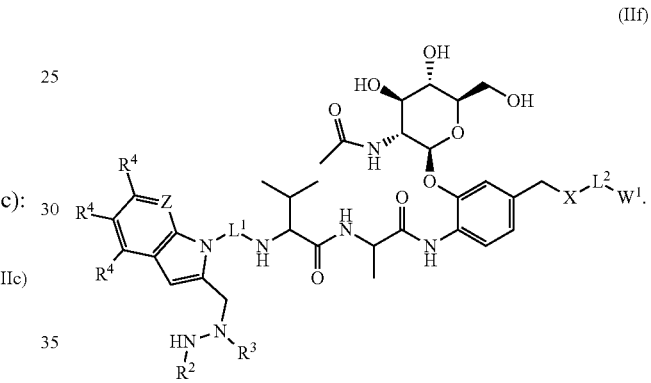

(IIf)

In some embodiments, the compound is of formula (IIg):

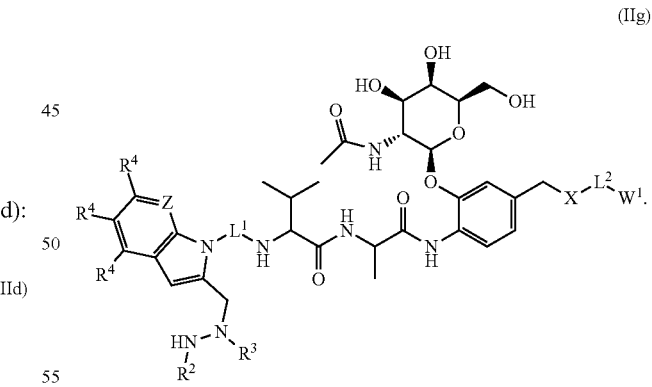

(IIg)

In some embodiments, $L^1$ comprises:

$-(T^1-V^1)_a-(T^2-V^2)_b-(T^3-V^3)_c-(T^4-V^4)_d$, wherein a, b, c and d are each independently 0 or 1;

$T^1$, $T^2$, $T^3$ and $T^4$ are each independently selected from a covalent bond, $(C_1-C_{12})$alkyl, substituted $(C_1-C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, $-(CR^{13}OH)_m-$, 4-amino-piperidine (4AP), an acetal group, a hydrazine, a disulfide, and an ester, wherein EDA is an ethylene diamine moiety, PEG is a polyethylene glycol, and AA is an amino acid residue or an amino acid analog, wherein each w is an integer from 1 to 20, each n is an integer from 1 to 30, each p is an integer from 1 to 20, and each m is an integer from 1 to 12;

$V^1$, $V^2$, $V^3$ and $V^4$ are each independently selected from the group consisting of a covalent bond, —CO—, —$NR^{15}$—, —$NR^{15}(CH_2)_q$—, —$NR^{15}(C_6H_4)$—, —$CONR^{15}$—, —$NR^{15}CO$—, —C(O)O—, —OC(O)—, —O—, —S—, —S(O)—, —$SO_2$—, —$SO_2NR^{15}$—, —$NR^{15}SO_2$— and —P(O)OH—, wherein each q is an integer from 1 to 6;

each $R^{13}$ is independently selected from hydrogen, an alkyl, a substituted alkyl, an aryl, and a substituted aryl; and each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In some embodiments, $L^2$ comprises:

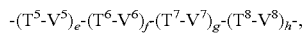

wherein e, f, g and h are each independently 0 or 1;

$T^5$, $T^6$, $T^7$ and $T^8$ are each independently selected from a covalent bond, $(C_1-C_{12})$alkyl, substituted $(C_1-C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, —$(CR^{13}OH)_m$—, 4-amino-piperidine (4AP), an acetal group, a hydrazine, a disulfide, and an ester, wherein EDA is an ethylene diamine moiety, PEG is a polyethylene glycol, and AA is an amino acid residue or an amino acid analog, wherein each w is an integer from 1 to 20, each n is an integer from 1 to 30, each p is an integer from 1 to 20, and each m is an integer from 1 to 12;

$V^5$, $V^6$, $V^7$ and $V^8$ are each independently selected from the group consisting of a covalent bond, —CO—, —$NR^{15}$—, —$NR^{15}(CH_2)_q$—, —$NR^{15}(C_6H_4)$—, —$CONR^{15}$—, —$NR^{15}CO$—, —C(O)O—, —OC(O)—, —O—, —S—, —S(O)—, —$SO_2$—, —$SO_2NR^{15}$—, —$NR^{15}SO_2$— and —P(O)OH—, wherein each q is an integer from 1 to 6;

each $R^{13}$ is independently selected from hydrogen, an alkyl, a substituted alkyl, an aryl, and a substituted aryl; and each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In some embodiments, $L^1$ is as described herein, wherein:
$T^1$ is selected from a $(C_1-C_{12})$alkyl and a substituted $(C_1-C_{12})$alkyl;
$T^2$, $T^3$, and $T^4$ are each independently selected from aryl, substituted aryl, heteroaryl, substituted heteroaryl, cycloalkyl, substituted cycloalkyl, heterocyclyl, and substituted heterocyclyl, $(EDA)_w$, $(PEG)_n$, $(C_1-C_{12})$alkyl, substituted $(C_1-C_{12})$alkyl, $(AA)_p$, —$(CR^{13}OH)_m$—, 4-amino-piperidine (4AP), an acetal group, a hydrazine, and an ester; and $V^1$, $V^2$, $V^3$ and $V^4$ are each independently selected from the group consisting of a covalent bond, —CO—, —$NR^{15}$—, —$NR^{15}(CH_2)_q$—, —$NR^{15}(C_6H_4)$—, —$CONR^{15}$—, —$NR^{15}CO$—, —C(O)O—, —OC(O)—, —O—, —S—, —S(O)—, —$SO_2$—, —$SO_2NR^{15}$—, —$NR^{15}SO_2$—, and —P(O)OH—;

wherein:

$(PEG)_n$ is

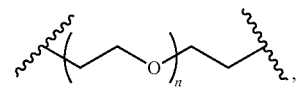

where n is an integer from 1 to 30;

EDA is an ethylene diamine moiety having the following structure:

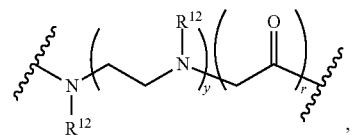

where y is an integer from 1 to 6 and r is 0 or 1;

4-amino-piperidine (4AP) is

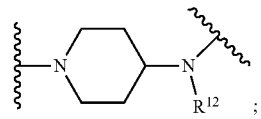

each $R^{12}$ and $R^{15}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring; and $R^{13}$ is selected from hydrogen, an alkyl, a substituted alkyl, an aryl, and a substituted aryl.

In some embodiments, $L^1$ is as described herein, wherein:
$T^1$ is $(C_1-C_{12})$alkyl and $V^1$ is —CO—;
$T^2$ is an amino acid analog and $V^2$ is —NH—;
$T^3$ is $(PEG)_n$ and $V^3$ is —CO—; and
d is 0.

In some embodiments, $L^2$ is as described herein, wherein:
$T^5$ is a covalent bond and $V^5$ is —CO—; and
f, g and h are 0.

In some embodiments, $L^2$ is as described herein, wherein:
$T^5$ is a covalent bond and $V^5$ is —$CONR^{15}$—;
$T^6$ is $(C_1-C_{12})$alkyl and $V^6$ is —CO—; and
g and h are 0.

In some embodiments, the drug is selected from a cytotoxin, a kinase inhibitor, an immunostimulatory agent, a toll-like receptor (TLR) agonist, an oligonucleotide, an aptamer, a cytokine, a steroid, and a peptide. In some embodiments, the drug is selected from an auristatin, a maytansine, and a duocarmycin. In some embodiments, the drug is selected from Tubulysin M, Calicheamicin, SN-38, Exatecan, a STAT3 inhibitor, alpha-Amanitin, an aurora kinase inhibitor, belotecan, 9-aminocamptothecin (9-AC), and an anthracycline.

Aspects of the present disclosure include a pharmaceutical composition comprising a conjugate as described herein, and a pharmaceutically-acceptable excipient.

Aspects of the present disclosure include a method of administering a conjugate to a subject, where the method includes administering to a subject a conjugate as described herein.

Aspects of the present disclosure include a method of treating cancer in a subject, where the method includes administering to the subject a therapeutically effective amount of a pharmaceutical composition comprising a conjugate as described herein, where the administering is effective to treat cancer in the subject.

DEFINITIONS

Figure 1:
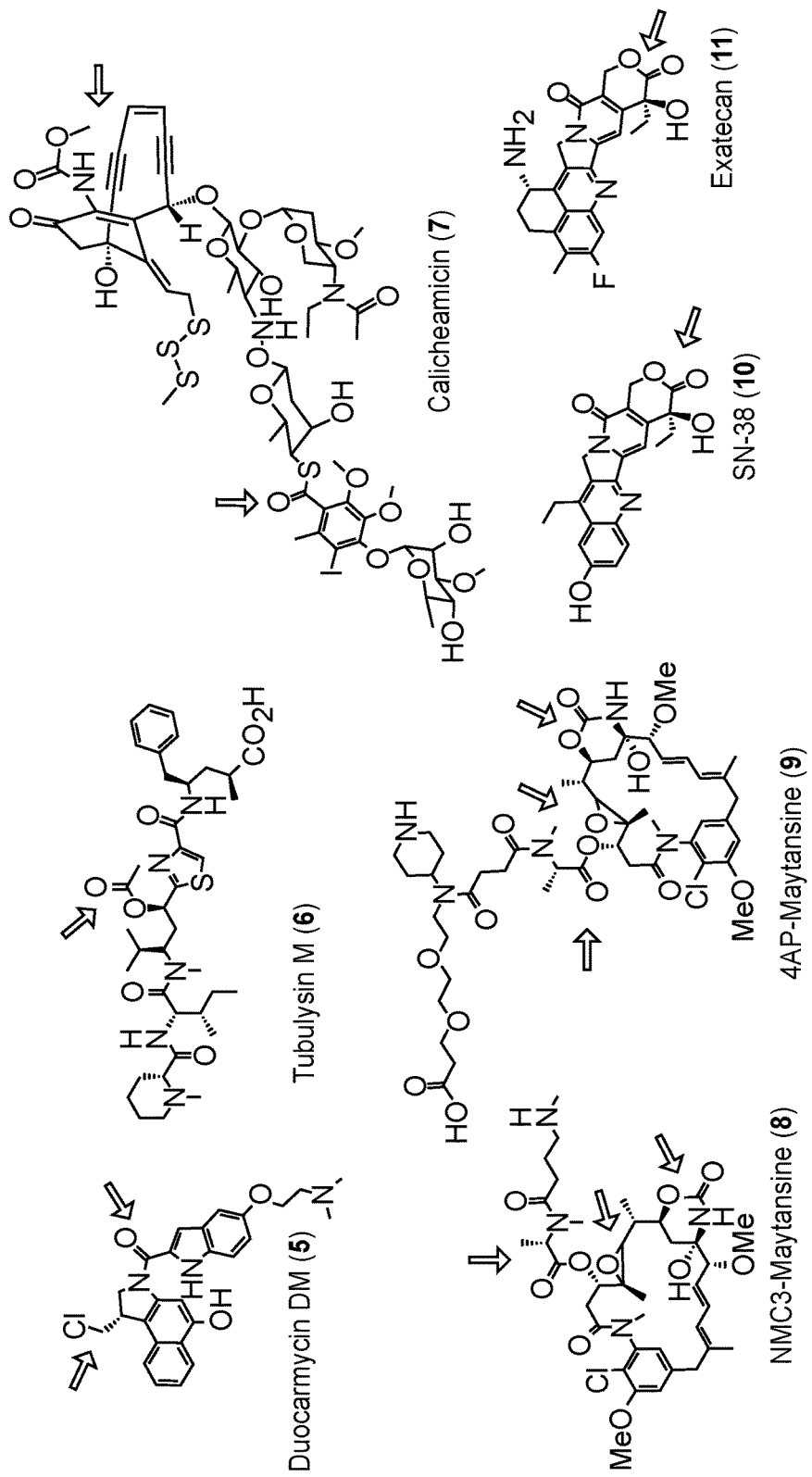
FIG. 1 shows cytotoxins commonly used to generate therapeutic antibody-drug conjugates. Arrows indicate base-labile groups.

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "substituted alkyl" refers to an alkyl group as defined herein wherein one or more carbon atoms in the alkyl chain (except the $C_1$ carbon atom) have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

"Acylamino" refers to the groups —NR$^{20}$C(O)alkyl, —NR$^{20}$C(O)substituted alkyl, —NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O— substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO-substituted alkyl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic. To satisfy valence requirements, any heteroatoms in such heteroaryl rings may or may not be bonded to H or a substituent group, e.g., an alkyl group or other substituent as described herein. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from nitrogen, sulfur, or oxygen, where, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties. To satisfy valence requirements, any heteroatoms in such heterocyclic rings may or may not be bonded to one or more H or one or more substituent group(s), e.g., an alkyl group or other substituent as described herein.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclyl, heterocylooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, and —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Sulfate" or "sulfate ester" refers the group —O—SO$_2$—OH, —O—SO$_2$—O-alkyl, —O—SO$_2$—O-substituted alkyl, —O—SO$_2$—O-alkenyl, —O—SO$_2$—O-substituted alkenyl, —O—SO$_2$—O-cycloalkyl, —O—SO$_2$—O-substituted cycloalkyl, —O—SO$_2$—O-cycloalkenyl, —O—SO$_2$—O-substituted cylcoalkenyl, —O—SO$_2$—O-aryl, —O—SO$_2$—O-substituted aryl, —O—SO$_2$—O-heteroaryl, —O—SO$_2$—O-substituted heteroaryl, —O—SO$_2$—O-heterocyclic, and —O—SO$_2$—O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocylooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O-M$^+$, —OR$^{70}$, —SR$^{70}$, —S-M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_{35}^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S-M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S-M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant host cell); immunologically tagged proteins; and the like.

"Native amino acid sequence" or "parent amino acid sequence" are used interchangeably herein to refer to the amino acid sequence of a polypeptide prior to modification to include a modified amino acid residue.

The terms "amino acid analog," "unnatural amino acid," and the like may be used interchangeably, and include amino acid-like compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acid analogs also include amino acid analogs with the same stereochemistry as in the naturally occurring D-form, as well as the L-form of amino acid analogs. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like.

The terms "amino acid side chain" or "side chain of an amino acid" and the like may be used to refer to the substituent attached to the α-carbon of an amino acid residue, including natural amino acids, unnatural amino acids, and amino acid analogs. An amino acid side chain can also include an amino acid side chain as described in the context of the modified amino acids and/or conjugates described herein.

The term "carbohydrate" and the like may be used to refer to monomers units and/or polymers of monosaccharides, disaccharides, oligosaccharides, and polysaccharides. The term sugar may be used to refer to the smaller carbohydrates, such as monosaccharides, disaccharides. The term "carbohydrate derivative" includes compounds where one or more functional groups of a carbohydrate of interest are substituted (replaced by any convenient substituent), modified (converted to another group using any convenient chemistry) or absent (e.g., eliminated or replaced by H). A variety of carbohydrates and carbohydrate derivatives are available and may be adapted for use in the subject compounds and conjugates.

The term "glycoside" or "glycosyl" refers to a sugar molecule or group bound to a moiety via a glycosidic bond. For example, the moiety that the glycoside is bound to can be a cleavable linker as described herein. A glycosidic bond can link the glycoside to the other moiety through various types of bonds, such as, but not limited to, an O-glycosidic bond (an O-glycoside), an N-glycosidic bond (a glycosylamine), an S-glycosidic bond (a thioglycoside), or C-glycosidic bond (a C-glycoside or C-glycosyl). In some cases, glycosides can be cleaved from the moiety they are attached to, such as by chemically-mediated hydrolysis or enzymatically-mediated hydrolysis.

The term "antibody" is used in the broadest sense and includes monoclonal antibodies (including full length monoclonal antibodies), polyclonal antibodies, and multispecific antibodies (e.g., bispecific antibodies), humanized antibodies, single-chain antibodies, chimeric antibodies, antibody fragments (e.g., Fab fragments), and the like. An antibody is capable of binding a target antigen. (Janeway, C., Travers, P., Walport, M., Shlomchik (2001) Immuno Biology, 5th Ed., Garland Publishing, New York). A target antigen can have one or more binding sites, also called epitopes, recognized by complementarity determining regions (CDRs) formed by one or more variable regions of an antibody.

The term "natural antibody" refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject rabbit antibody may be humanized according to the methods set forth in US20040086979 and US20050033031. Accordingly, the antibodies described above may be humanized using methods that are well known in the art.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a mouse antibody and the constant or effector domain from a human antibody, although domains from other mammalian species may be used.

An immunoglobulin polypeptide immunoglobulin light or heavy chain variable region is composed of a framework region (FR) interrupted by three hypervariable regions, also called "complementarity determining regions" or "CDRs". The extent of the framework region and CDRs have been defined (see, "Sequences of Proteins of Immunological Interest," E. Kabat et al., U.S. Department of Health and Human Services, 1991). The framework region of an antibody, that is the combined framework regions of the constituent light and heavy chains, serves to position and align the CDRs. The CDRs are primarily responsible for binding to an epitope of an antigen.

A "parent Ig polypeptide" is a polypeptide comprising an amino acid sequence which lacks an aldehyde-tagged constant region as described herein. The parent polypeptide may comprise a native sequence constant region, or may comprise a constant region with pre-existing amino acid sequence modifications (such as additions, deletions and/or substitutions).

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

By "reactive partner" is meant a molecule or molecular moiety that specifically reacts with another reactive partner to produce a reaction product. Exemplary reactive partners include a cysteine or serine of a sulfatase motif and Formylglycine Generating Enzyme (FGE), which react to form a reaction product of a converted aldehyde tag containing a formylglycine (FGly) in lieu of cysteine or serine in the motif. Other exemplary reactive partners include an aldehyde of an fGly residue of a converted aldehyde tag (e.g., a reactive aldehyde group) and an "aldehyde-reactive reactive partner", which comprises an aldehyde-reactive group and a moiety of interest, and which reacts to form a reaction product of a modified aldehyde tagged polypeptide having the moiety of interest conjugated to the modified polypeptide through a modified fGly residue.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "internal site" as used in referenced to a polypeptide or an amino acid sequence of a polypeptide means a region of the polypeptide that is not at the N-terminus or at the C-terminus.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides antibody-drug conjugate structures, that include a cleavable linker that links the antibody to the drug. The cleavable linker includes a first enzymatically cleavable moiety and a second enzymatically cleavable moiety that includes a glycoside selected from a galactoside, a glucoside, a mannoside, a fucoside, O-GlcNAc, and O-GalNAc. The disclosure also encompasses methods of production of such conjugates, as well as methods of using the same.

Antibody-Drug Conjugates

The present disclosure provides a conjugate, e.g., an antibody-drug conjugate (ADC). By "conjugate" is meant a first moiety (e.g., an antibody) is stably associated with a second moiety (e.g., a drug or active agent). For example, an antibody-drug conjugate includes a drug or active agent stably associated with another moiety (e.g., the antibody). By "stably associated" is meant that a moiety is bound to another moiety or structure under standard conditions. In certain embodiments, the first and second moieties are bound to each other through one or more functional groups and covalent bonds. For example, the one or more functional groups and covalent bonds can include a cleavable linker as described herein.

In certain embodiments, the conjugate is a polypeptide conjugate, which includes a polypeptide (e.g., an antibody) conjugated to a second moiety. In certain embodiments, the moiety conjugated to the polypeptide can be any of a variety of moieties of interest such as, but not limited to, a drug, an active agent, a detectable label, a water-soluble polymer, or a moiety for immobilization of the polypeptide to a membrane or a surface. In certain embodiments, the conjugate is a drug conjugate, where a polypeptide is an antibody, thus providing an antibody-drug conjugate. For instance, the conjugate can be a drug conjugate, where a polypeptide is conjugated to a drug or an active agent. Various types of drugs or active agents may be used in the conjugates and are described in more detail below.

In certain embodiments, the conjugate is an antibody-drug conjugate where the antibody and the drug are linked together by a linker. In some instances, the linker is a cleavable linker. A cleavable linker is a linker that includes one or more cleavable moieties, where the cleavable moiety includes one or more bonds that can dissociate under certain conditions, thus separating the cleavable linker into two or more separatable portions. For example, the cleavable moiety may include one or more covalent bonds, which under certain conditions, can dissociate or break apart to separate the cleavable linker into two or more portions. As such a cleavable linker can be included in an antibody-drug conjugate, such that under appropriate conditions, the cleavable linker is cleaved to separate or release the drug from the antibody at a desired target site of action for the drug.

In some instances, the cleavable linker includes two cleavable moieties, such as a first cleavable moiety and a second cleavable moiety. The cleavable moieties can be configured such that cleavage of both cleavable moieties is needed in order to separate or release the drug from the antibody at a desired target site of action for the drug. For example, cleavage of the cleavable linker can be achieved by initially cleaving one of the two cleavable moieties and then cleaving the other of the two cleavable moieties. In certain embodiments, the cleavable linker includes a first cleavable moiety and a second cleavable moiety that hinders cleavage of the first cleavable moiety. By "hinders cleavage" is meant that the presence of an uncleaved second cleavable moiety reduces the likelihood or substantially inhibits the cleavage of the first cleavable moiety, thus substantially reducing the amount or preventing the cleavage of the cleavable linker. For instance, the presence of uncleaved second cleavable moiety can hinder cleavage of the first cleavable moiety. The hinderance of cleavage of the first cleavable moiety by the presence of the second cleavable moiety, in turn, substantially reduces the amount or prevents the release of the drug from the antibody. For example, the premature release of the drug from the antibody can be substantially reduced or prevented until the antibody-drug conjugate is at or near the desired target site of action for the drug.

In some cases, since the second cleavable moiety hinders cleavage of the first cleavable moiety, cleavage of the cleavable linker can be achieved by initially cleaving the second cleavable moiety and then cleaving the first cleavable moiety. Cleavage of the second cleavable moiety can reduce or eliminate the hinderance on the cleavage of the first cleavable moiety, thus allowing the first cleavable moiety to be cleaved. Cleavage of the first cleavable moiety can result in the cleavable linker dissociating or separating into two or more portions as described above to release the drug from the antibody-drug conjugate. In some instances, cleavage of the first cleavable moiety does not substantially occur in the presence of an uncleaved second cleavable moiety. By substantially is meant that about 10% or less cleavage of the first cleavable moiety occurs in the presence of an uncleaved second cleavable moiety, such as about 9% or less, or about 8% or less, or about 7% or less, or about 6% or less, or about 5% or less, or about 4% or less, or about 3% or less, or about 2% or less, or about 1% or less, or about 0.5% or less, or about 0.1% or less cleavage of the first cleavable moiety occurs in the presence of an uncleaved second cleavable moiety.

Stated another way, the second cleavable moiety can protect the first cleavable moiety from cleavage. For instance, the presence of uncleaved second cleavable moiety can protect the first cleavable moiety from cleavage, and thus substantially reduce or prevent premature release of the drug from the antibody until the antibody-drug conjugate is at or near the desired target site of action for the drug. As such, cleavage of the second cleavable moiety exposes the first cleavable moiety (e.g., deprotects the first cleavable moiety), thus allowing the first cleavable moiety to be cleaved, which results in cleavage of the cleavable linker, which, in turn, separates or releases the drug from the antibody at a desired target site of action for the drug as described above. In certain instances, cleavage of the second cleavable moiety exposes the first cleavable moiety to subsequent cleavage, but cleavage of the second cleavable moiety does not in and of itself result in cleavage of the cleavable linker (i.e., cleavage of the first cleavable moiety is still needed in order to cleave the cleavable linker).

The cleavable moieties included in the cleavable linker may each be an enzymatically cleavable moiety. For example, the first cleavable moiety can be a first enzymatically cleavable moiety and the second cleavable moiety can be a second enzymatically cleavable moiety. An enzymatically cleavable moiety is a cleavable moiety that can be separated into two or more portions as described above through the enzymatic action of an enzyme. The enzymatically cleavable moiety can be any cleavable moiety that can be cleaved through the enzymatic action of an enzyme, such as, but not limited to, a peptide, a glycoside, and the like. In some instances, the enzyme that cleaves the enzymatically cleavable moiety is present at a desired target site of action, such as the desired target site of action of the drug that is to be released from the antibody-drug conjugate. In some cases, the enzyme that cleaves the enzymatically cleavable moiety is not present in a significant amount in other areas, such as in whole blood, plasma or serum. As such, the cleavage of an enzymatically cleavable moiety can be controlled such that substantial cleavage occurs at the desired site of action, whereas cleavage does not significantly occur in other areas or before the antibody-drug conjugate reaches the desired site of action.

For example, as described herein, antibody-drug conjugates of the present disclosure can be used for the treatment of cancer, such as for the delivery of a cancer therapeutic drug to a desired site of action where the cancer cells are present. In some cases, enzymes, such as the protease enzyme cathepsin B, can be a biomarker for cancer that is overexpressed in cancer cells. The overexpression, and thus localization, of certain enzymes in cancer can be used in the context of the enzymatically cleavable moieties included in the cleavable linkers of the antibody-drug conjugates of the present disclosure to specifically release the drug at the desired site of action (i.e., the site of the cancer (and overexpressed enzyme)). Thus, in some embodiments, the enzymatically cleavable moiety is a cleavable moiety (e.g., a peptide) that can be cleaved by an enzyme that is overexpressed in cancer cells. For instance, the enzyme can be the protease enzyme cathepsin B. As such, in some instances, the enzymatically cleavable moiety is a cleavable moiety (e.g., a peptide) that can be cleaved by a protease enzyme, such as cathepsin B.

In certain embodiments, the enzymatically cleavable moiety is a peptide. The peptide can be any peptide suitable for use in the cleavable linker and that can be cleaved through the enzymatic action of an enzyme. Non-limiting examples of peptides that can be used as an enzymatically cleavable moiety include, for example, Val-Ala, Phe-Lys, and the like. For example, the first cleavable moiety described above (i.e., the cleavable moiety protected from premature cleavage by the second cleavable moiety) can include a peptide. The presence of uncleaved second cleavable moiety can protect the first cleavable moiety (peptide) from cleavage by a protease enzyme (e.g., cathepsin B), and thus substantially reduce or prevent premature release of the drug from the antibody until the antibody-drug conjugate is at or near the desired target site of action for the drug. In some instances, one of the amino acid residues of the peptide that comprises the first cleavable moiety is linked to or includes a substituent, where the substituent comprises the second cleavable moiety. In some instances, the second cleavable moiety includes a glycoside.

In some embodiments, the enzymatically cleavable moiety is sugar moiety, such as a glycoside (or glyosyl). In some cases, the glycoside can facilitate an increase in the hydrophilicity of the cleavable linker as compared to a cleavable linker that does not include the glycoside. The glycoside can be any glycoside suitable for use in the cleavable linker and that can be cleaved through the enzymatic action of an enzyme. For example, the second cleavable moiety (i.e., the cleavable moiety that protects the first cleavable moiety from premature cleavage) can be a glycoside. For instance, in some embodiments, the first cleavable moiety includes a peptide and the second cleavable moiety includes a glycoside. In certain embodiments, the second cleavable moiety is a glycoside selected from a galactoside, a glucoside, a mannoside, a fucoside, O-GlcNAc and O-GalNAc. In some instances, the second cleavable moiety is a galactoside. In some instances, the second cleavable moiety is a glucoside. In some instances, the second cleavable moiety is a mannoside. In some instances, the second cleavable moiety is a fucoside. In some instances, the second cleavable moiety is O-GlcNAc. In some instances, the second cleavable moiety is O-GalNAc.

The glycoside can be attached (covalently bonded) to the cleavable linker through a glycosidic bond. The glycosidic bond can link the glycoside to the cleavable linker through various types of bonds, such as, but not limited to, an O-glycosidic bond (an O-glycoside), an N-glycosidic bond (a glycosylamine), an S-glycosidic bond (a thioglycoside), or C-glycosidic bond (a C-glycoside or C-glycosyl). In some instances, the glycosidic bond is an O-glycosidic bond (an O-glycoside). In some cases, the glycoside can be cleaved from the cleavable linker it is attached to by an enzyme (e.g., through enzymatically-mediated hydrolysis of the glycosidic bond). A glycoside can be removed or cleaved from the cleavable linker by any convenient enzyme that is able to carry out the cleavage (hydrolysis) of the glycosidic bond that attaches the glycoside to the cleavable linker. An example of an enzyme that can be used to mediate the cleavage (hydrolysis) of the glycosidic bond that attaches the glycoside to the cleavable linker is a glycosidase, such as a galactosidase, a glucosidase, a mannosidase, a fucosidase, and the like. Other suitable enzymes may also be used to mediate the cleavage (hydrolysis) of the glycosidic bond that attaches the glycoside to the cleavable linker. In some cases, the enzyme used to mediate the cleavage (hydrolysis) of the glycosidic bond that attaches the glycoside to the cleavable linker is found at or near the desired site of action for the drug of the antibody-drug conjugate. For instance, the enzyme can be a lysosomal enzyme, such as a lysosomal glycosidase, found in cells at or near the desired site of action for the drug of the antibody-drug conjugate. In some cases, the enzyme is an enzyme found at or near the target site where the enzyme that mediates cleavage of the first cleavable moiety is found.

The moiety of interest (e.g., drug or active agent) can be conjugated to the polypeptide (e.g., antibody) at any desired site of the polypeptide. Thus, the present disclosure provides, for example, a modified polypeptide having a moiety conjugated at a site at or near the C-terminus of the polypeptide. Other examples include a modified polypeptide having a moiety conjugated at a position at or near the N-terminus of the polypeptide. Examples also include a modified polypeptide having a moiety conjugated at a position between the C-terminus and the N-terminus of the polypeptide (e.g., at an internal site of the polypeptide). Combinations of the above are also possible where the modified polypeptide is conjugated to two or more moieties.

In certain embodiments, a conjugate of the present disclosure includes a drug or active agent conjugated to an amino acid reside of a polypeptide at the α-carbon of an amino acid residue. Stated another way, a conjugate includes a polypeptide where the side chain of one or more amino acid residues in the polypeptide have been modified to be attached to a drug or active agent (e.g., attached to a drug or active agent through a linker as described herein). For example, a conjugate includes a polypeptide where the α-carbon of one or more amino acid residues in the polypeptide has been modified to be attached to a drug or active agent (e.g., attached to a drug or active agent through a linker as described herein).

Embodiments of the present disclosure include conjugates where a polypeptide is conjugated to one or more moieties, such as 2 moieties, 3 moieties, 4 moieties, 5 moieties, 6 moieties, 7 moieties, 8 moieties, 9 moieties, or 10 or more moieties. The moieties may be conjugated to the polypeptide at one or more sites in the polypeptide. For example, one or more moieties may be conjugated to a single amino acid residue of the polypeptide. In some cases, one moiety is conjugated to an amino acid residue of the polypeptide. In other embodiments, two moieties may be conjugated to the same amino acid residue of the polypeptide. In other embodiments, a first moiety is conjugated to a first amino acid residue of the polypeptide and a second moiety is conjugated to a second amino acid residue of the polypeptide. Combinations of the above are also possible, for example where a polypeptide is conjugated to a first moiety at a first amino acid residue and conjugated to two other moieties at a second amino acid residue. Other combinations are also possible, such as, but not limited to, a polypeptide conjugated to first and second moieties at a first amino acid residue and conjugated to third and fourth moieties at a second amino acid residue, etc.

The one or more amino acid residues of the polypeptide that are conjugated to the one or more moieties may be naturally occurring amino acids, unnatural amino acids, or combinations thereof. For instance, the conjugate may include a moiety conjugated to a naturally occurring amino acid residue of the polypeptide. In other instances, the conjugate may include a moiety conjugated to an unnatural amino acid residue of the polypeptide. One or more moieties may be conjugated to the polypeptide at a single natural or unnatural amino acid residue as described above. One or more natural or unnatural amino acid residues in the polypeptide may be conjugated to the moiety or moieties as described herein. For example, two (or more) amino acid residues (e.g., natural or unnatural amino acid residues) in the polypeptide may each be conjugated to one or two moieties, such that multiple sites in the polypeptide are modified.

As described herein, a polypeptide may be conjugated to one or more moieties. In certain embodiments, the moiety of interest is a chemical entity, such as a drug, an active agent, or a detectable label. For example, a drug (or active agent) may be conjugated to the polypeptide, or in other embodiments, a detectable label may be conjugated to the polypeptide. Thus, for instance, embodiments of the present disclosure include, but are not limited to, the following: a conjugate of a polypeptide and a drug; a conjugate of a polypeptide and an active agent; a conjugate of a polypeptide and a detectable label; a conjugate of two or more drugs and a polypeptide; a conjugate of two or more detectable labels and a polypeptide; and the like.

In certain embodiments, the polypeptide (e.g., antibody) and the moiety of interest (e.g., drug or active agent) are conjugated through a coupling moiety. For example, the polypeptide and the moiety of interest may each be bound (e.g., covalently bonded) to the coupling moiety, thus indirectly binding the polypeptide and the moiety of interest together through the coupling moiety. In some cases, the coupling moiety includes a hydrazinyl-indolyl or a hydrazinyl-pyrrolo-pyridinyl compound, or a derivative of a hydrazinyl-indolyl or a hydrazinyl-pyrrolo-pyridinyl compound. For instance, a general scheme for coupling a moiety of interest to a polypeptide through a hydrazinyl-indolyl or a hydrazinyl-pyrrolo-pyridinyl coupling moiety is shown in the general reaction scheme below. Hydrazinyl-indolyl and hydrazinyl-pyrrolo-pyridinyl coupling moiety are also referred to herein as a hydrazino-iso-Pictet-Spengler (HIPS) coupling moiety and an aza-hydrazino-iso-Pictet-Spengler (azaHIPS) coupling moiety, respectively.

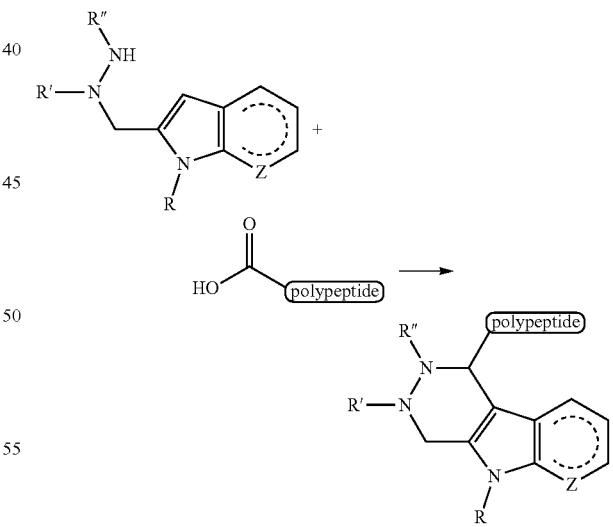

In the reaction scheme above, R includes the moiety of interest (e.g., a drug or active agent) that is conjugated to the polypeptide (e.g., conjugated to the polypeptide through a cleavable linker as described herein). As shown in the reaction scheme above, a polypeptide that includes a 2-formylglycine residue (fGly) is reacted with a drug or active agent that has been modified to include a coupling moiety (e.g., a hydrazinyl-indolyl or a hydrazinyl-pyrrolo-pyridinyl coupling moiety) to produce a polypeptide conjugate attached to the coupling moiety, thus attaching the drug or active agent to the polypeptide through the coupling moiety.

As described herein, the moiety can be any of a variety of moieties such as, but not limited to, chemical entity, such as a detectable label, or a drug or active agent. R' and R" may each independently be any desired substituent, such as, but not limited to, hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. Z may be $CR^{21}$, $NR^{22}$, N, O or S, where $R^{21}$ and $R^{22}$ are each independently selected from any of the substituents described for R' and R" above.

Other hydrazinyl-indolyl or hydrazinyl-pyrrolo-pyridinyl coupling moieties are also possible, as shown in the conjugates and compounds described herein. For example, the hydrazinyl-indolyl or hydrazinyl-pyrrolo-pyridinyl coupling moieties may be modified to be attached (e.g., covalently attached) to a linker. As such, embodiments of the present disclosure include a hydrazinyl-indolyl or hydrazinyl-pyrrolo-pyridinyl coupling moiety attached to a drug or active agent through a linker. Various embodiments of the linker that may couple the hydrazinyl-indolyl or hydrazinyl-pyrrolo-pyridinyl coupling moiety to the drug or active agent are described in detail herein. For example, in some instances, the linker is a cleavable linker, such as a cleavable linker as described herein.

In certain embodiments, the polypeptide may be conjugated to a moiety of interest, where the polypeptide is modified before conjugation to the moiety of interest. Modification of the polypeptide may produce a modified polypeptide that contains one or more reactive groups suitable for conjugation to the moiety of interest. In some cases, the polypeptide may be modified at one or more amino acid residues to provide one or more reactive groups suitable for conjugation to the moiety of interest (e.g., a moiety that includes a coupling moiety, such as a hydrazinyl-indolyl or a hydrazinyl-pyrrolo-pyridinyl coupling moiety as described above). For example, the polypeptide may be modified to include a reactive aldehyde group (e.g., a reactive aldehyde). A reactive aldehyde may be included in an "aldehyde tag" or "ald-tag", which as used herein refers to an amino acid sequence derived from a sulfatase motif (e.g., L(C/S)TPSR) that has been converted by action of a formylglycine generating enzyme (FGE) to contain a 2-formylglycine residue (referred to herein as "FGly"). The FGly residue generated by an FGE may also be referred to as a "formylglycine". Stated differently, the term "aldehyde tag" is used herein to refer to an amino acid sequence that includes a "converted" sulfatase motif (i.e., a sulfatase motif in which a cysteine or serine residue has been converted to FGly by action of an FGE, e.g., L(FGly)TPSR). A converted sulfatase motif may be derived from an amino acid sequence that includes an "unconverted" sulfatase motif (i.e., a sulfatase motif in which the cysteine or serine residue has not been converted to FGly by an FGE, but is capable of being converted, e.g., an unconverted sulfatase motif with the sequence: L(C/S)TPSR). By "conversion" as used in the context of action of a formylglycine generating enzyme (FGE) on a sulfatase motif refers to biochemical modification of a cysteine or serine residue in a sulfatase motif to a formylglycine (FGly) residue (e.g., Cys to FGly, or Ser to FGly). Additional aspects of aldehyde tags and uses thereof in site-specific protein modification are described in U.S. Pat. Nos. 7,985,783 and 8,729,232, the disclosures of each of which are incorporated herein by reference.

In some cases, the modified polypeptide containing the FGly residue may be conjugated to the moiety of interest by reaction of the FGly with a compound (e.g., a compound containing a hydrazinyl-indolyl or a hydrazinyl-pyrrolo-pyridinyl coupling moiety, as described above). For example, an FGly-containing polypeptide may be contacted with a reactive partner-containing drug under conditions suitable to provide for conjugation of the drug to the polypeptide. In some instances, the reactive partner-containing drug may include a hydrazinyl-indolyl or a hydrazinyl-pyrrolo-pyridinyl coupling moiety as described above. For example, a drug or active agent may be modified to include a hydrazinyl-indolyl or a hydrazinyl-pyrrolo-pyridinyl coupling moiety. In some cases, the drug or active agent is attached to a hydrazinyl-indolyl or a hydrazinyl-pyrrolo-pyridinyl, such as covalently attached to a hydrazinyl-indolyl or a hydrazinyl-pyrrolo-pyridinyl through a linker, such as a cleavable linker as described in detail herein.

In certain embodiments, a conjugate of the present disclosure includes a polypeptide (e.g., an antibody) having at least one modified amino acid residue. The modified amino acid residue of the polypeptide may be coupled to a drug or active agent containing a hydrazinyl-indolyl or a hydrazinyl-pyrrolo-pyridinyl coupling moiety as described above. In certain embodiments, the modified amino acid residue of the polypeptide (e.g., antibody) may be derived from a cysteine or serine residue that has been converted to an FGly residue as described above. In certain embodiments, the FGly residue is conjugated to a drug or active agent containing a hydrazinyl-indolyl or a hydrazinyl-pyrrolo-pyridinyl coupling moiety as described above to provide a conjugate of the present disclosure where the drug or active agent is conjugated to the polypeptide through the hydrazinyl-indolyl or hydrazinyl-pyrrolo-pyridinyl coupling moiety. As used herein, the term FGly' refers to the modified amino acid residue of the polypeptide (e.g., antibody) that is coupled to the moiety of interest (e.g., a drug or active agent).

In certain embodiments, the conjugate includes at least one modified amino acid residue as described herein, where the modified amino acid residue is attached to a linker (cleavable linker) as described herein, which in turn is attached to a drug or active agent. For instance, the conjugate may include at least one modified amino acid residue (FGly') as described above. In some embodiments, the conjugate is of formula (I):

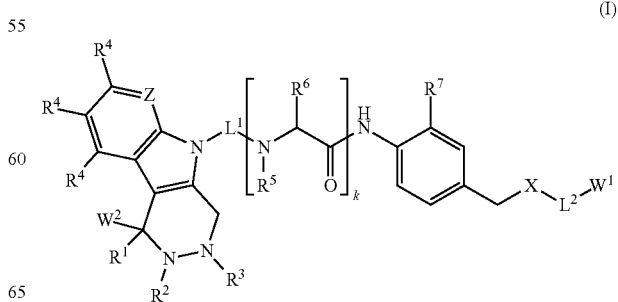

wherein

Z is CR⁴ or N;

X is O or NR⁴;

R¹ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

R² and R³ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or R² and R³ are optionally cyclically linked to form a 5 or 6-membered heterocyclyl;

each R⁴ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

each R⁵ is independently selected from hydrogen, alkyl, substituted alkyl, alkenyl, substituted alkenyl, alkynyl, and substituted alkynyl;

each R⁶ is independently selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

k is an integer from 1 to 10;

R⁷ comprises the second enzymatically cleavable moiety;

L¹ is a first linker;

L² is a second linker;

W¹ is the drug; and

W² is the antibody.

In certain embodiments of formula (I), k is 2, and the conjugate is of formula (Ia):

(Ia)

In certain embodiments of formula (I), the conjugate is of formula (Ib):

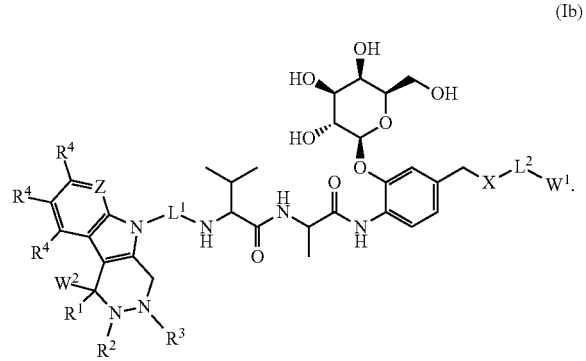

(Ib)

In certain embodiments of formula (I), the conjugate is of formula (Ic):

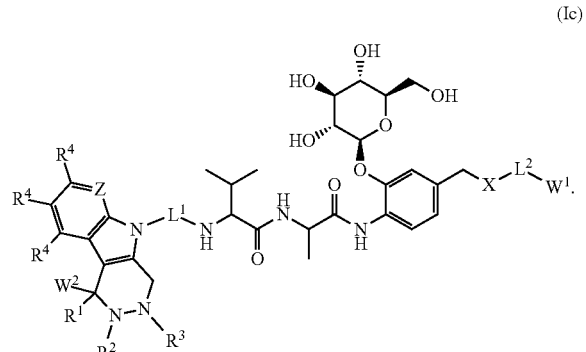

(Ic)

In certain embodiments of formula (I), the conjugate is of formula (Id):

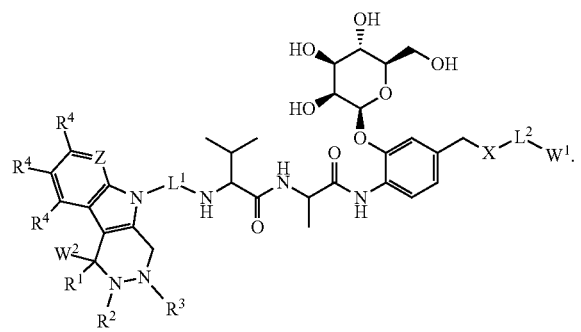

(Id)

In certain embodiments of formula (I), the conjugate is of formula (Ie):

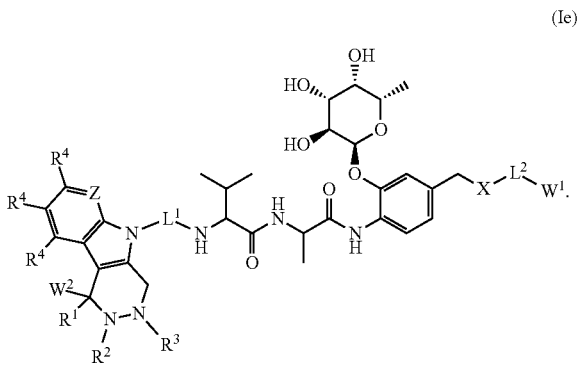

(Ie)

In certain embodiments of formula (I), the conjugate is of formula (If):

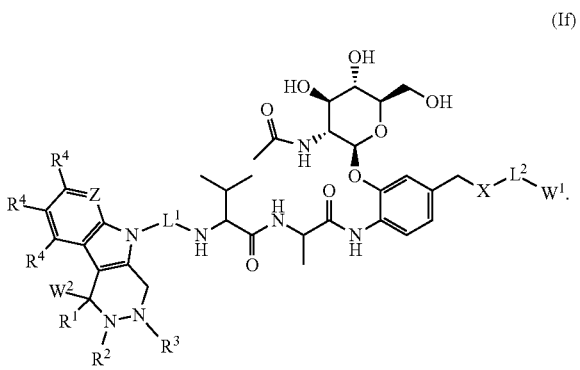

(If)

In certain embodiments of formula (I), the conjugate is of formula (Ig):

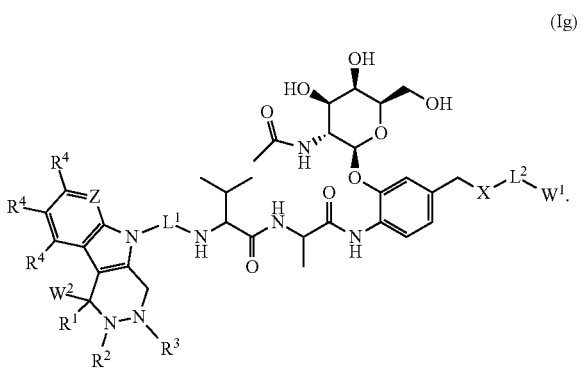

(Ig)

The substituents related to conjugates of formula (I) are described in more detail below. References to formula (I) are intended to also encompass formulae (Ia), (Ib), (Ic), (Id), (Je), (If) and (Ig).

In certain embodiments, Z is $CR^4$ or N. In certain embodiments, Z is $CR^4$. In certain embodiments, Z is N.

In certain embodiments, X is O or $NR^4$. In some instances, X is O. In some instances, X is $NR^4$. In some instances, X is NH.

In certain embodiments, $R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^1$ is hydrogen. In certain embodiments, $R^1$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^1$ is methyl. In certain embodiments, $R^1$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^1$ is alkynyl or substituted alkynyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^1$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^1$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^1$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-8}$ cycloalkyl or $C_{3-5}$ substituted cycloalkyl. In certain embodiments, $R^1$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl.

In certain embodiments, $R^2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^2$ is hydrogen. In certain embodiments, $R^2$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^2$ is methyl. In certain embodiments, $R^2$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^2$ is alkynyl or substituted alkynyl. In certain embodiments, $R^2$ is alkoxy or substituted alkoxy. In certain embodiments, $R^2$ is amino or substituted amino. In certain embodiments, $R^2$ is carboxyl or carboxyl ester. In certain embodiments, $R^2$ is acyl or acyloxy. In certain embodiments, $R^2$ is acyl amino or amino acyl. In certain embodiments, $R^2$ is alkylamide or substituted alkylamide. In certain embodiments, $R^2$ is sulfonyl. In certain embodiments, $R^2$ is thioalkoxy or substituted thioalkoxy. In certain embodiments, $R^2$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^2$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^2$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^2$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^3$ is hydrogen. In certain embodiments, $R^3$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^3$ is methyl. In certain embodiments, $R^3$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^3$ is alkynyl or substituted alkynyl. In certain embodiments, $R^3$ is alkoxy or substituted alkoxy. In certain embodiments, $R^3$ is amino or substituted amino. In certain embodiments, $R^3$ is carboxyl or carboxyl ester. In certain embodiments, $R^3$ is acyl or acyloxy. In certain embodiments, $R^3$ is acyl amino or amino acyl. In certain embodiments, $R^3$ is alkylamide or substituted alkylamide. In certain embodiments, $R^3$ is sulfonyl. In certain embodiments, $R^3$ is thioalkoxy or substituted thioalkoxy. In certain embodiments, $R^3$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^3$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^3$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^3$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^2$ and $R^3$ are optionally cyclically linked to form a 5 or 6-membered heterocyclyl. In certain embodiments, $R^2$ and $R^3$ are cyclically linked to form a 5 or 6-membered heterocyclyl. In certain embodiments, $R^2$ and $R^3$ are cyclically linked to form a 5-membered heterocyclyl. In certain embodiments, $R^2$ and $R^3$ are cyclically linked to form a 6-membered heterocyclyl.

In certain embodiments, each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

The various possibilities for each $R^4$ are described in more detail as follows. In certain embodiments, $R^4$ is hydrogen. In certain embodiments, each $R^4$ is hydrogen. In certain embodiments, $R^4$ is halogen, such as F, Cl, Br or I. In certain embodiments, $R^4$ is F. In certain embodiments, $R^4$ is Cl. In certain embodiments, $R^4$ is Br. In certain embodiments, $R^4$ is I. In certain embodiments, $R^4$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^4$ is methyl. In certain embodiments, $R^4$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^4$ is alkynyl or substituted alkynyl. In certain embodiments, $R^4$ is alkoxy or substituted alkoxy. In certain embodiments, $R^4$ is amino or substituted amino. In certain embodiments, $R^4$ is carboxyl or carboxyl ester. In certain embodiments, $R^4$ is acyl or acyloxy. In certain embodiments, $R^4$ is acyl amino or amino acyl. In certain embodiments, $R^4$ is alkylamide or substituted alkylamide. In certain embodiments, $R^4$ is sulfonyl. In certain embodiments, $R^4$ is thioalkoxy or substituted thioalkoxy. In certain embodiments, $R^4$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl (e.g., phenyl or substituted phenyl). In certain embodiments, $R^4$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^4$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^4$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, each $R^5$ is independently selected from hydrogen, alkyl, substituted alkyl, alkenyl, substituted alkenyl, alkynyl, and substituted alkynyl. In certain embodiments, $R^5$ is hydrogen. In certain embodiments, $R^5$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^5$ is methyl. In certain embodiments, $R^5$ is ethyl. In certain embodiments, $R^5$ is propyl (e.g., n-propyl or isopropyl). In certain embodiments, $R^5$ is butyl (e.g., n-butyl, isobutyl, sec-butyl, or t-butyl). In certain embodiments, $R^5$ is pentyl (e.g., n-pentyl or neopentyl, etc.). In certain embodiments, $R^5$ is neopentyl. In certain embodiments, $R^5$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^5$ is alkynyl or substituted alkynyl.

In certain embodiments, each $R^6$ is independently selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^6$ is hydrogen. In certain embodiments, $R^6$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^6$ is methyl. In certain embodiments, $R^6$ is ethyl. In certain embodiments, $R^6$ is propyl (e.g., n-propyl or isopropyl). In certain embodiments, $R^6$ is butyl (e.g., n-butyl, isobutyl, sec-butyl, or t-butyl). In certain embodiments, $R^6$ is pentyl (e.g., n-pentyl or neopentyl, etc.). In certain embodiments, $R^6$ is neopentyl. In certain embodiments, $R^6$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^6$ is alkynyl or substituted alkynyl.

In certain embodiments, $R^6$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl (e.g., phenyl or substituted phenyl). In certain embodiments, $R^6$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^6$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^6$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^6$ represents a side chain of an amino acid. For example, $R^6$ may represent the substituent attached to the α-carbon of an amino acid residue, including natural amino acids, unnatural amino acids, and amino acid analogs. In some cases, $R^6$ represents the side chain of an amino acid found in naturally occurring proteins (e.g., the side chain of Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). In certain embodiments, $R^6$ represents the side chain of valine (Val); i.e., $R^6$ is isopropyl. In certain embodiments, $R^6$ represents the side chain of alanine (Ala); i.e., $R^6$ is methyl. In certain embodiments, $R^6$ represents the side chain of phenylalanine (Phe); i.e., $R^6$ is benzyl. In certain embodiments, $R^6$ represents the side chain of lysine (Lys); i.e., $R^6$ is 4-amino-butyl.

In certain embodiments, k is an integer from 1 to 10. In certain embodiments, k is 1. In certain embodiments, k is 2. In certain embodiments, k is 3. In certain embodiments, k is 4. In certain embodiments, k is 5. In certain embodiments, k is 6. In certain embodiments, k is 7. In certain embodiments, k is 8. In certain embodiments, k is 9. In certain embodiments, k is 10.

In certain embodiment, the moiety in formula (I) enclosed by the brackets-subscript k denotes one or more amino acids (e.g., a peptide). For example, as described above, the conjugate of the present disclosure can include a first enzymatically cleavable moiety, where the a first enzymatically cleavable moiety is a peptide. As represented in formula (I), the one or more amino acids can be the peptide which comprises the first enzymatically cleavable moiety.

In certain embodiments, $R^7$ is the second enzymatically cleavable moiety as described herein. For example, $R^7$ may comprise a glycoside selected from a galactoside, a glucoside, a mannoside, a fucoside, O-GlcNAc and O-GalNAc. In some instances, $R^7$ comprises a galactoside. In some instances, $R^7$ comprises a glucoside. In some instances, $R^7$ comprises a mannoside. In some instances, $R^7$ comprises a fucoside. In some instances, $R^7$ comprises O-GlcNAc. In some instances, $R^7$ comprises O-GalNAc.

In certain embodiments, $L^1$ is a first linker. Linkers suitable for $L^1$ are described in more detail below.

In certain embodiments, $L^2$ is a second linker. Linkers suitable for $L^2$ are described in more detail below.

In certain embodiments, $W^1$ is a drug (or active agent). Further description of drugs and active agents suitable for use in the conjugates and compounds described herein is found in more detail below.

In certain embodiments, $W^2$ is an antibody. Further description of antibodies that find use in the subject conjugates is found in the disclosure herein.

In certain embodiments, the conjugate of formula (I) includes one or more linkers. The linker may be utilized to bind a coupling moiety to one or more moieties of interest and/or one or more polypeptides. In some embodiments, the linker binds a coupling moiety to either a polypeptide or a chemical entity such as a drug. The linker may be bound (e.g., covalently bonded) to the coupling moiety (e.g., as described herein) at any convenient position. For example, the linker may attach a hydrazinyl-indolyl or a hydrazinyl-pyrrolo-pyridinyl coupling moiety to a drug (e.g., a maytansine or an auristatin). The hydrazinyl-indolyl or hydrazinyl-pyrrolo-pyridinyl coupling moiety may be used to conjugate the linker (and thus the drug) to a polypeptide, such as an antibody. For example, the coupling moiety may be used to conjugate the linker (and thus the drug) to a modified amino acid residue of the polypeptide, such as an FGly reside of an antibody.

In certain embodiments, the linker includes one or more linkers, such as a first linker, $L^1$, and a second linker $L^2$. In addition, the linker may include one or more cleavable moieties (e.g., a first cleavable moiety and a second cleavable moiety), as described herein. In some cases, the linker includes one or more linkers, such as a first linker, $L^1$, and a second linker $L^2$. For example, the linker may include a first linker (L) that links the first cleavable moiety to a coupling moiety (e.g., a hydrazinyl-indolyl or hydrazinyl-pyrrolo-pyridinyl coupling moiety as described herein), and a second linker ($L^2$) that links the first cleavable moiety to a chemical entity, such as a drug or active agent as described herein. As such, the linker may include a first linker (L) that links the first cleavable moiety to an antibody (e.g., through a hydrazinyl-indolyl or hydrazinyl-pyrrolo-pyridinyl coupling moiety as described herein), and a second linker ($L^2$) that links the first cleavable moiety to a chemical entity, such as a drug or active agent as described herein.

For example, as shown in formula (I) above, $L^1$ is attached to $W^2$ through the coupling moiety, and thus $W^2$ is indirectly bonded to the first linker $L^1$ through the coupling moiety. As described above, $W^2$ is an antibody, and thus $L^1$ is attached through the coupling moiety to an antibody, e.g., the first linker $L^1$ is indirectly bonded to the antibody through the coupling moiety (e.g., through a hydrazinyl-indolyl or hydrazinyl-pyrrolo-pyridinyl coupling moiety as described herein). In addition, as shown in formula (I) above, $L^1$ is (indirectly) attached to $L^2$, and $L^2$ is attached to $W^1$. As described above, $W^1$ is a drug, and thus the second linker $L^2$ attaches the drug to the antibody $W^2$ through the first linker $L^1$ and the coupling moiety (e.g., a hydrazinyl-indolyl or hydrazinyl-pyrrolo-pyridinyl coupling moiety as described herein).

Any convenient linkers may be utilized for the first linker (L) and the second linker ($L^2$) in the subject conjugates and compounds. In certain embodiments, the first linker (L) and the second linker ($L^2$) each independently may include a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, the first linker (L) and the second linker ($L^2$) each independently may include an alkyl or substituted alkyl group. In certain embodiments, the first linker (L) and the second linker ($L^2$) each independently may include an alkenyl or substituted alkenyl group. In certain embodiments, the first linker (L) and the second linker ($L^2$) each independently may include an alkynyl or substituted alkynyl group. In certain embodiments, the first linker (L) and the second linker ($L^2$) each independently may include an alkoxy or substituted alkoxy group. In certain embodiments, the first linker (L) and the second linker ($L^2$) each independently may include an amino or substituted amino group. In certain embodiments, the first linker (L) and the second linker ($L^2$) each independently may include a carboxyl or carboxyl ester group. In certain embodiments, the first linker (L) and the second linker ($L^2$) each independently may include an acyl amino group. In certain embodiments, the first linker (L) and the second linker ($L^2$) each independently may include an alkylamide or substituted alkylamide group. In certain embodiments, the first linker ($L^1$) and the second linker ($L^2$) each independently may include an aryl or substituted aryl group. In certain embodiments, the first linker ($L^1$) and the second linker ($L^2$) each independently may include a heteroaryl or substituted heteroaryl group. In certain embodiments, the first linker ($L^1$) and the second linker ($L^2$) each independently may include a cycloalkyl or substituted cycloalkyl group. In certain embodiments, the first linker ($L^1$) and the second linker ($L^2$) each independently may include a heterocyclyl or substituted heterocyclyl group.

In certain embodiments, the first linker ($L^1$) and the second linker ($L^2$) each independently may include a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Other linkers are also possible, as shown in the conjugates and compounds described in more detail below.

In some embodiments, $L^1$ is a first linker described by the formula -$(L^{11})_a$-$(L^{12})_b$-$(L)_c$-$(L^{14})_d$-, wherein $L^{11}$, $L^{12}$, $L^{13}$ and $L^{14}$ are each independently a first linker subunit, and a, b, c and d are each independently 0 or 1, wherein the sum of a, b, c and d is 1 to 4.

In certain embodiments, the sum of a, b, c and d is 1. In certain embodiments, the sum of a, b, c and d is 2. In certain embodiments, the sum of a, b, c and d is 3. In certain embodiments, the sum of a, b, c and d is 4. In certain embodiments, a, b, c and d are each 1. In certain embodiments, a, b and c are each 1 and d is 0. In certain embodiments, a and b are each 1 and c and d are each 0. In certain embodiments, a is 1 and b, c and d are each 0.

In certain embodiments, $L^{11}$ is attached to the hydrazinyl-indolyl or the hydrazinyl-pyrrolo-pyridinyl coupling moiety (e.g., as shown in formula (I) above). In certain embodiments, $L^{12}$, if present, is attached to the first cleavable moiety. In certain embodiments, $L^{13}$, if present, is attached to the first cleavable moiety. In certain embodiments, $L^{14}$, if present, is attached to the first cleavable moiety.

Any convenient linker subunits may be utilized in the first linker $L^1$. Linker subunits of interest include, but are not limited to, units of polymers such as polyethylene glycols, polyethylenes and polyacrylates, amino acid residue(s), carbohydrate-based polymers or carbohydrate residues and derivatives thereof, polynucleotides, alkyl groups, aryl groups, heterocyclic groups, combinations thereof, and substituted versions thereof. In some embodiments, each of $L^{11}$, $L^{12}$, $L^{13}$ and $L^{14}$ (if present) comprise one or more groups independently selected from a polyethylene glycol, a modified polyethylene glycol, an amino acid residue, an alkyl group, a substituted alkyl, an aryl group, a substituted aryl group, and a diamine (e.g., a linking group that includes an alkylene diamine).

In some embodiments, $L^{11}$ (if present) comprises a polyethylene glycol, a modified polyethylene glycol, an amino acid residue, an alkyl group, a substituted alkyl, an aryl group, a substituted aryl group, or a diamine. In some embodiments, $L^{11}$ comprises a polyethylene glycol. In some embodiments, $L^{11}$ comprises a modified polyethylene glycol. In some embodiments, $L^{11}$ comprises an amino acid residue. In some embodiments, $L^{11}$ comprises an alkyl group or a substituted alkyl. In some embodiments, $L^{11}$ comprises an aryl group or a substituted aryl group. In some embodiments, $L^{11}$ comprises a diamine (e.g., a linking group comprising an alkylene diamine).

In some embodiments, $L^{12}$ (if present) comprises a polyethylene glycol, a modified polyethylene glycol, an amino acid residue, an alkyl group, a substituted alkyl, an aryl group, a substituted aryl group, or a diamine. In some embodiments, $L^{12}$ comprises a polyethylene glycol. In some embodiments, $L^{12}$ comprises a modified polyethylene glycol. In some embodiments, $L^{12}$ comprises an amino acid residue. In some embodiments, $L^{12}$ comprises an alkyl group or a substituted alkyl. In some embodiments, $L^{12}$ comprises an aryl group or a substituted aryl group. In some embodiments, $L^{12}$ comprises a diamine (e.g., a linking group comprising an alkylene diamine).

In some embodiments, $L^{13}$ (if present) comprises a polyethylene glycol, a modified polyethylene glycol, an amino acid residue, an alkyl group, a substituted alkyl, an aryl group, a substituted aryl group, or a diamine. In some embodiments, $L^{13}$ comprises a polyethylene glycol. In some embodiments, $L^{13}$ comprises a modified polyethylene glycol. In some embodiments, $L^{13}$ comprises an amino acid residue. In some embodiments, $L^{13}$ comprises an alkyl group or a substituted alkyl. In some embodiments, $L^{13}$ comprises an aryl group or a substituted aryl group. In some embodiments, $L^{13}$ comprises a diamine (e.g., a linking group comprising an alkylene diamine).

In some embodiments, $L^{14}$ (if present) comprises a polyethylene glycol, a modified polyethylene glycol, an amino acid residue, an alkyl group, a substituted alkyl, an aryl group, a substituted aryl group, or a diamine. In some embodiments, $L^{14}$ comprises a polyethylene glycol. In some embodiments, $L^{14}$ comprises a modified polyethylene glycol. In some embodiments, $L^{14}$ comprises an amino acid residue. In some embodiments, $L^{14}$ comprises an alkyl group or a substituted alkyl. In some embodiments, $L^{14}$ comprises an aryl group or a substituted aryl group. In some embodiments, $L^{14}$ comprises a diamine (e.g., a linking group comprising an alkylene diamine).

In some embodiments, $L^1$ is a first linker comprising $-(L^{11})_a-(L^{12})_b-(L^{13})_c-(L^{14})_d-$, where:

$-(L^{11})_a-$ is $-(T^1-V^1)_a-$;

$-(L^{12})_b-$ is $-(T^2-V^2)_b-$;

$-(L^{13})_c-$ is $-(T^3-V^3)_c-$; and $-(L^{14})_d-$ is $-(T^4-V^4)_d-$, wherein $T^1$, $T^2$, $T^3$ and $T^4$, if present, are tether groups; $V^1$, $V^2$, $V^3$ and $V^4$, if present, are covalent bonds or linking functional groups; and a, b, c and d are each independently 0 or 1, wherein the sum of a, b, c and d is 1 to 4.

As described above, in certain embodiments, $L^{11}$ is attached to the hydrazinyl-indolyl or the hydrazinyl-pyrrolo-pyridinyl coupling moiety (e.g., as shown in formula (I) above). As such, in certain embodiments, $T^1$ is attached to the hydrazinyl-indolyl or the hydrazinyl-pyrrolo-pyridinyl coupling moiety (e.g., as shown in formula (I) above). In certain embodiments, $V^1$ is attached to the first cleavable moiety. In certain embodiments, $L^{12}$, if present, is attached to the first cleavable moiety. As such, in certain embodiments, $T^2$, if present, is attached to the first cleavable moiety, or $V^2$, if present, is attached to the first cleavable moiety. In certain embodiments, $L^{13}$, if present, is attached to the first cleavable moiety. As such, in certain embodiments, $T^3$, if present, is attached to the first cleavable moiety, or $V^3$, if present, is attached to the first cleavable moiety. In certain embodiments, $L^{14}$, if present, is attached to the first cleavable moiety. As such, in certain embodiments, $T^4$, if present, is attached to the first cleavable moiety, or $V^4$, if present, is attached to the first cleavable moiety.

Regarding the tether groups, $T^1$, $T^2$, $T^3$ and $T^4$, any convenient tether groups may be utilized in the subject linkers. In some embodiments, $T^1$, $T^2$, $T^3$ and $T^4$ each comprise one or more groups independently selected from a $(C_1-C_{12})$alkyl, a substituted $(C_1-C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, $-(CR^{13}OH)_h-$, 4-amino-piperidine (4AP), an acetal group, a disulfide, a hydrazine, and an ester, where w is an integer from 1 to 20, n is an integer from 1 to 30, p is an integer from 1 to 20, and h is an integer from 1 to 12.

In certain embodiments, the tether group (e.g., $T^1$, $T^2$, $T^3$ and/or $T^4$) includes a $(C_1-C_{12})$alkyl or a substituted $(C_1-C_{12})$alkyl. In certain embodiments, $(C_1-C_{12})$alkyl is a straight chain or branched alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, $(C_1-C_{12})$alkyl may be an alkyl or substituted alkyl, such as $C_1-C_{12}$ alkyl, or $C_1-C_{10}$ alkyl, or $C_1-C_6$ alkyl, or $C_1-C_3$ alkyl. In some instances, $(C_1-C_{12})$alkyl is a $C_2$-alkyl. For example, $(C_1-C_{12})$alkyl may be an alkylene or substituted alkylene, such as $C_1-C_{12}$ alkylene, or $C_1-C_{10}$ alkylene, or $C_1-C_6$ alkylene, or $C_1-C_3$ alkylene. In some instances, $(C_1-C_{12})$alkyl is a $C_2$-alkylene (e.g., $CH_2CH_2$).

In certain embodiments, substituted $(C_1-C_{12})$alkyl is a straight chain or branched substituted alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, substituted $(C_1-C_{12})$alkyl may be a substituted alkyl, such as substituted $C_1-C_{12}$ alkyl, or substituted $C_1-C_{10}$ alkyl, or substituted $C_1-C_6$ alkyl, or substituted $C_1-C_3$ alkyl. In some instances, substituted $(C_1-C_{12})$alkyl is a substituted $C_2$-alkyl. For example, substituted $(C_1-C_{12})$alkyl may be a substituted alkylene, such as substituted $C_1-C_{12}$ alkylene, or substituted $C_1-C_{10}$ alkylene, or substituted $C_1-C_6$ alkylene, or substituted $C_1-C_3$ alkylene. In some instances, substituted $(C_1-C_{12})$alkyl is a substituted $C_2$-alkylene.

In certain embodiments, the tether group (e.g., $T^1$, $T^2$, $T^3$ and/or $T^4$) includes an aryl, substituted aryl, heteroaryl, substituted heteroaryl, cycloalkyl, substituted cycloalkyl, heterocyclyl, or substituted heterocyclyl. In some instances, the tether group (e.g., $T^1$, $T^2$, $T^3$ and/or $T^4$) includes an aryl or substituted aryl. For example, the aryl can be phenyl. In some cases, the substituted aryl is a substituted phenyl. The substituted phenyl can be substituted with one or more substituents selected from $(C_1-C_{12})$alkyl, a substituted $(C_1-C_{12})$alkyl, aryl, substituted aryl, heteroaryl, substituted heteroaryl, cycloalkyl, substituted cycloalkyl, heterocyclyl, and substituted heterocyclyl. In some instances, the substituted aryl is a substituted phenyl, where the substituent includes a second cleavable moiety as described herein (e.g., an enzymatically cleavable moiety, such as a glycoside).

In some instances, the tether group (e.g., $T^1$, $T^2$, $T^3$ and/or $T^4$) includes a heteroaryl or substituted heteroaryl. In some instances, the tether group (e.g., $T^1$, $T^2$, $T^3$ and/or $T^4$) includes a cycloalkyl or substituted cycloalkyl. In some instances, the tether group (e.g., $T^1$, $T^2$, $T^3$ and/or $T^4$) includes a heterocyclyl or substituted heterocyclyl. In some instances, the substituent on the substituted heteroaryl, substituted cycloalkyl or substituted heterocyclyl includes a second cleavable moiety as described herein (e.g., an enzymatically cleavable moiety, such as a glycoside).

In certain embodiments, the tether group (e.g., $T^1$, $T^2$, $T^3$ and/or $T^4$) includes an ethylene diamine (EDA) moiety, e.g., an EDA containing tether. In certain embodiments, $(EDA)_w$ includes one or more EDA moieties, such as where w is an integer from 1 to 50, such as from 1 to 40, from 1 to 30, from 1 to 20, from 1 to 12 or from 1 to 6, such as 1, 2, 3, 4, 5 or 6). The linked ethylene diamine (EDA) moieties may optionally be substituted at one or more convenient positions with any convenient substituents, e.g., with an alkyl, a substituted alkyl, an acyl, a substituted acyl, an aryl or a substituted aryl. In certain embodiments, the EDA moiety is described by the structure:

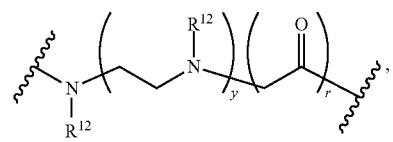

where y is an integer from 1 to 6, or is 0 or 1, and each $R^{12}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, y is 1, 2, 3, 4, 5 or 6. In certain embodiments, y is 1 and r is 0. In certain embodiments, y is 1 and r is 1. In certain embodiments, y is 2 and r is 0. In certain embodiments, y is 2 and r is 1. In certain embodiments, each $R^{12}$ is independently selected from hydrogen, an alkyl, a substituted alkyl, an aryl and a substituted aryl. In certain embodiments, any two adjacent $R^{12}$ groups of the EDA may be cyclically linked, e.g., to form a piperazinyl ring. In certain embodiments, y is 1 and the two adjacent $R^{12}$ groups are an alkyl group, cyclically linked to form a piperazinyl ring. In certain embodiments, y is 1 and the adjacent $R^{12}$ groups are selected from hydrogen, an alkyl (e.g., methyl) and a substituted alkyl (e.g., lower alkyl-OH, such as ethyl-OH or propyl-OH).

In certain embodiments, the tether group (e.g., $T^1$, $T^2$, $T^3$ and/or $T^4$) includes a 4-amino-piperidine (4AP) moiety (also referred to herein as piperidin-4-amino, P4A). The 4AP moiety may optionally be substituted at one or more convenient positions with any convenient substituents, e.g., with an alkyl, a substituted alkyl, a polyethylene glycol moiety, an acyl, a substituted acyl, an aryl or a substituted aryl. In certain embodiments, the 4AP moiety is described by the structure:

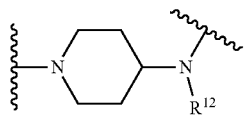

where $R^{12}$ is selected from hydrogen, alkyl, substituted alkyl, a polyethylene glycol moiety (e.g., a polyethylene glycol or a modified polyethylene glycol), alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{12}$ is a polyethylene glycol moiety. In certain embodiments, $R^{12}$ is a carboxy modified polyethylene glycol.

In certain embodiments, $R^{12}$ includes a polyethylene glycol moiety described by the formula: $(PEG)_k$, which may be represented by the structure:

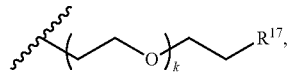

where k is an integer from 1 to 20, such as from 1 to 18, or from 1 to 16, or from 1 to 14, or from 1 to 12, or from 1 to 10, or from 1 to 8, or from 1 to 6, or from 1 to 4, or 1 or 2, such as 1, 2, 3, 4, 5, 6, 7, 8, 9, 10, 11, 12, 13, 14, 15, 16, 17, 18, 19 or 20. In some instances, k is 2. In certain embodiments, $R^{17}$ is selected from OH, COOH, or COOR, where R is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^{17}$ is COOH.

In certain embodiments, a tether group (e.g., $T^1$, $T^2$, $T^3$ and/or $T^4$) includes $(PEG)_n$, where $(PEG)_n$ is a polyethylene glycol or a modified polyethylene glycol linking unit. In certain embodiments, $(PEG)_n$ is described by the structure:

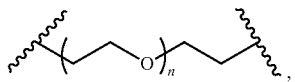

where n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In some instances, n is 2. In some instances, n is 3. In some instances, n is 6. In some instances, n is 12.

In certain embodiments, a tether group (e.g., $T^1$, $T^2$, $T^3$ and/or $T^4$) includes $(AA)_p$, where AA is an amino acid residue. Any convenient amino acids may be utilized. Amino acids of interest include but are not limited to, L- and D-amino acids, naturally occurring amino acids such as any of the 20 primary alpha-amino acids and beta-alanine, non-naturally occurring amino acids (e.g., amino acid analogs), such as a non-naturally occurring alpha-amino acid or a non-naturally occurring beta-amino acid, etc. In certain embodiments, p is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In certain embodiments, p is 1. In certain embodiments, p is 2.

In certain embodiments, a tether group (e.g., $T^1$, $T^2$, $T^3$ and/or $T^4$) includes a moiety described by the formula $-(CR^{13}OH)_h-$, where h is 0 or n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11 or 12. In certain embodiments, h is 1. In certain embodiments, h is 2. In certain embodiments, $R^{13}$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{13}$ is hydrogen. In certain embodiments, $R^{13}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{13}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{13}$ is alkynyl or substituted alkynyl. In certain embodiments, $R^{13}$ is alkoxy or substituted alkoxy. In certain embodiments, $R^{13}$ is amino or substituted amino. In certain embodiments, $R^{13}$ is carboxyl or carboxyl ester. In certain embodiments, $R^{13}$ is acyl or acyloxy. In certain embodiments, $R^{13}$ is acyl amino or amino acyl. In certain embodiments, $R^{13}$ is alkylamide or substituted alkylamide. In certain embodiments, $R^{13}$ is sulfonyl. In certain embodiments, $R^{13}$ is thioalkoxy or substituted thioalkoxy. In certain embodiments, $R^{13}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{13}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{13}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{13}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^{13}$ is selected from hydrogen, an alkyl, a substituted alkyl, an aryl, and a substituted aryl. In these embodiments, alkyl, substituted alkyl, aryl, and substituted aryl are as described above for $R^{13}$.

Regarding the linking functional groups, $V^1$, $V^2$, $V^3$ and $V^4$, any convenient linking functional groups may be utilized in the first linker $L^1$. Linking functional groups of interest include, but are not limited to, amino, carbonyl, amido, oxycarbonyl, carboxy, sulfonyl, sulfoxide, sulfonylamino, aminosulfonyl, thio, oxy, phospho, phosphoramidate, thiophosphoraidate, and the like. In some embodiments, $V^1$, $V^2$, $V^3$ and $V^4$ are each independently selected from a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, where q is an integer from 1 to 6. In certain embodiments, q is an integer from 1 to 6 (e.g., 1, 2, 3, 4, 5 or 6). In certain embodiments, q is 1. In certain embodiments, q is 2.

In some embodiments, each $R^{15}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

The various possibilities for each $R^{15}$ are described in more detail as follows. In certain embodiments, $R^{15}$ is hydrogen. In certain embodiments, each $R^{15}$ is hydrogen. In certain embodiments, $R^{15}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{15}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{15}$ is alkynyl or substituted alkynyl. In certain embodiments, $R^{15}$ is alkoxy or substituted alkoxy. In certain embodiments, $R^{15}$ is amino or substituted amino. In certain embodiments, $R^{15}$ is carboxyl or carboxyl ester. In certain embodiments, $R^{15}$ is acyl or acyloxy. In certain embodiments, $R^{15}$ is acyl amino or amino acyl. In certain embodiments, $R^{15}$ is alkylamide or substituted alkylamide. In certain embodiments, $R^{15}$ is sulfonyl. In certain embodiments, $R^{15}$ is thioalkoxy or substituted thioalkoxy. In certain embodiments, $R^{15}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{15}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{15}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{15}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl. In these embodiments, the hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl substituents are as described above for $R^{15}$.

In certain embodiments, the tether group includes an acetal group, a disulfide, a hydrazine, or an ester. In some embodiments, the tether group includes an acetal group. In some embodiments, the tether group includes a disulfide. In some embodiments, the tether group includes a hydrazine. In some embodiments, the tether group includes an ester.

As described above, in some embodiments, $L^1$ is a first linker comprising -($T^1$-$V^1$)$_a$-($T^2$-$V^2$)$_b$-($T^3$-$V^3$)$_c$-($T^4$-$V^4$)$_d$—, where a, b, c and d are each independently 0 or 1, where the sum of a, b, c and d is 1 to 4.

In some embodiments, in the first linker $L^1$:
$T^1$ is selected from a $(C_1$-$C_{12})$alkyl and a substituted $(C_1$-$C_{12})$alkyl;
$T^2$, $T^3$ and $T^4$ are each independently selected from $(C_1$-$C_{12})$alkyl, substituted $(C_1$-$C_{12})$alkyl, aryl, substituted aryl, heteroaryl, substituted heteroaryl, cycloalkyl, substituted cycloalkyl, heterocyclyl, and substituted heterocyclyl, (EDA)$_w$, (PEG)$_n$, (AA)$_p$, —(CR$^{13}$OH)$_h$—, 4-amino-piperidine (4AP), an acetal group, a disulfide, a hydrazine, and an ester; and
$V^1$, $V^2$, $V^3$ and $V^4$ are each independently selected from a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein q is an integer from 1 to 6;
wherein:
(PEG)$_n$ is

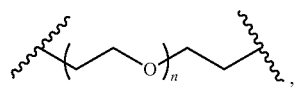

where n is an integer from 1 to 30;
EDA is an ethylene diamine moiety having the following structure:

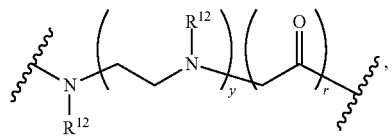

where y is an integer from 1 to 6 and r is 0 or 1;
4-amino-piperidine (4AP) is

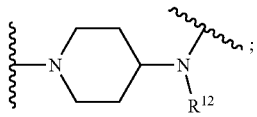

AA is an amino acid residue, where p is an integer from 1 to 20; and each $R^{15}$ and $R^{12}$ is independently selected from hydrogen, an alkyl, a substituted alkyl, an aryl and a substituted aryl, wherein any two adjacent $R^{12}$ groups may be cyclically linked to form a piperazinyl ring; and $R^{13}$ is selected from hydrogen, an alkyl, a substituted alkyl, an aryl, and a substituted aryl.

In certain embodiments, $T^1$, $T^2$, $T^3$ and $T^4$ and $V^1$, $V^2$, $V^3$ and $V^4$ are selected from the following:

$T^1$ is $(C_1\text{-}C_{12})$alkyl and $V^1$ is —CO—;

$T^2$ is an amino acid analog and $V^2$ is —NH—;

$T^3$ is $(PEG)_n$ and $V^3$ is —CO—; and d is 0 (i.e., $T^4$ and $V^4$ are not present).

In certain embodiments, the left-hand side of the above linker structures is attached to the hydrazinyl-indolyl or the hydrazinyl-pyrrolo-pyridinyl coupling moiety, and the right-hand side of the above linker structures is attached to the first cleavable moiety. For example, in cases where the first cleavable moiety includes a peptide, the right-hand side of the above linker structures can be attached to an amino acid of the peptide that comprises the first cleavable moiety. In some instances, the carbonyl group on the right-hand side of the above linker structures can form an amide bond with an amino acid of the peptide that comprises the first cleavable moiety.

In some embodiments, $L^2$ is a second linker described by the formula -$(L^{21})_e$-$(L^{22})_f$-$(L^{23})_g$-$(L^{24})_h$-, wherein $L^{21}$, $L^{22}$, $L^{23}$ and $L^{24}$ are each independently a second linker subunit, and e, f, g and h are each independently 0 or 1, wherein the sum of e, f, g and h is 0 to 4.

In certain embodiments, the sum of e, f, g and h is 0. In these instances, the second linker $L^2$ is not present. Stated another way, when the sum of e, f, g and h is 0, then the second linker $L^2$ is a covalent bond. In certain embodiments, the sum of e, f, g and h is 1. In certain embodiments, the sum of e, f, g and h is 2. In certain embodiments, the sum of e, f, g and h is 3. In certain embodiments, the sum of e, f, g and h is 4. In certain embodiments, e, f, g and h are each 1. In certain embodiments, e, f and g are each 1 and h is 0. In certain embodiments, e and f are each 1 and g and h are each 0. In certain embodiments, e is 1 and f, g and h are each 0.

In certain embodiments, $L^{21}$ is attached to the drug (e.g., $W^1$ as shown in formula (I) above). In certain embodiments, $L^{22}$, if present, is attached to the drug. In certain embodiments, $L^{23}$, if present, is attached to the drug. In certain embodiments, $L^{24}$, if present, is attached to the drug.

Any convenient linker subunits may be utilized in the second linker $L^2$. Linker subunits of interest include, but are not limited to, units of polymers such as polyethylene glycols, polyethylenes and polyacrylates, amino acid residue(s), carbohydrate-based polymers or carbohydrate residues and derivatives thereof, polynucleotides, alkyl groups, aryl groups, heterocyclic groups, combinations thereof, and substituted versions thereof. In some embodiments, each of $L^{21}$, $L^{22}$, $L^{23}$ and $L^{24}$ (if present) comprise one or more groups independently selected from a polyethylene glycol, a modified polyethylene glycol, an amino acid residue, an alkyl group, a substituted alkyl, an aryl group, a substituted aryl group, and a diamine (e.g., a linking group that includes an alkylene diamine).

In some embodiments, $L^{21}$ (if present) comprises a polyethylene glycol, a modified polyethylene glycol, an amino acid residue, an alkyl group, a substituted alkyl, an aryl group, a substituted aryl group, or a diamine. In some embodiments, $L^{21}$ comprises a polyethylene glycol. In some embodiments, $L^{21}$ comprises a modified polyethylene glycol. In some embodiments, $L^{21}$ comprises an amino acid residue. In some embodiments, $L^{21}$ comprises an alkyl group or a substituted alkyl. In some embodiments, $L^{21}$ comprises an aryl group or a substituted aryl group. In some embodiments, $L^{21}$ comprises a diamine (e.g., a linking group comprising an alkylene diamine).

In some embodiments, $L^{22}$ (if present) comprises a polyethylene glycol, a modified polyethylene glycol, an amino acid residue, an alkyl group, a substituted alkyl, an aryl group, a substituted aryl group, or a diamine. In some embodiments, $L^{22}$ comprises a polyethylene glycol. In some embodiments, $L^{22}$ comprises a modified polyethylene glycol. In some embodiments, $L^{22}$ comprises an amino acid residue. In some embodiments, $L^{22}$ comprises an alkyl group or a substituted alkyl. In some embodiments, $L^{22}$ comprises an aryl group or a substituted aryl group. In some embodiments, $L^{22}$ comprises a diamine (e.g., a linking group comprising an alkylene diamine).

In some embodiments, $L^{23}$ (if present) comprises a polyethylene glycol, a modified polyethylene glycol, an amino acid residue, an alkyl group, a substituted alkyl, an aryl group, a substituted aryl group, or a diamine. In some embodiments, $L^{23}$ comprises a polyethylene glycol. In some embodiments, $L^{23}$ comprises a modified polyethylene glycol. In some embodiments, $L^{23}$ comprises an amino acid residue. In some embodiments, $L^{23}$ comprises an alkyl group or a substituted alkyl. In some embodiments, $L^{23}$ comprises an aryl group or a substituted aryl group. In some embodiments, $L^{23}$ comprises a diamine (e.g., a linking group comprising an alkylene diamine).

In some embodiments, $L^{24}$ (if present) comprises a polyethylene glycol, a modified polyethylene glycol, an amino acid residue, an alkyl group, a substituted alkyl, an aryl group, a substituted aryl group, or a diamine. In some embodiments, $L^{24}$ comprises a polyethylene glycol. In some embodiments, $L^{24}$ comprises a modified polyethylene glycol. In some embodiments, $L^{24}$ comprises an amino acid residue. In some embodiments, $L^{24}$ comprises an alkyl group or a substituted alkyl. In some embodiments, $L^{24}$ comprises an aryl group or a substituted aryl group. In some embodiments, $L^{24}$ comprises a diamine (e.g., a linking group comprising an alkylene diamine).

In some embodiments, $L^2$ is a second linker comprising -$(L^{21})_e$-$(L^{22})_f$-$(L^{23})_g$-$(L^{24})_h$-, where:

-$(L^{21})_e$- is -$(T^1\text{-}V^5)_e$-;

-$(L^{22})_f$- is -$(T^6\text{-}V^6)_f$-;

-$(L^{23})_g$- is -$(T^7\text{-}V^7)_g$-; and

-$(L^{24})_h$- is -$(T^8\text{-}V^8)_h$-, wherein $T^5$, $T^6$, $T^7$ and $T^8$, if present, are tether groups; $V^5$, $V^6$, $V^7$ and $V^8$, if present, are covalent bonds or linking functional groups; and e, f, g and h are each independently 0 or 1, wherein the sum of e, f, g and h is 0 to 4.

In certain embodiments, $L^{21}$ is attached to the first cleavable moiety. As such, in certain embodiments, $T^5$ is attached to the first cleavable moiety. In certain embodiments, $V^5$ is attached to the drug (e.g., $W^1$ as shown in formula (I) above). In certain embodiments, $L^{22}$, if present, is attached to the drug. As such, in certain embodiments, $T^6$, if present, is attached to the drug, or $V^6$, if present, is attached to the drug. In certain embodiments, $L^{23}$, if present, is attached to the drug. As such, in certain embodiments, $T^7$, if present, is attached to the drug, or $V^7$, if present, is attached to the drug.

In certain embodiments, $L^{24}$, if present, is attached to the drug. As such, in certain embodiments, $T^8$, if present, is attached to the drug, or $V^8$, if present, is attached to the drug.

Regarding the tether groups, $T^5$, $T^6$, $T^7$ and $T^8$, any convenient tether groups may be utilized in the subject linkers. In some embodiments, $T^5$, $T^6$, $T^7$ and $T^8$ each comprise one or more groups independently selected from a $(C_1-C_{12})$alkyl, a substituted $(C_1-C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, —$(CR^{13}OH)_h$—, 4-amino-piperidine (4AP), an acetal group, a disulfide, a hydrazine, and an ester, where w is an integer from 1 to 20, n is an integer from 1 to 30, p is an integer from 1 to 20, and h is an integer from 1 to 12.

In certain embodiments, the tether group (e.g., $T^5$, $T^6$, $T^7$ and/or $T^8$) includes a $(C_1-C_{12})$alkyl or a substituted $(C_1-C_{12})$alkyl. In certain embodiments, $(C_1-C_{12})$alkyl is a straight chain or branched alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, $(C_1-C_{12})$alkyl may be an alkyl or substituted alkyl, such as $C_1-C_{12}$ alkyl, or $C_1-C_{10}$ alkyl, or $C_1-C_6$ alkyl, or $C_1-C_3$ alkyl. In some instances, $(C_1-C_{12})$alkyl is a $C_2$-alkyl. For example, $(C_1-C_{12})$alkyl may be an alkylene or substituted alkylene, such as $C_1-C_{12}$ alkylene, or $C_1-C_{10}$ alkylene, or $C_1-C_6$ alkylene, or $C_1-C_3$ alkylene. In some instances, $(C_1-C_{12})$alkyl is a $C_2$-alkylene (e.g., $CH_2CH_2$). In some instances, $(C_1-C_{12})$alkyl is a $C_1$-alkylene (e.g., $CH_2$).

In certain embodiments, substituted $(C_1-C_{12})$alkyl is a straight chain or branched substituted alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, substituted $(C_1-C_{12})$alkyl may be a substituted alkyl, such as substituted $C_1-C_{12}$ alkyl, or substituted $C_1-C_{10}$ alkyl, or substituted $C_1-C_6$ alkyl, or substituted $C_1-C_3$ alkyl. In some instances, substituted $(C_1-C_{12})$alkyl is a substituted $C_2$-alkyl. For example, substituted $(C_1-C_{12})$alkyl may be a substituted alkylene, such as substituted $C_1-C_{12}$ alkylene, or substituted $C_1-C_{10}$ alkylene, or substituted $C_1-C_6$ alkylene, or substituted $C_1-C_3$ alkylene. In some instances, substituted $(C_1-C_{12})$alkyl is a substituted $C_2$-alkylene. In some instances, substituted $(C_1-C_{12})$alkyl is a substituted $C_1$-alkylene.

In certain embodiments, the tether group (e.g., $T^5$, $T^6$, $T^7$ and/or $T^8$) includes an aryl, substituted aryl, heteroaryl, substituted heteroaryl, cycloalkyl, substituted cycloalkyl, heterocyclyl, or substituted heterocyclyl. In some instances, the tether group includes an aryl or substituted aryl. For example, the aryl can be phenyl or substituted phenyl. In some instances, the tether group (e.g., $T^5$, $T^6$, $T^7$ and/or $T^8$) includes a heteroaryl or substituted heteroaryl. In some instances, the tether group (e.g., $T^5$, $T^6$, $T^7$ and/or $T^8$) includes a cycloalkyl or substituted cycloalkyl. In some instances, the tether group (e.g., $T^5$, $T^6$, $T^7$ and/or $T^8$) includes a heterocyclyl or substituted heterocyclyl.

In certain embodiments, the tether group (e.g., $T^5$, $T^6$, $T^7$ and/or $T^8$) includes an ethylene diamine (EDA) moiety, e.g., an EDA moiety as described above, such as an EDA moiety described by the structure:

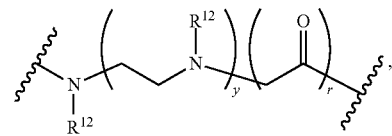

where y is an integer from 1 to 6, or is 0 or 1, and each $R^{12}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, y is 1, 2, 3, 4, 5 or 6. In certain embodiments, y is 1 and r is 0. In certain embodiments, y is 1 and r is 1. In certain embodiments, y is 2 and r is 0. In certain embodiments, y is 2 and r is 1. In certain embodiments, each $R^{12}$ is independently selected from hydrogen, an alkyl, a substituted alkyl, an aryl and a substituted aryl. In certain embodiments, any two adjacent $R^{12}$ groups of the EDA may be cyclically linked, e.g., to form a piperazinyl ring. In certain embodiments, y is 1 and the two adjacent $R^{12}$ groups are an alkyl group, cyclically linked to form a piperazinyl ring. In certain embodiments, y is 1 and the adjacent $R^{12}$ groups are selected from hydrogen, an alkyl (e.g., methyl) and a substituted alkyl (e.g., lower alkyl-OH, such as ethyl-OH or propyl-OH).

In certain embodiments, the tether group (e.g., $T^5$, $T^6$, $T^7$ and/or $T^8$) includes a 4-amino-piperidine (4AP) moiety as described above, such as a 4AP moiety described by the structure:

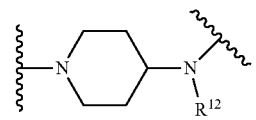

where $R^{12}$ is selected from hydrogen, alkyl, substituted alkyl, a polyethylene glycol moiety (e.g., a polyethylene glycol or a modified polyethylene glycol), alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{12}$ is a polyethylene glycol moiety. In certain embodiments, $R^{12}$ is a carboxy modified polyethylene glycol.

In certain embodiments, $R^{12}$ includes a polyethylene glycol moiety described by the formula: $(PEG)_k$, which may be represented by the structure:

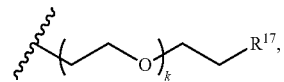

where k is an integer from 1 to 20, such as from 1 to 18, or from 1 to 16, or from 1 to 14, or from 1 to 12, or from 1 to 10, or from 1 to 8, or from 1 to 6, or from 1 to 4, or 1 or 2, such as 1, 2, 3, 4, 5, 6, 7, 8, 9, 10, 11, 12, 13, 14, 15, 16, 17, 18, 19 or 20. In some instances, k is 2. In certain embodiments, $R^{17}$ is selected from OH, COOH, or COOR, where R is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^{17}$ is COOH.

In certain embodiments, a tether group (e.g., $T^5$, $T^6$, $T^7$ and/or $T^8$) includes a polyethylene glycol moiety $(PEG)_n$ as described above, such as a $(PEG)_n$ moiety described by the structure:

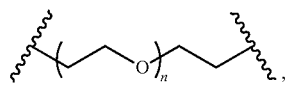

where n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In some instances, n is 2. In some instances, n is 3. In some instances, n is 6. In some instances, n is 12.

In certain embodiments, a tether group (e.g., $T^5$, $T^6$, $T^7$ and/or $T^8$) includes $(AA)_p$, where AA is an amino acid residue. Any convenient amino acids may be utilized. Amino acids of interest include but are not limited to, L- and D-amino acids, naturally occurring amino acids such as any of the 20 primary alpha-amino acids and beta-alanine, non-naturally occurring amino acids (e.g., amino acid analogs), such as a non-naturally occurring alpha-amino acid or a non-naturally occurring beta-amino acid, etc. In certain embodiments, p is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In certain embodiments, p is 1. In certain embodiments, p is 2.

In certain embodiments, a tether group (e.g., $T^5$, $T^6$, $T^7$ and/or $T^8$) includes a moiety described by the formula $-(CR^{13}OH)_h-$, where h is 0 or n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11 or 12. In certain embodiments, h is 1. In certain embodiments, h is 2. In certain embodiments, $R^{13}$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{13}$ is hydrogen. In certain embodiments, $R^{13}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{13}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{13}$ is alkynyl or substituted alkynyl. In certain embodiments, $R^{13}$ is alkoxy or substituted alkoxy. In certain embodiments, $R^{13}$ is amino or substituted amino. In certain embodiments, $R^{13}$ is carboxyl or carboxyl ester. In certain embodiments, $R^{13}$ is acyl or acyloxy. In certain embodiments, $R^{13}$ is acyl amino or amino acyl. In certain embodiments, $R^{13}$ is alkylamide or substituted alkylamide. In certain embodiments, $R^{13}$ is sulfonyl. In certain embodiments, $R^{13}$ is thioalkoxy or substituted thioalkoxy. In certain embodiments, $R^{13}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{13}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{13}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{13}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^{13}$ is selected from hydrogen, an alkyl, a substituted alkyl, an aryl, and a substituted aryl. In these embodiments, alkyl, substituted alkyl, aryl, and substituted aryl are as described above for $R^{13}$.

Regarding the linking functional groups, $V^5$, $V^6$, $V^7$ and $V^8$, any convenient linker functional groups may be utilized in the second linker $L^2$. Linking functional groups of interest include, but are not limited to, amino, carbonyl, amido, oxycarbonyl, carboxy, sulfonyl, sulfoxide, sulfonylamino, aminosulfonyl, thio, oxy, phospho, phosphoramidate, thiophosphoraidate, and the like. In some embodiments, $V^5$, $V^6$, $V^7$ and $V^8$ are each independently selected from a covalent bond, $-CO-$, $-NR^{15}-$, $-NR^{15}(CH_2)_q-$, $-NR^{15}(C_6H_4)-$, $-CONR^{15}-$, $-NR^{15}CO-$, $-C(O)O-$, $-OC(O)-$, $-O-$, $-S-$, $-S(O)-$, $-SO_2-$, $-SO_2NR^{15}-$, $-NR^{15}SO_2-$ and $-P(O)OH-$, where q is an integer from 1 to 6. In certain embodiments, q is an integer from 1 to 6 (e.g., 1, 2, 3, 4, 5 or 6). In certain embodiments, q is 1. In certain embodiments, q is 2.

In some embodiments, each $R^{15}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

The various possibilities for each $R^{15}$ are described in more detail as follows. In certain embodiments, $R^{15}$ is hydrogen. In certain embodiments, each $R^{15}$ is hydrogen. In certain embodiments, $R^{15}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{15}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{15}$ is alkynyl or substituted alkynyl. In certain embodiments, $R^{15}$ is alkoxy or substituted alkoxy. In certain embodiments, $R^{15}$ is amino or substituted amino. In certain embodiments, $R^{15}$ is carboxyl or carboxyl ester. In certain embodiments, $R^{15}$ is acyl or acyloxy. In certain embodiments, $R^{15}$ is acyl amino or amino acyl. In certain embodiments, $R^{15}$ is alkylamide or substituted alkylamide. In certain embodiments, $R^{15}$ is sulfonyl. In certain embodiments, $R^{15}$ is thioalkoxy or substituted thioalkoxy. In certain embodiments, $R^{15}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{15}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{15}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{15}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl. In these embodiments, the hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl substituents are as described above for $R^{15}$.

In certain embodiments, the tether group includes an acetal group, a disulfide, a hydrazine, or an ester. In some embodiments, the tether group includes an acetal group. In some embodiments, the tether group includes a disulfide. In some embodiments, the tether group includes a hydrazine. In some embodiments, the tether group includes an ester.

As described above, in some embodiments, $L^2$ is a second linker comprising $-(T^5-V^5)_e-(T^6-V^6)_f-(T^7-V^7)_g-(T^8-V^8)_h-$, where e, f, g and h are each independently 0 or 1, where the sum of e, f, g and h is 0 to 4.

In some embodiments, in the second linker $L^2$:

$T^5$, $T^6$, $T^7$ and $T^8$ are each independently selected from $(C_1-C_{12})$alkyl, substituted $(C_1-C_{12})$alkyl, aryl, substituted aryl, heteroaryl, substituted heteroaryl, cycloalkyl, substituted cycloalkyl, heterocyclyl, or substituted heterocyclyl, $(EDA)_w$, $(PEG)_n$, $(AA)_p$, $-(CR^{13}OH)_h-$, 4-amino-piperidine (4AP), an acetal group, a disulfide, a hydrazine, and an ester; and $V^5$, $V^6$, $V^7$ and $V^8$ are each independently selected from a covalent bond, $-CO-$, $-NR^{15}-$, $-NR^{15}(CH_2)_q-$, $-NR^{15}(C_6H_4)-$, $-CONR^{15}-$, $-NR^{15}CO-$, $-C(O)O-$, $-OC(O)-$, $-O-$, $-S-$, $-S(O)-$, $-SO_2-$, $-SO_2NR^{15}-$, $-NR^{15}SO_2-$ and $-P(O)OH-$, wherein q is an integer from 1 to 6;

wherein:

$(PEG)_n$ is

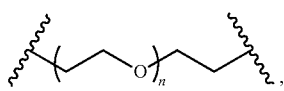

where n is an integer from 1 to 30;
EDA is an ethylene diamine moiety having the following structure:

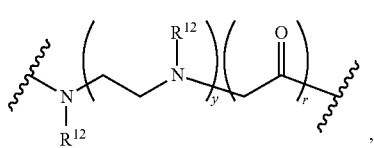

where y is an integer from 1 to 6 and r is 0 or 1;
4-amino-piperidine (4AP) is

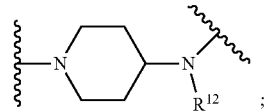

AA is an amino acid residue, where p is an integer from 1 to 20;

each $R^{13}$ is independently selected from hydrogen, an alkyl, a substituted alkyl, an aryl, and a substituted aryl; and each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In certain embodiments, $T^5$, $T^6$, $T^7$ and $T^8$ and $V^5$, $V^6$, $V^7$ and $V^8$ are not present (i.e., the sum of e, f, g, and h is 0).

In certain embodiments, $T^5$, $T^6$, $T^7$ and $T^8$ and $V^5$, $V^6$, $V^7$ and $V^8$ are selected from the following:

$T^5$ is a covalent bond and $V^5$ is $-C(O)-$;
f is 0 (i.e., $T^6$ and $V^6$ are not present);
g is 0 (i.e., $T^7$ and $V^7$ are not present); and
h is 0 (i.e., $T^8$ and $V^8$ are not present).

In certain embodiments, $T^5$, $T^6$, $T^7$ and $T^8$ and $V^5$, $V^6$, $V^7$ and $V^8$ are selected from the following:

$T^5$ is a covalent bond and $V^5$ is $-CONR^{15}-$;
$T^6$ is alkyl and $V^6$ is $-CO-$;
g is 0 (i.e., $T^7$ and $V^7$ are not present); and
h is 0 (i.e., $T^8$ and $V^8$ are not present).

In certain embodiments, the left-hand side of the above linker structure is attached to the first cleavable moiety, and the right-hand side of the above linker structures is attached to the drug.

Any of the chemical entities, linkers and coupling moieties set forth in the structures above may be adapted for use in the subject compounds and conjugates.

Additional disclosure related to hydrazinyl-indolyl and hydrazinyl-pyrrolo-pyridinyl compounds and methods for producing a conjugate is found in U.S. Pat. Nos. 9,310,374 and 9,493,413, the disclosures of each of which are incorporated herein by reference.

Compounds Useful for Producing Conjugates

The present disclosure provides hydrazinyl-indolyl and hydrazinyl-pyrrolo-pyridinyl compounds useful for producing the conjugates described herein. In certain embodiments, the hydrazinyl-indolyl or hydrazinyl-pyrrolo-pyridinyl compound may be a coupling moiety useful for conjugation of an antibody and a drug or active agent. For example, the hydrazinyl-indolyl or hydrazinyl-pyrrolo-pyridinyl compound may be bound to the antibody and also bound to the drug, thus indirectly binding the antibody and the drug together.

In certain embodiments, the compound includes a cleavable linker for linking an antibody to a drug, where the cleavable linker comprises a first enzymatically cleavable moiety and a second enzymatically cleavable moiety comprising a glycoside selected from the group consisting of a galactoside, a glucoside, a mannoside, a fucoside, O-GlcNAc, and O-GalNAc.

In certain embodiments, the compound is a compound of formula (II):

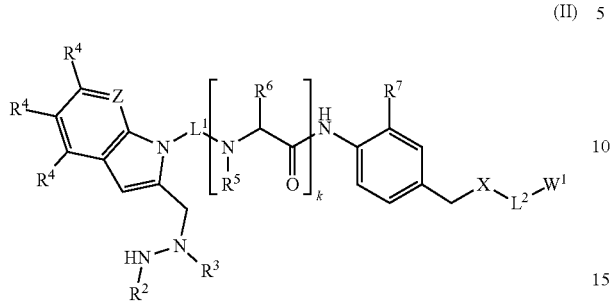

wherein
Z is CR$^4$ or N;
X is O or NR$^4$;
R$^2$ and R$^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or R$^2$ and R$^3$ are optionally cyclically linked to form a 5 or 6-membered heterocyclyl;

each R$^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

each R$^5$ is independently selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

each R$^6$ is independently selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

k is an integer from 1 to 10;
R$^7$ is the second enzymatically cleavable moiety;
L$^1$ is a first linker;
L$^2$ is a second linker; and
W$^1$ is a drug.

In some instances, k is 2, and the compound is a compound of formula (IIa):

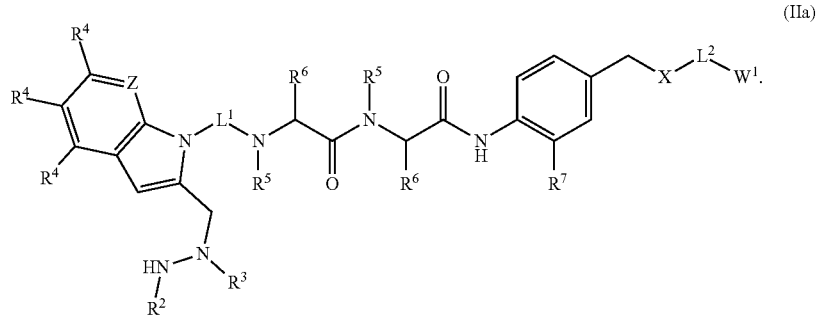

For example, the compound may be a compound of formula (IIb):

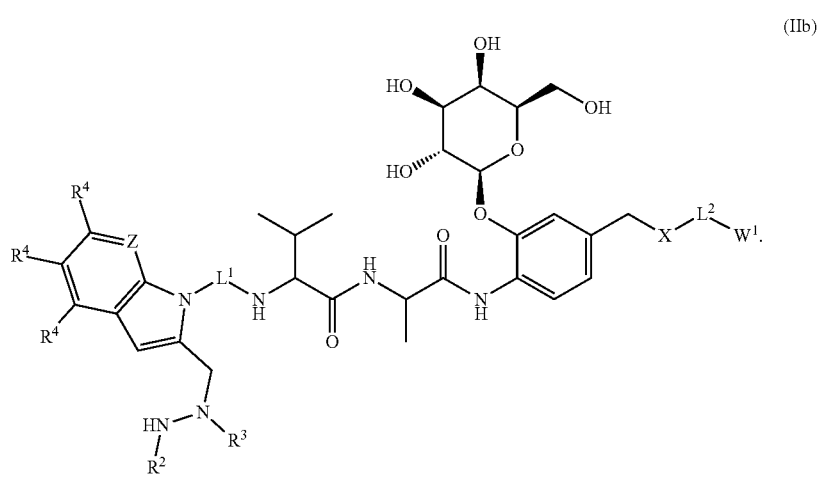

In some instances, the compound may be a compound of formula (IIc):
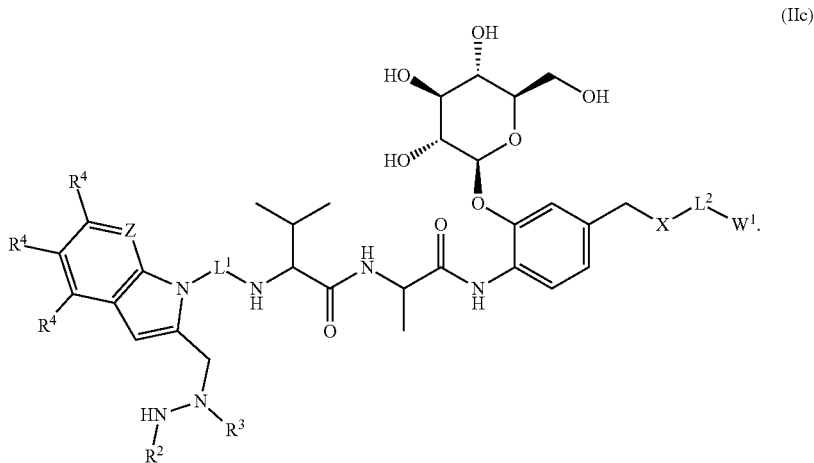
(IIc)
In some instances, the compound may be a compound of formula (IId):
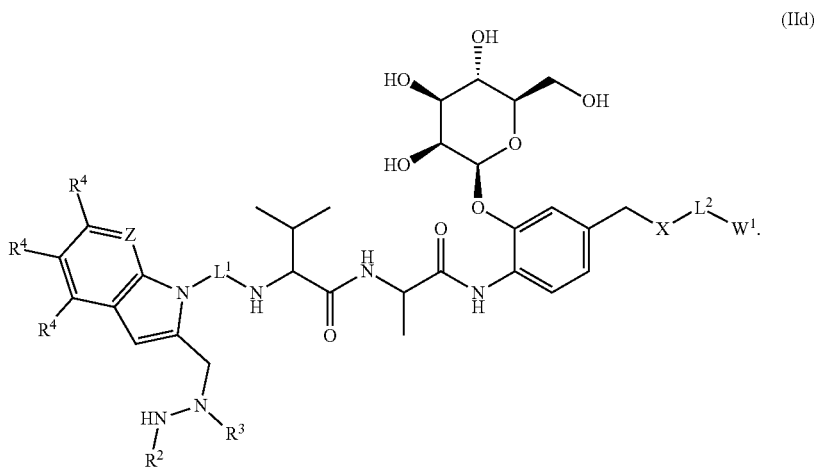
(IId)
In some instances, the compound may be a compound of formula (IIe):
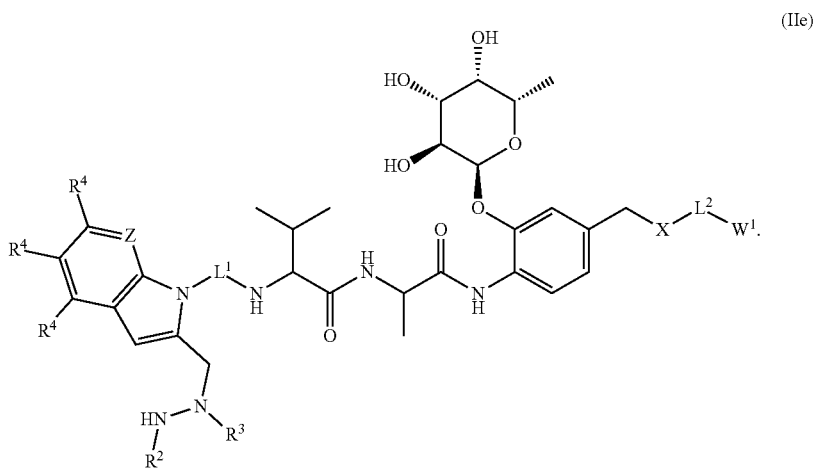
(IIe)

In some instances, the compound may be a compound of formula (IIf):

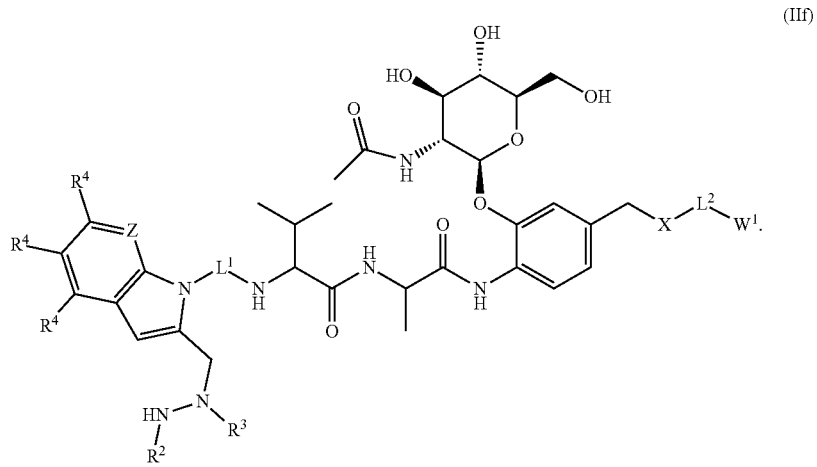

(IIf)

In some instances, the compound may be a compound of formula (IIg):

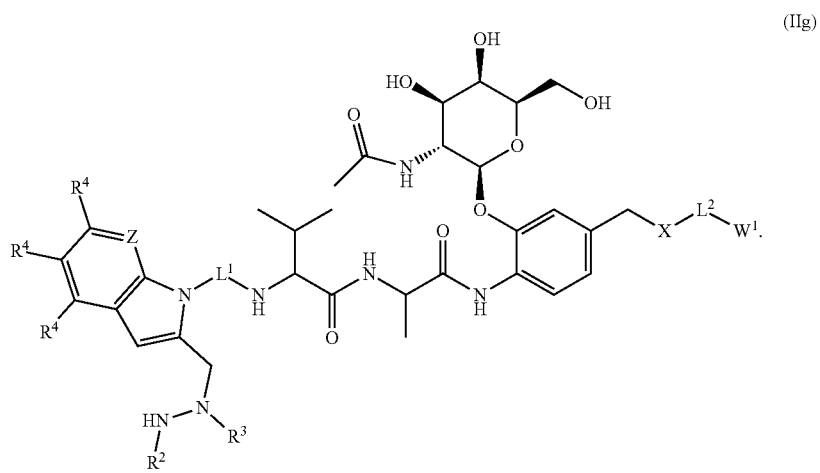

(IIg)

The substituents related to conjugates of formula (II) are described herein. References to formula (II) are intended to also encompass formulae (IIa), (IIb), (IIc), (IId), (IIe), (IIf), and (IIg).

Regarding compound of formula (II), the substituents Z, $R^2$, $R^3$, $R^4$, $R^5$, $R^6$, $R^7$, $L^1$, $L^2$, and $W^1$ are as described above in relation to the conjugates of formula (I). Similarly, regarding the first linker $L^1$ and the second linker $L^2$ of formula (II), the $T^1$, $T^2$, $T^3$, $T^4$, $V^1$, $V^2$, $V^3$, and $V^4$, and $T^5$, $T^6$, $T^7$, $T^8$, $V^5$, $V^6$, $V^7$ and $V^8$ substituents are as described above in relation to the conjugates of formula (I).

In certain embodiments, the compound is of the following structure:

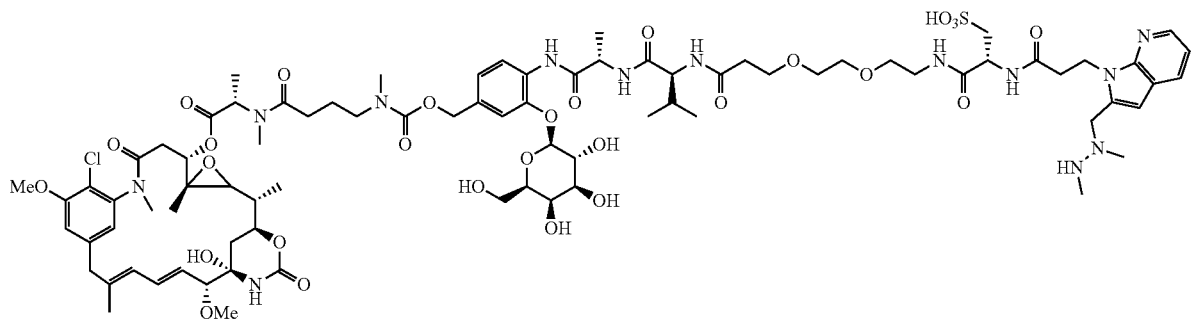

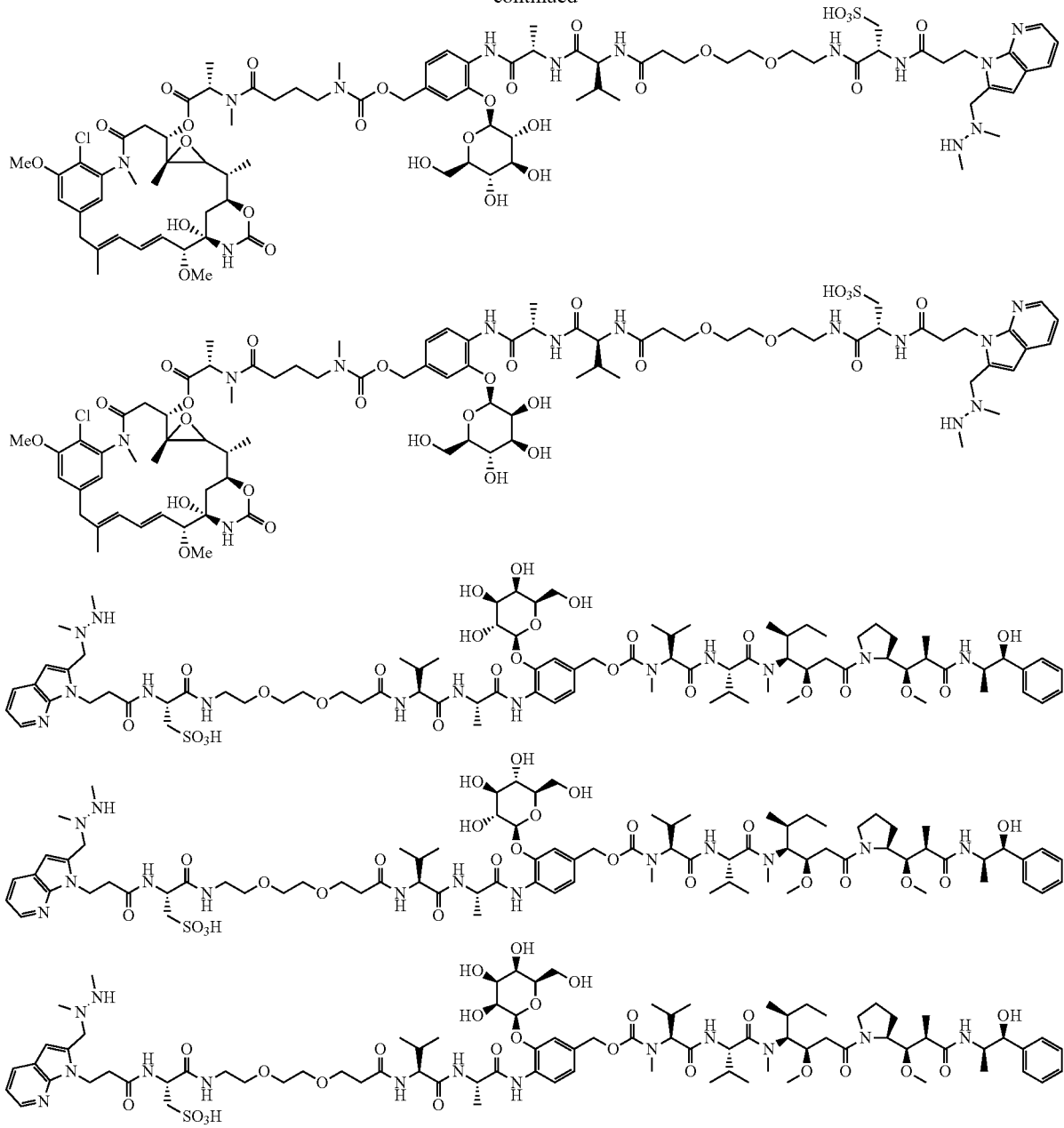

Antibodies

As noted above, a subject conjugate can comprise as substituent $W^2$ an antibody, where the antibody has been modified to include a 2-formylglycine (FGly) residue. As used herein, amino acids may be referred to by their standard name, their standard three letter abbreviation and/or their standard one letter abbreviation, such as: Alanine or Ala or A; Cysteine or Cys or C; Aspartic acid or Asp or D; Glutamic acid or Glu or E; Phenylalanine or Phe or F; Glycine or Gly or G; Histidine or His or H; Isoleucine or Ile or I; Lysine or Lys or K; Leucine or Leu or L; Methionine or Met or M; Asparagine or Asn or N; Proline or Pro or P; Glutamine or Gln or Q; Arginine or Arg or R; Serine or Ser or S; Threonine or Thr or T; Valine or Val or V; Tryptophan or Trp or W; and Tyrosine or Tyr or Y.

In certain embodiments, the amino acid sequence of an antibody is modified to include a sulfatase motif that contains a serine or cysteine residue that is capable of being converted (oxidized) to a 2-formylglycine (FGly) residue by action of a formylglycine generating enzyme (FGE) either in vivo (e.g., at the time of translation of an aldehyde tag-containing protein in a cell) or in vitro (e.g., by contacting an aldehyde tag-containing protein with an FGE in a cell-free system). Such sulfatase motifs may also be referred to herein as an FGE-modification site.

Sulfatase Motifs

A minimal sulfatase motif of an aldehyde tag is usually 5 or 6 amino acid residues in length, usually no more than 6 amino acid residues in length. Sulfatase motifs provided in an Ig polypeptide are at least 5 or 6 amino acid residues, and can be, for example, from 5 to 16, 6-16, 5-15, 6-15, 5-14, 6-14, 5-13, 6-13, 5-12, 6-12, 5-11, 6-11, 5-10, 6-10, 5-9, 6-9, 5-8, or 6-8 amino acid residues in length, so as to define a sulfatase motif of less than 16, 15, 14, 13, 12, 11, 10, 9, 8, 7 or 6 amino acid residues in length.

In certain embodiments, polypeptides of interest include those where one or more amino acid residues, such as 2 or more, or 3 or more, or 4 or more, or 5 or more, or 6 or more, or 7 or more, or 8 or more, or 9 or more, or 10 or more, or 11 or more, or 12 or more, or 13 or more, or 14 or more, or 15 or more, or 16 or more, or 17 or more, or 18 or more, or 19 or more, or 20 or more amino acid residues have been inserted, deleted, substituted (replaced) relative to the native amino acid sequence to provide for a sequence of a sulfatase motif in the polypeptide. In certain embodiments, the polypeptide includes a modification (insertion, addition, deletion, and/or substitution/replacement) of less than 20, 19, 18, 17, 16, 15, 14, 13, 12, 11, 10, 9, 8, 7, 6, 5, 4, 3 or 2 amino acid residues of the amino acid sequence relative to the native amino acid sequence of the polypeptide. Where an amino acid sequence native to the polypeptide (e.g., antibody) contains one or more residues of the desired sulfatase motif, the total number of modifications of residues can be reduced, e.g., by site-specification modification (insertion, addition, deletion, substitution/replacement) of amino acid residues flanking the native amino acid residues to provide a sequence of the desired sulfatase motif. In certain embodiments, the extent of modification of the native amino acid sequence of the target antibody is minimized, so as to minimize the number of amino acid residues that are inserted, deleted, substituted (replaced), or added (e.g., to the N- or C-terminus). Minimizing the extent of amino acid sequence modification of the target antibody may minimize the impact such modifications may have upon antibody function and/or structure.

It should be noted that while aldehyde tags of particular interest are those comprising at least a minimal sulfatase motif (also referred to a "consensus sulfatase motif"), it will be readily appreciated that longer aldehyde tags are both contemplated and encompassed by the present disclosure and can find use in the compositions and methods of the present disclosure. Aldehyde tags can thus comprise a minimal sulfatase motif of 5 or 6 residues, or can be longer and comprise a minimal sulfatase motif which can be flanked at the N- and/or C-terminal sides of the motif by additional amino acid residues. Aldehyde tags of, for example, 5 or 6 amino acid residues are contemplated, as well as longer amino acid sequences of more than 5, 6, 7, 8, 9, 10, 11, 12, 13, 14, 15, 16, 17, 18, 19, 20 or more amino acid residues.

An aldehyde tag can be present at or near the C-terminus of an Ig heavy chain; e.g., an aldehyde tag can be present within 1, 2, 3, 4, 5, 6, 7, 8, 9, or 10 amino acids of the C-terminus of a native, wild-type Ig heavy chain. An aldehyde tag can be present within a CH1 domain of an Ig heavy chain. An aldehyde tag can be present within a CH2 domain of an Ig heavy chain. An aldehyde tag can be present within a CH3 domain of an Ig heavy chain. An aldehyde tag can be present in an Ig light chain constant region, e.g., in a kappa light chain constant region or a lambda light chain constant region.

In certain embodiments, the sulfatase motif used may be described by the formula:

$$X^1Z^{10}X^2Z^{20}X^3Z^{30} \quad (I')$$

where $Z^{10}$ is cysteine or serine (which can also be represented by (C/S));

$Z^{20}$ is either a proline or alanine residue (which can also be represented by (P/A));

$Z^{30}$ is a basic amino acid (e.g., arginine (R), and may be lysine (K) or histidine (H), e.g., lysine), or an aliphatic amino acid (alanine (A), glycine (G), leucine (L), valine (V), isoleucine (I), or proline (P), e.g., A, G, L, V, or I;

$X^1$ is present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M, S or V, with the proviso that when the sulfatase motif is at the N-terminus of the target polypeptide, $X^1$ is present; and $X^2$ and $X^3$ independently can be any amino acid, though usually an aliphatic amino acid, a polar, uncharged amino acid, or a sulfur containing amino acid (i.e., other than an aromatic amino acid or a charged amino acid), e.g., S, T, A, V, G or C, e.g., S, T, A, V or G.

The amino acid sequence of an antibody heavy and/or light chain can be modified to provide a sequence of at least 5 amino acids of the formula $X^1Z^{10}X^2Z^{20}X^3Z^{30}$, where $Z^{10}$ is cysteine or serine;

$Z^{20}$ is a proline or alanine residue;

$Z^{30}$ is an aliphatic amino acid or a basic amino acid;

$X^1$ is present or absent and, when present, is any amino acid, with the proviso that when the heterologous sulfatase motif is at an N-terminus of the polypeptide, $X^1$ is present;

$X^2$ and $X^3$ are each independently any amino acid.

The sulfatase motif is generally selected so as to be capable of conversion by a selected FGE, e.g., an FGE present in a host cell in which the aldehyde tagged polypeptide is expressed or an FGE which is to be contacted with the aldehyde tagged polypeptide in a cell-free in vitro method.

For example, where the FGE is a eukaryotic FGE (e.g., a mammalian FGE, including a human FGE), the sulfatase motif can be of the formula:

$$X^1CX^2PX^3Z^{30} \quad (I'')$$

where $X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, S or V, with the proviso that when the sulfatase motif is at the N-terminus of the target polypeptide, $X^1$ is present;

$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G, or C, e.g., S, T, A, V or G; and $Z^{30}$ is a basic amino acid (e.g., arginine (R), and may be lysine (K) or histidine (H), e.g., lysine), or an aliphatic amino acid (alanine (A), glycine (G), leucine (L), valine (V), isoleucine (I), or proline (P), e.g., A, G, L, V, or I.

Specific examples of sulfatase motifs include LCTPSR (SEQ ID NO: 1), MCTPSR (SEQ ID NO: 2), VCTPSR (SEQ ID NO: 3, LCSPSR (SEQ ID NO: 4), LCAPSR (SEQ ID NO: 5), LCVPSR (SEQ ID NO: 6), LCGPSR (SEQ ID NO: 7), ICTPAR (SEQ ID NO: 8), LCTPSK (SEQ ID NO: 9), MCTPSK (SEQ ID NO: 10), VCTPSK (SEQ ID NO: 11), LCSPSK (SEQ ID NO: 12), LCAPSK (SEQ ID NO:

13), LCVPSK (SEQ ID NO: 14), LCGPSK (SEQ ID NO: 15), LCTPSA (SEQ ID NO: 16), ICTPAA (SEQ ID NO: 17), MCTPSA (SEQ ID NO: 18), VCTPSA (SEQ ID NO: 19), LCSPSA (SEQ ID NO: 20), LCAPSA (SEQ ID NO: 21), LCVPSA (SEQ ID NO: 22), and LCGPSA (SEQ ID NO: 23).

FGly-Containing Sequences

Upon action of FGE on the modified antibody heavy and/or light chain, the serine or the cysteine in the sulfatase motif is modified to FGly. Thus, the FGly-containing sulfatase motif can be of the formula:

$$X^1(FGly)X^2Z^{20}X^3Z^{30} \qquad (I''')$$

where

FGly is the formylglycine residue;

$Z^{20}$ is either a proline or alanine residue (which can also be represented by (P/A));

$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;

$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present; and $X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G.

As described above, the modified polypeptide containing the FGly residue may be conjugated to a drug (e.g., a maytansinoid) by reaction of the FGly with the drug (e.g., a drug containing a hydrazinyl-indolyl or a hydrazinyl-pyrrolo-pyridinyl coupling moiety, as described above) to produce an FGly'-containing sulfatase motif. As used herein, the term FGly' refers to the modified amino acid residue of the sulfatase motif that is coupled to the drug, such as a maytansine or an auristatin. Thus, the FGly'-containing sulfatase motif can be of the formula:

$$X^1(FGly')X^2Z^{20}X^3Z^{30} \qquad (II)$$

where

FGly' is the modified amino acid residue of formula (I);

$Z^{20}$ is either a proline or alanine residue (which can also be represented by (P/A));

$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;

$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present; and $X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G.

Site of Modification

As noted above, the amino acid sequence of an antibody is modified to include a sulfatase motif that contains a serine or cysteine residue that is capable of being converted (oxidized) to an FGly residue by action of an FGE either in vivo (e.g., at the time of translation of an aldehyde tag-containing protein in a cell) or in vitro (e.g., by contacting an aldehyde tag-containing protein with an FGE in a cell-free system). The antibody used to generate a conjugate of the present disclosure include at least an Ig constant region, e.g., an Ig heavy chain constant region (e.g., at least a CH1 domain; at least a CH1 and a CH2 domain; a CH1, a CH2, and a CH3 domain; or a CH1, a CH2, a CH3, and a CH4 domain), or an Ig light chain constant region. Such Ig polypeptides are referred to herein as "target Ig polypeptides" or "target antibodies".

The site in an antibody into which a sulfatase motif is introduced can be any convenient site. As noted above, in some instances, the extent of modification of the native amino acid sequence of the target polypeptide is minimized, so as to minimize the number of amino acid residues that are inserted, deleted, substituted (replaced), and/or added (e.g., to the N- or C-terminus). Minimizing the extent of amino acid sequence modification of the target antibody may minimize the impact such modifications may have upon antibody function and/or structure.

An antibody heavy chain constant region can include Ig constant regions of any heavy chain isotype, non-naturally occurring Ig heavy chain constant regions (including consensus Ig heavy chain constant regions). An Ig constant region can be modified to include an aldehyde tag, where the aldehyde tag is present in or adjacent a solvent-accessible loop region of the Ig constant region. An Ig constant region can be modified by insertion and/or substitution of 1, 2, 3, 4, 5, 6, 7, 8, 9, 10, 11, 12, 13, 14, 15, or 16 amino acids, or more than 16 amino acids, to provide an amino acid sequence of a sulfatase motif as described above.

In some cases, an aldehyde-tagged antibody comprises an aldehyde-tagged Ig heavy chain constant region (e.g., at least a CH1 domain; at least a CH1 and a CH2 domain; a CH1, a CH2, and a CH3 domain; or a CH1, a CH2, a CH3, and a CH4 domain). The aldehyde-tagged Ig heavy chain constant region can include heavy chain constant region sequences of an IgA, IgM, IgD, IgE, IgG1, IgG2, IgG3, or IgG4 isotype heavy chain or any allotypic variant of same, e.g., human heavy chain constant region sequences or mouse heavy chain constant region sequences, a hybrid heavy chain constant region, a synthetic heavy chain constant region, or a consensus heavy chain constant region sequence, etc., modified to include at least one sulfatase motif that can be modified by an FGE to generate an FGly-modified Ig polypeptide. Allotypic variants of Ig heavy chains are known in the art. See, e.g., Jefferis and Lefranc (2009) MAbs 1:4.

In some cases, an aldehyde-tagged antibody comprises an aldehyde-tagged Ig light chain constant region. The aldehyde-tagged Ig light chain constant region can include constant region sequences of a kappa light chain, a lambda light chain, e.g., human kappa or lambda light chain constant regions, a hybrid light chain constant region, a synthetic light chain constant region, or a consensus light chain constant region sequence, etc., modified to include at least one sulfatase motif that can be modified by an FGE to generate an FGly-modified antibody. Exemplary constant regions include human gamma 1 and gamma 3 regions. With the exception of the sulfatase motif, a modified constant region may have a wild-type amino acid sequence, or it may have an amino acid sequence that is at least 70% identical (e.g., at least 80%, at least 90% or at least 95% identical) to a wild type amino acid sequence.

In some embodiments the sulfatase motif is at a position other than, or in addition to, the C-terminus of the Ig polypeptide heavy chain. As noted above, an isolated aldehyde-tagged antibody can comprise a heavy chain constant region modified to include a sulfatase motif as described above, where the sulfatase motif is in or adjacent a surface-accessible loop region of the antibody heavy chain constant region.

A sulfatase motif can be provided within or adjacent one or more of these amino acid sequences of such modification sites of an Ig heavy chain. For example, an Ig heavy chain polypeptide can be modified (e.g., where the modification includes one or more amino acid residue insertions, deletions, and/or substitutions) at one or more of these amino acid sequences to provide a sulfatase motif adjacent and N-terminal and/or adjacent and C-terminal to these modification sites. Alternatively or in addition, an Ig heavy chain polypeptide can be modified (e.g., where the modification includes one or more amino acid residue insertions, deletions, and/or substitutions) at one or more of these amino acid sequences to provide a sulfatase motif between any two residues of the Ig heavy chain modifications sites. In some embodiments, an Ig heavy chain polypeptide may be modified to include two motifs, which may be adjacent to one another, or which may be separated by one, two, three, four or more (e.g., from about 1 to about 25, from about 25 to about 50, or from about 50 to about 100, or more, amino acids. Alternatively or in addition, where a native amino acid sequence provides for one or more amino acid residues of a sulfatase motif sequence, selected amino acid residues of the modification sites of an Ig heavy chain polypeptide amino acid sequence can be modified (e.g., where the modification includes one or more amino acid residue insertions, deletions, and/or substitutions) so as to provide a sulfatase motif at the modification site.

An antibody used in an antibody-drug conjugate of the present disclosure can have any of a variety of antigen-binding specificities, including but not limited to, e.g., an antigen present on a cancer cell; an antigen present on an autoimmune cell; an antigen present on a pathogenic microorganism; an antigen present on a virus-infected cell (e.g., a human immunodeficiency virus-infected cell); an antigen present on a diseased cell; and the like. For example, an antibody conjugate can bind an antigen, where the antigen is present on the surface of the cell. An antibody conjugate of the present disclosure can bind antigen with a suitable binding affinity, e.g., from $5\times10^{-6}$ M to $10^{-7}$ M, from $10^{-7}$ M to $5\times10^{-7}$ M, from $5\times10^{-7}$ M to $10^{-8}$ M, from $10^{-8}$ M to $5\times10^{-8}$ M, from $5\times10^{-8}$ M to $10^{-9}$ M, or a binding affinity greater than $10^{-9}$ M.

As non-limiting examples, a subject antibody conjugate can bind an antigen present on a cancer cell (e.g., a tumor-specific antigen; an antigen that is over-expressed on a cancer cell; etc.), and the conjugated moiety can be a drug, such as a cytotoxic compound (e.g., a cytotoxic small molecule, a cytotoxic synthetic peptide, etc.). For example, a subject antibody conjugate can be specific for an antigen on a cancer cell, where the conjugated moiety is a drug, such as a cytotoxic compound (e.g., a cytotoxic small molecule, a cytotoxic synthetic peptide, etc.).

As further non-limiting examples, a subject antibody conjugate can bind an antigen present on a cell infected with a virus (e.g., where the antigen is encoded by the virus; where the antigen is expressed on a cell type that is infected by a virus; etc.), and the conjugated moiety can be a drug, such as a viral fusion inhibitor. For example, a subject antibody conjugate can bind an antigen present on a cell infected with a virus, and the conjugated moiety can be a drug, such as a viral fusion inhibitor.

Drugs for Conjugation to a Polypeptide

The present disclosure provides drug-polypeptide conjugates (e.g., antibody-drug conjugates). Any of a number of drugs are suitable for use, or can be modified to be rendered suitable for use, as a reactive partner to conjugate to an antibody. Examples of drugs include small molecule drugs and peptide drugs.

"Small molecule drug" as used herein refers to a compound, e.g., an organic compound, which exhibits a pharmaceutical activity of interest and which is generally of a molecular weight of 800 Da or less, or 2000 Da or less, but can encompass molecules of up to 5 kDa and can be as large as 10 kDa. A small inorganic molecule refers to a molecule containing no carbon atoms, while a small organic molecule refers to a compound containing at least one carbon atom.

For example, the drug or active agent can be a maytansine. "Maytansine", "maytansine moiety", "maytansine active agent moiety" and "maytansinoid" refer to a maytansine and analogs and derivatives thereof, and pharmaceutically active maytansine moieties and/or portions thereof. A maytansine conjugated to the polypeptide can be any of a variety of maytansinoid moieties such as, but not limited to, maytansine and analogs and derivatives thereof as described herein (e.g., deacylmaytansine). In other instances, the drug or active agent can be an auristatin, or an analog or derivative thereof, or a pharmaceutically active auristatin moiety and/or a portion thereof. An auristatin conjugated to the polypeptide can be any of a variety of auristatin moieties such as, but not limited to, an auristatin and analogs and derivatives thereof as described herein. In other cases, the drug or active agent can be a duocarmycin, or an analog or derivative thereof, or a pharmaceutically active duocarmycin moiety and/or a portion thereof. A duocarmycin conjugated to the polypeptide can be any of a variety of duocarmycin moieties such as, but not limited to, a duocarmycin and analogs and derivatives thereof as described herein.

In certain embodiments, the drug is selected from a cytotoxin, a kinase inhibitor, an immunostimulatory agent, a toll-like receptor (TLR) agonist, an oligonucleotide, an aptamer, a cytokine, a steroid, and a peptide.

For example, a cytotoxin can include any compound that leads to cell death (e.g., necrosis or apoptosis) or a decrease in cell viability.

Kinase inhibitors can include, but are not limited to, Adavosertib, Afatinib, Axitinib, Bosutinib, Cetuximab, Cobimetinib, Crizotinib, Cabozantinib, Dacomitinib, Dasatinib, Entrectinib, Erdafitinib, Erlotinib, Fostamatinib, Gefitinib, Ibrutinib, Imatinib, Lapatinib, Lenvatinib, Mubritinib, Nilotinib, Pazopanib, Pegaptanib, Ruxolitinib, Sorafenib, Sunitinib, Tucatinib, Vandetanib, Vemurafenib, and the like.

Immunostimulatory agents can include, but are not limited to, vaccines (e.g., bacterial or viral vaccines), colony stimulating factors, interferons, interleukins, and the like. TLR agonists include, but are not limited to, imiquimod, resiquimod, and the like.

Oligonucleotide dugs include, but are not limited to, fomivirsen, pegaptanib, mipomersen, eteplirsen, defibrotide, nusinersen, golodirsen, viltolarsen, volanesorsen, inotersen, tofersen, tominersen, and the like.

Aptamer drugs include, but are not limited to, pegaptanib, AS1411, REG1, ARC1779, NU172, ARC1905, E10030, NOX-A12, NOX-E36, and the like.

Cytokines include, but are not limited to, Albinterferon Alfa-2B, Aldesleukin, ALT-801, Anakinra, Ancestim, Avotermin, Balugrastim, Bempegaldesleukin, Binetrakin, Cintredekin Besudotox, CTCE-0214, Darbepoetin alfa, Denileukin diftitox, Dulanermin, Edodekin alfa, Emfilermin, Epoetin delta, Erythropoietin, Human interleukin-2, Interferon alfa, Interferon alfa-2c, Interferon alfa-n1, Interferon alfa-n3, Interferon alfacon-1, Interferon beta-1a, Interferon beta-1b, Interferon gamma-1b, Interferon Kappa, Interleukin-1 alpha, Interleukin-10, Interleukin-7, Lenograstim, Leridistim, Lipegfilgrastim, Lorukafusp alfa, Maxy-G34, Methoxy polyethylene glycol-epoetin beta, Molgramostim, Muplestim, Nagrestipen, Oprelvekin, Pegfilgrastim, Pegilodecakin, Peginterferon alfa-2a, Peginterferon alfa-2b, Peginterferon beta-1a, Peginterferon lambda-1a, Recombinant CD40-ligand, Regramostim, Romiplostim, Sargramostim, Thrombopoietin, Tucotuzumab celmoleukin, Viral Macrophage-Inflammatory Protein, and the like.

Steroid drugs include, but are not limited to, prednisolone, betamethasone, dexamethasone, hydrocortisone, methylprednisolone, deflazacort, and the like.

"Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight. Suitable peptides include, but are not limited to, cytotoxic peptides; angiogenic peptides; anti-angiogenic peptides; peptides that activate B cells; peptides that activate T cells; anti-viral peptides; peptides that inhibit viral fusion; peptides that increase production of one or more lymphocyte populations; anti-microbial peptides; growth factors; growth hormone-releasing factors; vasoactive peptides; anti-inflammatory peptides; peptides that regulate glucose metabolism; an anti-thrombotic peptide; an anti-nociceptive peptide; a vasodilator peptide; a platelet aggregation inhibitor; an analgesic; and the like.

Examples of drugs that find use in the conjugates and compounds described herein include, but are not limited to Tubulysin M, Calicheamicin, SN-38, Exatecan, a STAT3 inhibitor, alpha-Amanitin, an aurora kinase inhibitor, belotecan, 9-aminocamptothecin (9-AC), and an anthracycline.

Other examples of drugs include small molecule drugs, such as a cancer chemotherapeutic agent. For example, where the polypeptide is an antibody (or fragment thereof) that has specificity for a tumor cell, the antibody can be modified as described herein to include a modified amino acid, which can be subsequently conjugated to a cancer chemotherapeutic agent. Cancer chemotherapeutic agents include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used.

Suitable cancer chemotherapeutic agents include dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD)).

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-7; (8) colony-stimulating factors; and (9) inhibitors of angiogenesis.

Examples of drugs include small molecule drugs, such as a cancer chemotherapeutic agent. For example, where the polypeptide is an antibody (or fragment thereof) that has specificity for a tumor cell, the antibody can be modified as described herein to include a modified amino acid, which can be subsequently conjugated to a cancer chemotherapeutic agent, such as a microtubule affecting agent. In certain embodiments, the drug is a microtubule affecting agent that has antiproliferative activity, such as a maytansinoid.

In certain embodiments, the drug is a maytansinoid, which as the following structure:

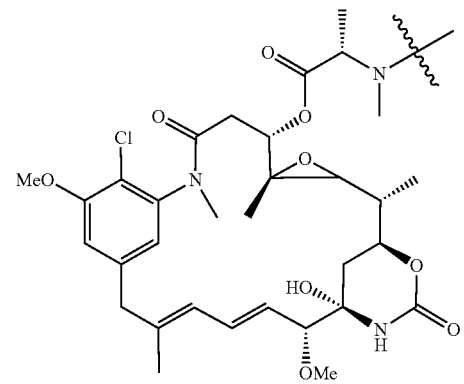

where $\sim$ indicates the point of attachment between the maytansinoid and the second linker, $L^2$, in conjugates and compounds described herein. By "point of attachment" is meant that the $\sim$ symbol indicates the bond between the N of the maytansinoid and the second linker, $L^2$, in conjugates and compounds described herein. For example, in formula (I), $W^1$ may be a maytansinoid, such as a maytansinoid of the structure above, where $\sim$ indicates the point of attachment between the maytansinoid and the second linker, $L^2$. In some cases, the maytansinoid of the structure above may be referred to as a deacyl maytansine.

In certain embodiments, the drug is an antimitotic agent, such as an auristatin or an active auristatin analog or derivative thereof (e.g., Monomethyl auristatin D (MMAD), monomethyl auristatin E (MMAE), monomethyl auristatin F (MMAF), and the like). In certain embodiments, the drug is MMAE, which has the following structure:

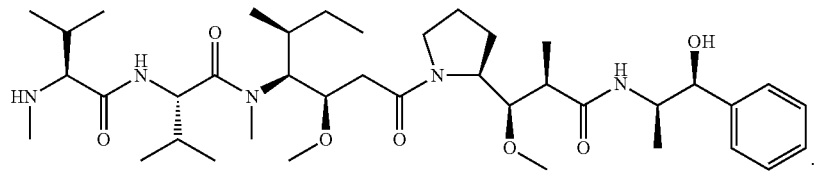

For example, the MMAE active agent can be included in an antibody-drug conjugate as follows:

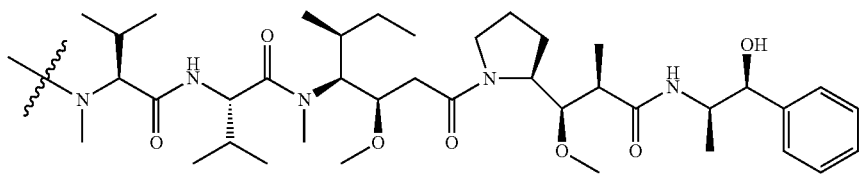 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

where ⌇ indicates the point of attachment between the auristatin and the second linker, $L^2$, in conjugates and compounds described herein. For example, the ⌇ symbol indicates the bond between the N of the auristatin and the second linker, $L^2$, e.g., as shown in formula (I). For instance, in formula (I), $W^1$ can be an auristatin, such as MMAE, where ⌇ in the structure above indicates the point of attachment between MMAE and the second linker, $L^2$.

In certain embodiments, the drug is a DNA alkylating agent, such as a duocarmycin. Examples of duocarmycin include, but are not limited to, duocarmycin A, duocarmycin B1, duocarmycin B2, duocarmycin C1, duocarmycin C2, duocarmycin D, duocarmycin SA, and CC-1065. In some embodiments, the duocarmycin is a duocarmycin analog, such as, but not limited to, adozelesin, bizelesin, or carzelesin.

In some instances, the duocarmycin is a compound having the following structure:

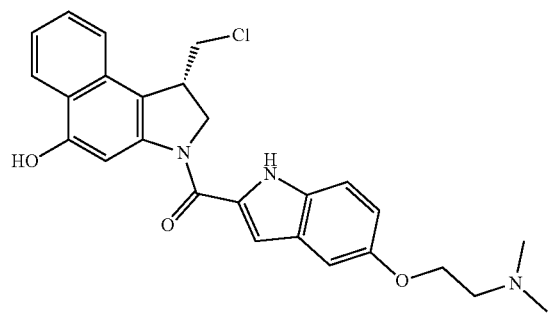

For example, the duocarmycin active agent can be included in an antibody-drug conjugate as follows:

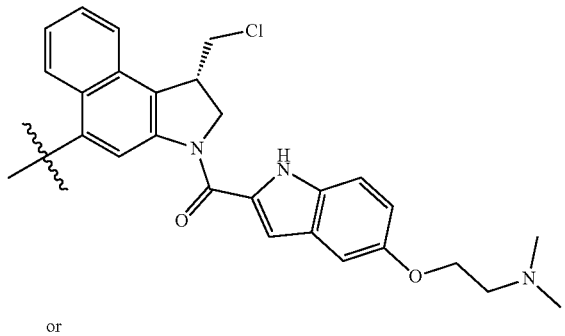

or

-continued

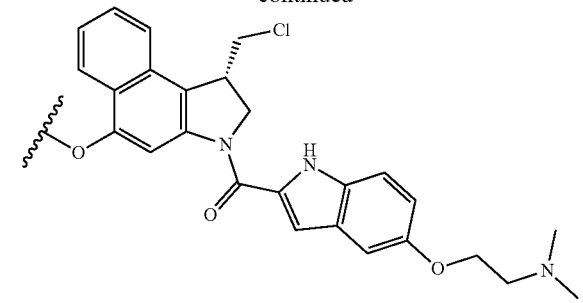

where ⌇ indicates the point of attachment between the duocarmycin and the second linker, $L^2$, in conjugates and compounds described herein. For example, the ⌇ symbol indicates the bond between the duocarmycin and the second linker, $L^2$, e.g., as shown in formula (I). For instance, in formula (I), $W^1$ can be a duocarmycin, such as a duocarmycin shown above, where ⌇ indicates the point of attachment between the duocarmycin and the second linker, $L^2$.

As described above, in certain embodiments, $L^2$ is a second linker described by the formula -$(L^{21})_e$-$(L^{22})_f$-$(L^{23})_g$-$(L^{24})_h$-, wherein $L^{21}$, $L^{22}$, $L^{23}$ and $L^{24}$ are each independently a second linker subunit. In certain embodiments, $L^{21}$ is attached to the first cleavable moiety. In certain embodiments, $L^{21}$, if present, is also attached to $W^1$ (the drug). In certain embodiments, $L^{22}$, if present, is attached to $W^1$ (the drug). In certain embodiments, $L^{23}$, if present, is attached to $W^1$ (the drug). In certain embodiments, $L^{24}$, if present, is attached to $W^1$ (the drug).

As described above, in certain embodiments, the second linker -$(L^{21})_e$-$(L^{22})_f$-$(L^{23})_g$-$(L^{24})_h$- is described by the formula -$(T^5$-$V^5)_e$-$(T^6$-$V^6)_f$-$(T^7$-$V^7)_g$-$(T^8$-$V^8)_h$—, where e, f, g and h are each independently 0 or 1, where the sum of e, f, g and h is 0 to 4. In certain embodiments, as described above, $L^{21}$ is attached to the first cleavable moiety. As such, in certain embodiments, $T^5$ is attached to the first cleavable moiety. In certain embodiments, $V^5$ is attached to $W^1$ (the drug). In certain embodiments, as described above, $L^{22}$, if present, is attached to $W^1$ (the drug). As such, in certain embodiments, $T^6$, if present, is attached to $W^1$ (the drug), or $V^6$, if present, is attached to $W^1$ (the drug). In certain embodiments, as described above, $L^{23}$, if present, is attached to $W^1$ (the drug). As such, in certain embodiments, $T^7$, if present, is attached to $W^1$ (the drug), or $V^7$, if present, is attached to $W^1$ (the drug). In certain embodiments, as described above, $L^{24}$, if present, is attached to $W^1$ (the drug). As such, in certain embodiments, $T^8$, if present, is attached to $W^1$ (the drug), or $V^8$, if present, is attached to $W^1$ (the drug).

Embodiments of the present disclosure include conjugates where an antibody is conjugated to one or more drug moieties, such as 2 drug moieties, 3 drug moieties, 4 drug moieties, 5 drug moieties, 6 drug moieties, 7 drug moieties, 8 drug moieties, 9 drug moieties, or 10 or more drug moieties. The drug moieties may be conjugated to the antibody at one or more sites in the antibody, as described herein. In certain embodiments, the conjugates have an average drug-to-antibody ratio (DAR) (molar ratio) in the range of from 0.1 to 10, or from 0.5 to 10, or from 1 to 10, such as from 1 to 9, or from 1 to 8, or from 1 to 7, or from 1 to 6, or from 1 to 5, or from 1 to 4, or from 1 to 3, or from 1 to 2. In certain embodiments, the conjugates have an average DAR from 1 to 2, such as 1, 1.1, 1.2, 1.3, 1.4, 1.5, 1.6, 1.7, 1.8, 1.9 or 2. In certain embodiments, the conjugates have an average DAR of 1 to 1.5. In certain embodiments, the conjugates have an average DAR of 1.5 to 2. By average is meant the arithmetic mean.

Drugs to be conjugated to a polypeptide may be modified to incorporate a reactive partner for reaction with the polypeptide. Where the drug is a peptide drug, the reactive moiety (e.g., aminooxy or hydrazide can be positioned at an N-terminal region, the N-terminus, a C-terminal region, the C-terminus, or at a position internal to the peptide. For example, an example of a method involves synthesizing a peptide drug having an aminooxy group. In this example, the peptide is synthesized from a Boc-protected precursor. An amino group of a peptide can react with a compound comprising a carboxylic acid group and oxy-N-Boc group. As an example, the amino group of the peptide reacts with 3-(2,5-dioxopyrrolidin-1-yloxy)propanoic acid. Other variations on the compound comprising a carboxylic acid group and oxy-N-protecting group can include different number of carbons in the alkylene linker and substituents on the alkylene linker. The reaction between the amino group of the peptide and the compound comprising a carboxylic acid group and oxy-N-protecting group occurs through standard peptide coupling chemistry. Examples of peptide coupling reagents that can be used include, but not limited to, DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethylcarbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O—(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP-Cl (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate). As a non-limiting example, HOBt and DIC can be used as peptide coupling reagents.

Deprotection to expose the amino-oxy functionality is performed on the peptide comprising an N-protecting group. Deprotection of the N-oxysuccinimide group, for example, occurs according to standard deprotection conditions for a cyclic amide group. Deprotecting conditions can be found in Greene and Wuts, Protective Groups in Organic Chemistry, 3rd Ed., 1999, John Wiley & Sons, NY and Harrison et al. Certain deprotection conditions include a hydrazine reagent, amino reagent, or sodium borohydride. Deprotection of a Boc protecting group can occur with TFA. Other reagents for deprotection include, but are not limited to, hydrazine, methylhydrazine, phenylhydrazine, sodium borohydride, and methylamine. The product and intermediates can be purified by conventional means, such as HPLC purification.

The ordinarily skilled artisan will appreciate that factors such as pH and steric hindrance (i.e., the accessibility of the amino acid residue to reaction with a reactive partner of interest) are of importance, Modifying reaction conditions to provide for optimal conjugation conditions is well within the skill of the ordinary artisan, and is routine in the art. Where conjugation is conducted with a polypeptide present in or on a living cell, the conditions are selected so as to be physiologically compatible. For example, the pH can be dropped temporarily for a time sufficient to allow for the reaction to occur but within a period tolerated by the cell (e.g., from about 30 min to 1 hour). Physiological conditions for conducting modification of polypeptides on a cell surface can be similar to those used in a ketone-azide reaction in modification of cells bearing cell-surface azides (see, e.g., U.S. Pat. No. 6,570,040).

Small molecule compounds containing, or modified to contain, an X-nucleophilic group that serves as a reactive partner with a compound or conjugate disclosed herein are also contemplated for use as drugs in the polypeptide-drug conjugates of the present disclosure. General methods are known in the art for chemical synthetic schemes and conditions useful for synthesizing a compound of interest (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Formulations

The conjugates of the present disclosure can be formulated in a variety of different ways. In general, where the conjugate is an antibody-drug conjugate, the conjugate is formulated in a manner compatible with the drug, the antibody, the condition to be treated, and the route of administration to be used.

In some embodiments, provided is a pharmaceutical composition that includes any of the conjugates of the present disclosure and a pharmaceutically-acceptable excipient.

The conjugate (e.g., antibody-drug conjugate) can be provided in any suitable form, e.g., in the form of a pharmaceutically acceptable salt, and can be formulated for any suitable route of administration, e.g., oral, topical or parenteral administration. Where the conjugate is provided as a liquid injectable (such as in those embodiments where they are administered intravenously or directly into a tissue), the conjugate can be provided as a ready-to-use dosage form, or as a reconstitutable storage-stable powder or liquid composed of pharmaceutically acceptable carriers and excipients.

Methods for formulating conjugates can be adapted from those readily available. For example, conjugates can be provided in a pharmaceutical composition comprising a therapeutically effective amount of a conjugate and a pharmaceutically acceptable carrier (e.g., saline). The pharmaceutical composition may optionally include other additives (e.g., buffers, stabilizers, preservatives, and the like). In some embodiments, the formulations are suitable for administration to a mammal, such as those that are suitable for administration to a human.

Methods of Treatment

The antibody-drug conjugates of the present disclosure find use in treatment of a condition or disease in a subject that is amenable to treatment by administration of the parent drug (i.e., the drug prior to conjugation to the antibody).

In some embodiments, provided are methods that include administering to a subject an effective amount (e.g., a therapeutically effective amount) of any of the conjugates of the present disclosure.

In certain aspects, provided are methods of delivering a drug to a target site in a subject, the method including administering to the subject a pharmaceutical composition including any of the conjugates of the present disclosure, where the administering is effective to release a therapeutically effective amount of the drug from the conjugate at the target site in the subject. For example, as described herein, antibody-drug conjugates of the present disclosure can include a cleavable linker, such as an enzymatically cleavable linker that includes a first enzymatically cleavable moiety and a second enzymatically cleavable moiety. In some instances, the cleavable linker can be cleaved under appropriate conditions to separate or release the drug from the antibody at a desired target site of action for the drug. For example, the second cleavable linker, which protects the first cleavable linker from cleavage, may be cleaved in order to allow the first cleavable moiety to be cleaved, which results in cleavage of the cleavable linker into two or more portions, thus releasing the drug from the antibody-drug conjugate at a desired site of action.

In certain embodiments, the first cleavable moiety can be an enzymatically cleavable moiety. In some instances, the enzyme that facilitates cleavage of the first cleavable moiety is an enzyme that is administered to the subject to be treated (i.e., exogenous to the subject to be treated). For example, a first enzyme can be administered before, concurrently with, or after administration of an antibody-drug conjugate described herein.

In certain embodiments, the second cleavable moiety can be an enzymatically cleavable moiety. In some instances, the enzyme that facilitates cleavage of the second cleavable moiety is an enzyme that is administered to the subject to be treated (i.e., exogenous to the subject to be treated). For example, a second enzyme can be administered before, concurrently with, or after administration of an antibody-drug conjugate described herein. In certain embodiments, the first enzyme and the second enzyme are different enzymes.

In other instances, the first enzyme that facilitates cleavage of the first cleavable moiety is an enzyme that is present in the subject to be treated (i.e., endogenous to the subject to be treated). For instance, the first enzyme may be present at the desired site of action for the drug of the antibody-drug conjugate. The antibody of the antibody-drug conjugate may be specifically targeted to a desired site of action (e.g., may specifically bind to an antigen present at a desired site of action), where the desired site of action also includes the presence of the first enzyme. In some instances, the first enzyme is present in an overabundance at the desired site of action as compared to other areas in the body of the subject to be treated. For example, the first enzyme may be overexpressed at the desired site of action as compared to other areas in the body of the subject to be treated. In some instances, the first enzyme is present in an overabundance at the desired site of action due to localization of the first enzyme at a particular area or location. For instance, the first enzyme may be associated with a certain structure within the desired site of action, such as lysosomes. In some cases, the first enzyme is present in an overabundance in lysosomes as compared to other areas in the body of the subject. In some embodiments, the lysosomes that include the first enzyme, are found at a desired site of action for the drug of the antibody-drug conjugate, such as the site of a cancer or tumor that is to be treated with the drug. In certain embodiments, the first enzyme is a protease, such as a human protease enzyme (e.g., cathepsin B).

In certain embodiments, the second enzyme that facilitates cleavage of the second cleavable moiety is an enzyme that is present in the subject to be treated (i.e., endogenous to the subject to be treated). For instance, the second enzyme may be present at the desired site of action for the drug of the antibody-drug conjugate. The antibody of the antibody-drug conjugate may be specifically targeted to a desired site of action (e.g., may specifically bind to an antigen present at a desired site of action), where the desired site of action also includes the presence of the second enzyme. In some instances, the second enzyme is present in an overabundance at the desired site of action as compared to other areas in the body of the subject to be treated. For example, the second enzyme may be overexpressed at the desired site of action as compared to other areas in the body of the subject to be treated. In some instances, the second enzyme is present in an overabundance at the desired site of action due to localization of the second enzyme at a particular area or location. For instance, the second enzyme may be associated with a certain structure within the desired site of action, such as lysosomes. In some cases, the second enzyme is present in an overabundance in lysosomes as compared to other areas in the body of the subject. In some embodiments, the lysosomes that include the second enzyme, are found at a desired site of action for the drug of the antibody-drug conjugate, such as the site of a cancer or tumor that is to be treated with the drug. In certain embodiments, the second enzyme is a glycosidase, such as a galactosidase, a glucosidase, a mannosidase, a fucosidase, and the like.

Any suitable enzymes can be used for cleavage of the first cleavable moiety and the second cleavable moiety of the antibody-drug conjugates described herein. Other enzymes may also be suitable for use in cleavage of the first cleavable moiety and the second cleavable moiety of the antibody-drug conjugates described herein, such as but not limited to, enzymes from other vertebrates (e.g., primates, mice, rats, cats, pigs, quails, goats, dogs, etc.).

In certain embodiments, the antibody-drug conjugate is substantially stable under standard conditions. By substantially stable is meant that the cleavable linker of the antibody-drug conjugate does not undergo a significant amount of cleavage in the absence of a first enzyme and a second enzyme as described above. For example, as described above, the second cleavable moiety can protect the first cleavable moiety from being cleaved, and as such the cleavable linker of the antibody-drug conjugate does not undergo a significant amount of cleavage in the absence of a second enzyme as described above. For instance, the cleavable linker of the antibody-drug conjugate may be substantially stable such that 25% or less of the antibody-drug conjugate is cleaved in the absence of the first enzyme and/or second enzyme, such as 20% or less, or 15% or less, or 10% or less, or 5% or less, or 4% or less, or 3% or less, or 2% or less, or 1% or less. In some cases, the antibody-drug conjugate is substantially stable such that the cleavable linker of the antibody-drug conjugate does not undergo a significant amount of cleavage in the absence of the first enzyme and/or second enzyme, but can be cleaved when in the presence of the first enzyme and the second enzyme. For example, the antibody-drug conjugate can be substantially stable after administration to a subject. In some cases, the antibody-drug conjugate is substantially stable after administration to a subject, and then, when the antibody-drug conjugate is in the presence of the second enzyme at a desired site of action, the second cleavable moiety can be cleaved from the cleavable linker, thus exposing the first cleavable moiety to subsequent cleavage by the first enzyme, which in turn releases the drug at the desired site of action. In certain embodiments, after administration to a subject the antibody-drug conjugate is stable for an extended period of time in the absence of the first enzyme and/or second enzyme, such as 1 hr or more, or 2 hrs or more, or 3 hrs or more, or 4 hrs or more, or 5 hrs or more, or 6 hrs or more, or 7 hrs or more, or 8 hrs or more, or 9 hrs or more, or 10 hrs or more, or 15 hrs or more, or 20 hrs or more, or 24 hrs (1 day) or more, or 2 days or more, or 3 days or more, or 4 days or more, or 5 days or more, or 6 days or more, or 7 days (1 week) or more. In certain embodiments, the antibody-drug conjugate is stable at a range pH values for an extended period of time in the absence of the first enzyme and/or second enzyme, such as at a pH ranging from 2 to 10, or from 3 to 9, or from 4 to 8, or from 5 to 8, or from 6 to 8, or from 7 to 8.

As described above, the antibody-drug conjugates of the present disclosure find use in treatment of a condition or disease in a subject that is amenable to treatment by administration of the parent drug. By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

The subject to be treated can be one that is in need of therapy, where the subject to be treated is one amenable to treatment using the parent drug. Accordingly, a variety of subjects may be amenable to treatment using the antibody-drug conjugates disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees and monkeys).

The amount of antibody-drug conjugate administered can be initially determined based on guidance of a dose and/or dosage regimen of the parent drug. In general, the antibody-drug conjugates can provide for targeted delivery and/or enhanced serum half-life of the bound drug, thus providing for at least one of reduced dose or reduced administrations in a dosage regimen. Thus, the antibody-drug conjugates can provide for reduced dose and/or reduced administration in a dosage regimen relative to the parent drug prior to being conjugated in an antibody-drug conjugate of the present disclosure.

Furthermore, as noted above, because the antibody-drug conjugates can provide for controlled stoichiometry of drug delivery, dosages of antibody-drug conjugates can be calculated based on the number of drug molecules provided on a per antibody-drug conjugate basis.

In some embodiments, multiple doses of an antibody-drug conjugate are administered. The frequency of administration of an antibody-drug conjugate can vary depending on any of a variety of factors, e.g., severity of the symptoms, condition of the subject, etc. For example, in some embodiments, an antibody-drug conjugate is administered once per month, twice per month, three times per month, every other week, once per week (qwk), twice per week, three times per week, four times per week, five times per week, six times per week, every other day, daily (qd/od), twice a day (bds/bid), or three times a day (tds/tid), etc.

Methods of Treating Cancer

The present disclosure provides methods that include delivering a conjugate of the present disclosure to an individual having a cancer. The methods are useful for treating a wide variety of cancers, including carcinomas, sarcomas, leukemias, and lymphomas. In the context of cancer, the term "treating" includes one or more (e.g., each) of: reducing growth of a solid tumor, inhibiting replication of cancer cells, reducing overall tumor burden, and ameliorating one or more symptoms associated with a cancer.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's B cell lymphoma; and the like.

In certain aspects, provided are methods of treating cancer in a subject, such methods including administering to the subject a therapeutically effective amount of a pharmaceutical composition including any of the conjugates of the present disclosure, where the administering is effective to treat cancer in the subject.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Example 1

Galactoside and Glucoside Dual-Cleavage Linkers for Antibody-Drug Conjugates

Introduction

The utility of glucuronide-dipeptide dual-cleavage linkers has been demonstrated, for example in Scheme 1 below, where MMAE construct 4 bearing Val-Ala-PABC linker with glucuronide moiety attached to the self-immolating unit, upon conjugation with an antibody provided an antibody-drug conjugate (ADC) with superior stability but similar efficacy in vivo, compared to the generic dipeptide MMAE drug-linker. Glucuronide-based MMAE construct was synthesized as shown in Scheme 1 in 10 synthetic steps and good overall yield. This synthesis started from fully protected β-glucuronic acid bromide that was commercially available. The required global deprotection of all acetate groups in the glucuronide moiety of intermediate 3, as well as the cleavage of the methyl ester was accomplished by hydrolysis under strong basic conditions (LiOH in methanol).

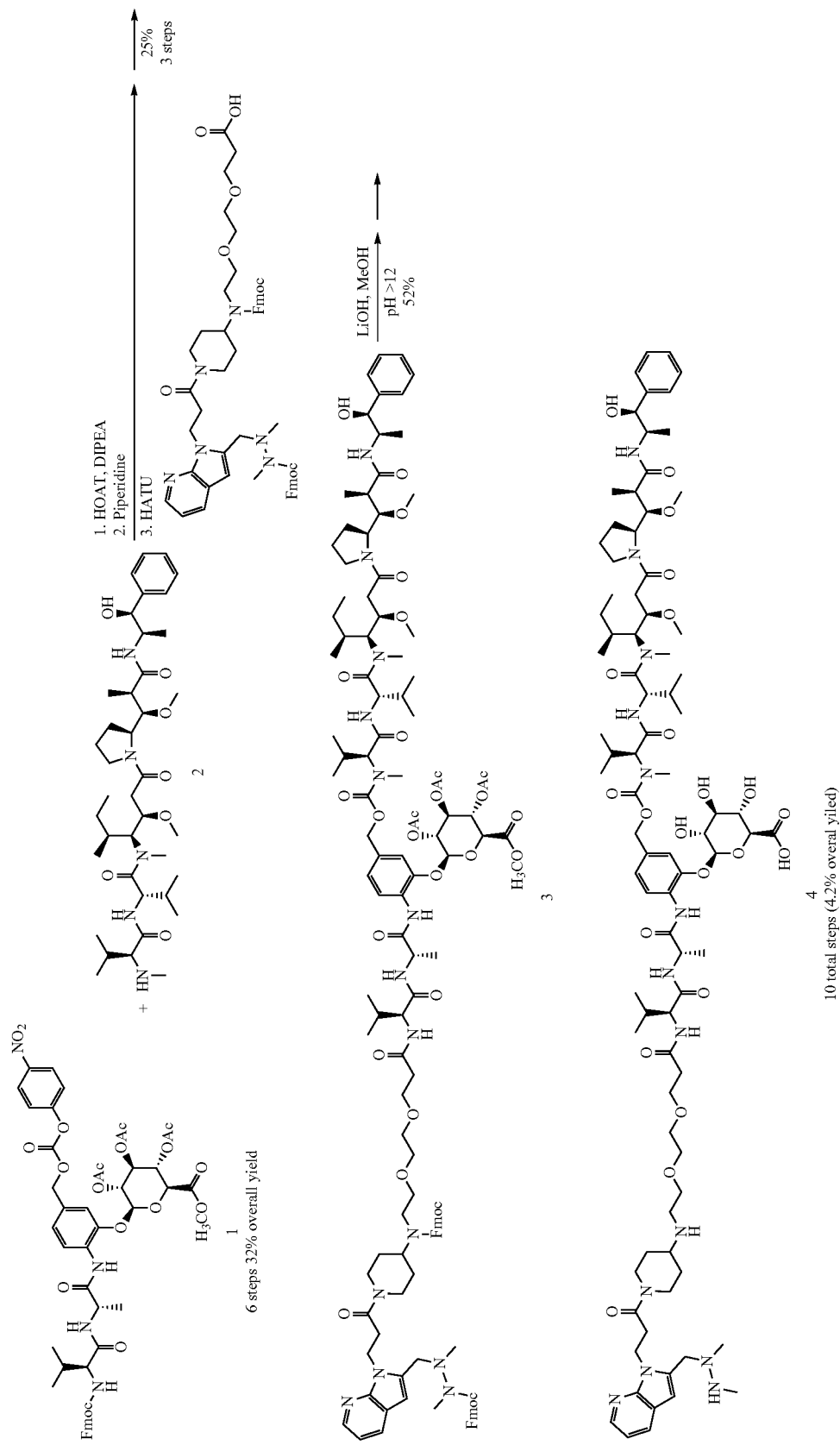
Scheme 1. P1'-Glucuronide dual-cleavage MMAE construct 4.

Although these strong basic conditions were compatible with the MMAE drug (that is not particularly sensitive to strong base), the requirement of basic hydrolysis in the last step of the synthesis significantly limited the application of glucuronide-based dual-cleavage linkers. In fact, a variety of cytotoxins frequently used for generating antibody-drug conjugates contain base-labile functional groups (FIG. 1). For instance, the primary alkyl chloride and amide groups in Duocarmycin DM 5 are highly susceptible to basic hydrolysis, as are the acetate group in Tubulysin M 6, and the ester functions in Calicheamicin 7. Maytansinoids 8 and 9 are particularly unstable under basic conditions because their structures contain esters and an epoxide. Similarly, lactones in DNA topoisomerase I inhibitors, such as SN-38 10 and Exatecan 11, are known to hydrolyze even under mildly basic conditions.

Despite the aforementioned compatibility issues, we previously showed that certain maytansinoids, such as 4AP-maytansine 9 (FIG. 1), could still be paired with glucuronide-based linkers, however, synthesis towards such constructs was laborious and inefficient (17 steps, 1.8% overall yield, Scheme 2). In this synthetic route, the glucuronide linker 12 had to be prepared separately and brought into the synthetic sequence at a late stage in a fully deprotected form to react with a separately synthesized maytansine derivative 13.

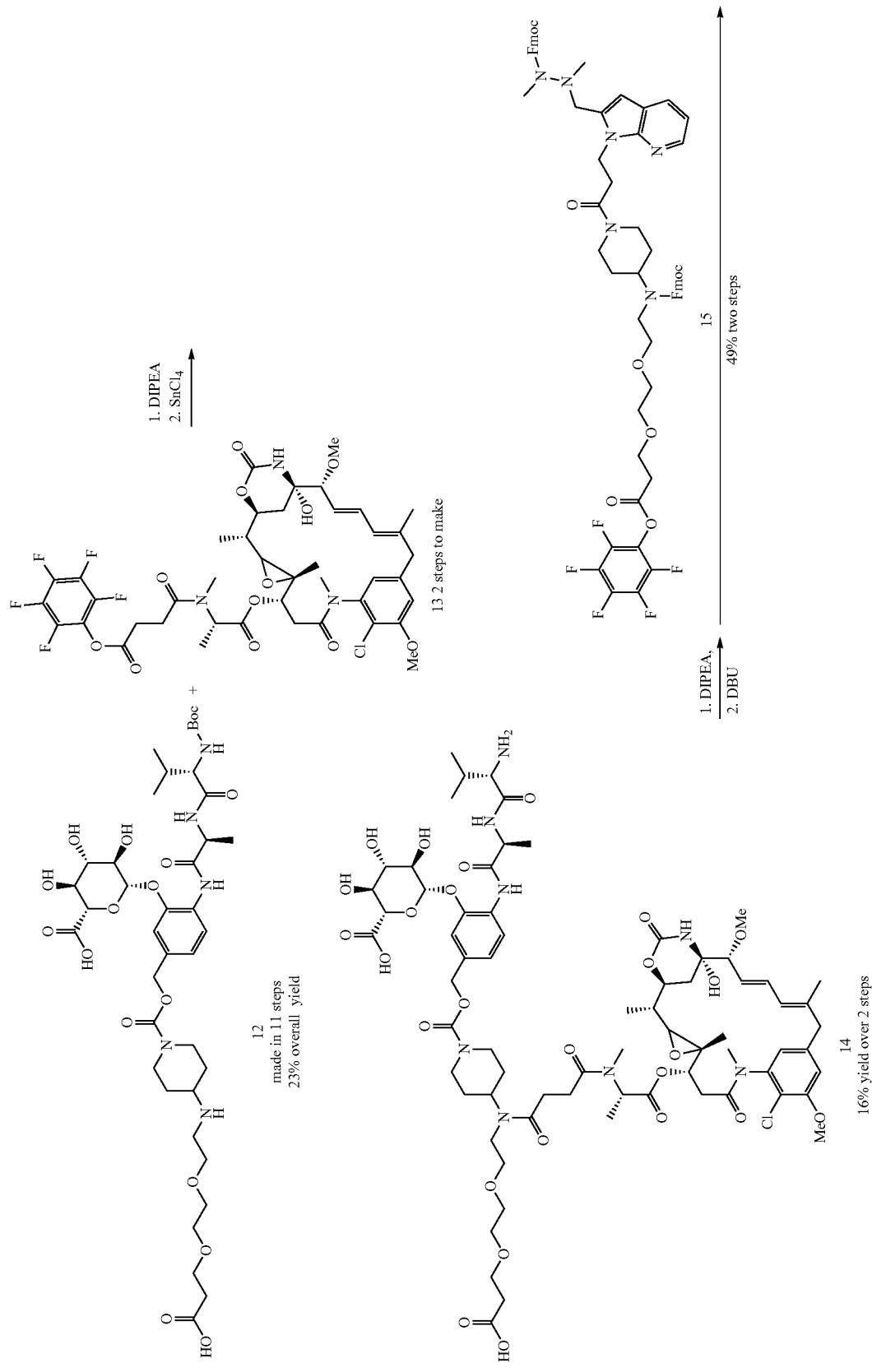

-continued
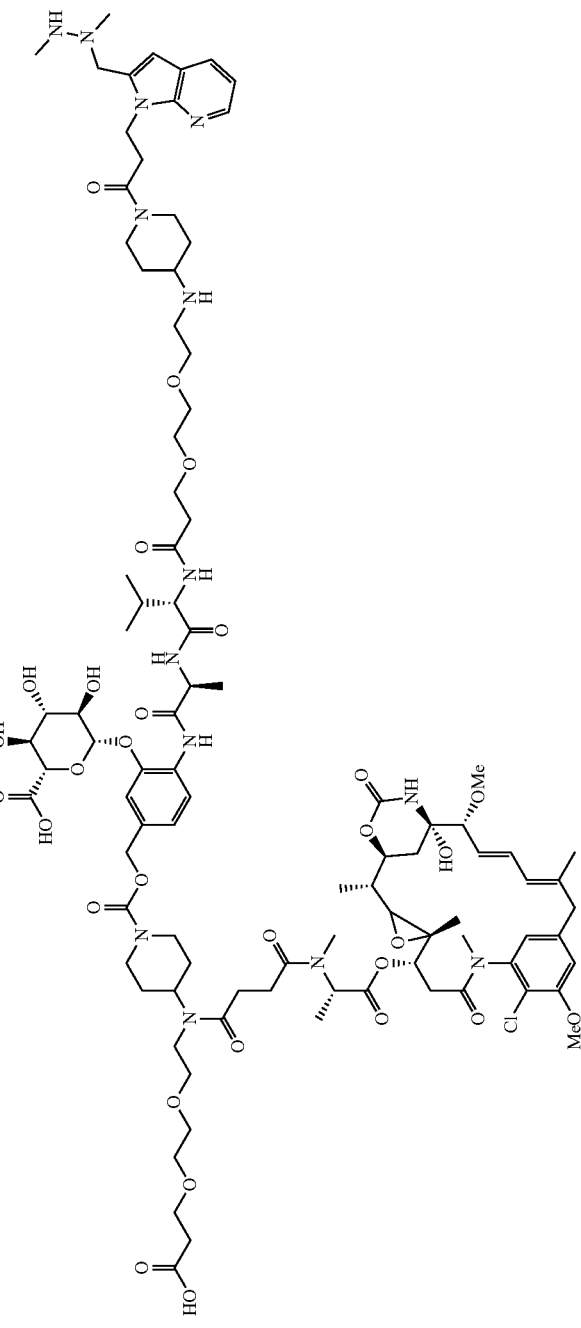
P1'-Glucuronide 4AP-Matansine construct 16
17 total steps
1.8% total yield While this particular maytansinoid (9) was somewhat amenable to synthetic modifications, the more attractive NMC3-Maytansine (8) would not be possible to use in a similar fashion due to its structural elements. If the synthetic strategy used for 9 (Scheme 2) is utilized for 8, one would inevitably face the selectivity problem of differentiating between the two carboxylic groups in glucuronic acid intermediate 18 (Scheme 3) at the late stage of the synthesis, and would require an alternative and lengthy protection-deprotection approach.

Results and Discussion

In contrast to the examples described in the Introduction, when a different biologically relevant glycoside was used in the dual-cleavage linker, a larger scope of cytotoxins can successfully be employed in the synthesis. Thus, using a galactoside in place of glucuronide allowed the use of NMC3-Maytansine (8, FIG. 1) and the generation of the P1'-galactoside construct 30 in good overall yield (7.5%) in Scheme 3. Synthetic approach to P1'-Glucuronide NMC3-Maytansine construct 19 (not feasible due to the presence of free carboxylic acid in glucuronide moiety).

P1'-Glucuronide NMC3-Maytansine
19

11 synthetic steps (Scheme 4). The galactoside moiety in its completely unprotected form, due to the absence of carboxylic group (as in compound 29, Scheme 4), posed no chemoselectivity problem and can successfully be utilized with a large number of base-sensitive ADC payloads. The same is expected to be true for glucosides and mannosides as their structures are not significantly different from galactosides.

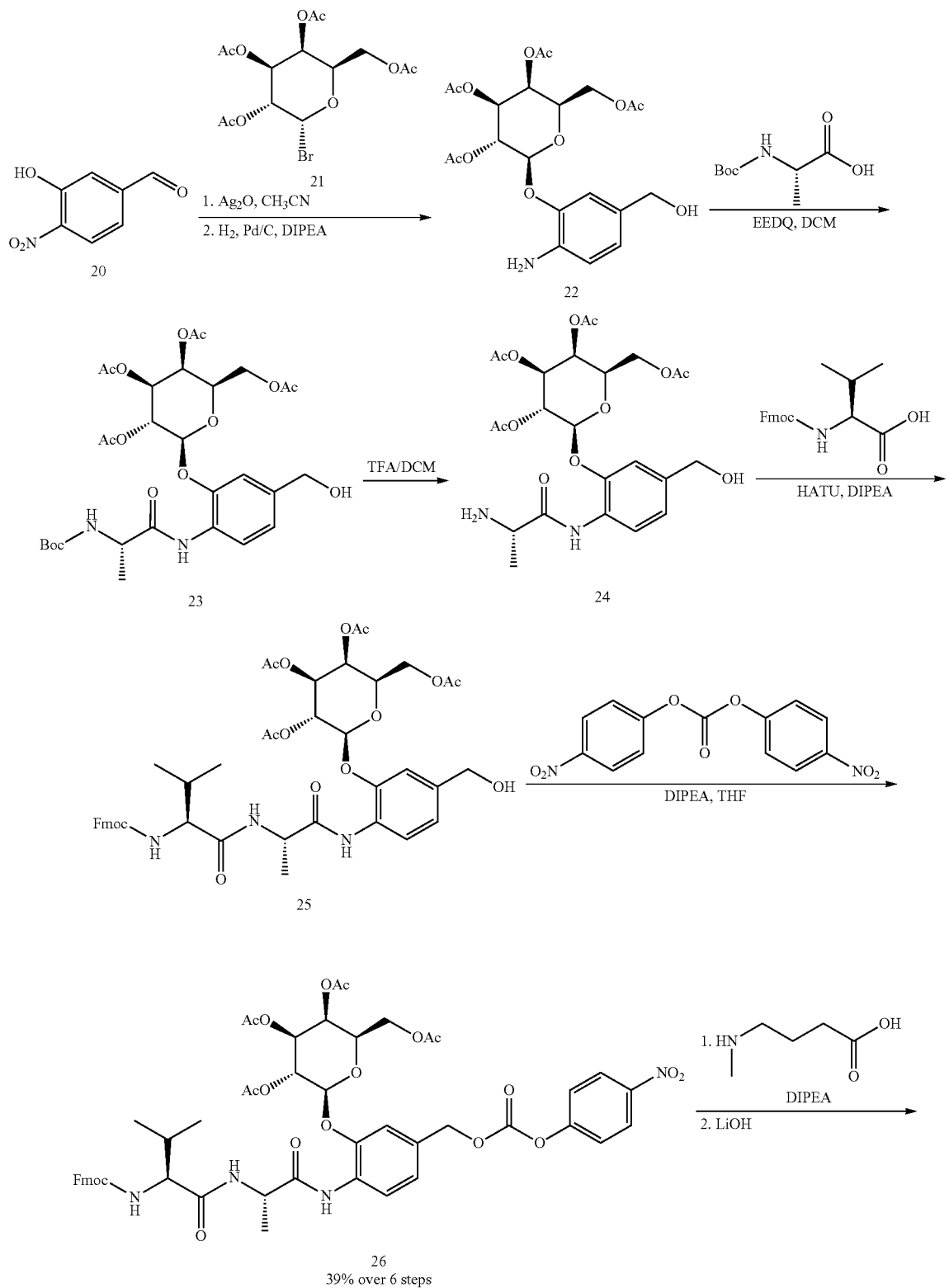

Scheme 4. Synthesis of P1′-galactoside NMC3-Maytansine construct 30.

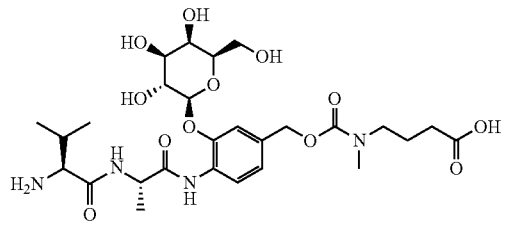
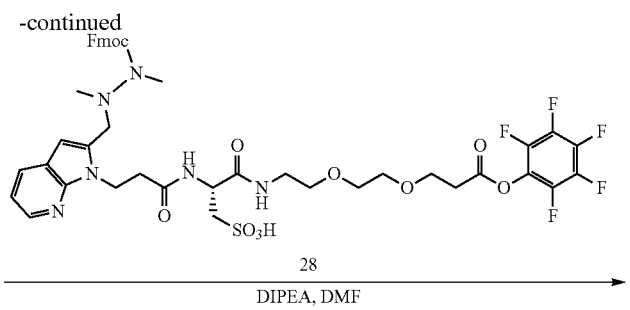
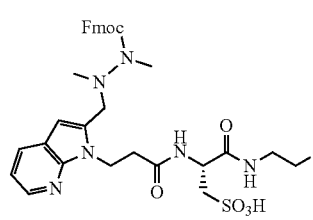
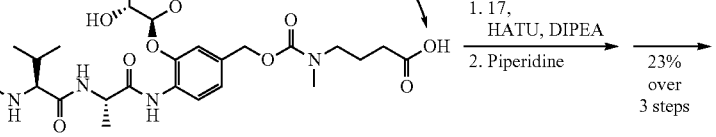
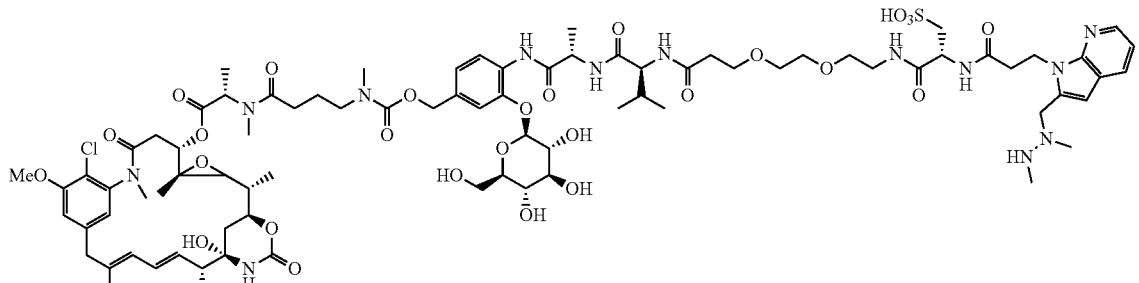

Indeed, similar to galactosides, other monosaccharide derivatives of base-sensitive payloads useful for generating ADCs can be prepared. Thus, a dual-cleavage glucoside linker was successfully paired with a NMC3-Maytansine payload to furnish the corresponding construct 44 in good overall yield (4.9% over 11 steps) as shown in Scheme 5.

Scheme 5. Synthesis of P1′-glucoside NMC3-Maytansine construct 44.

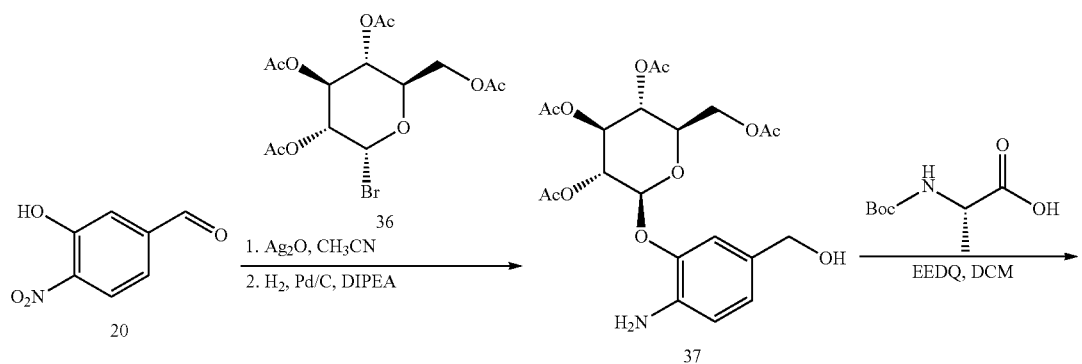

-continued
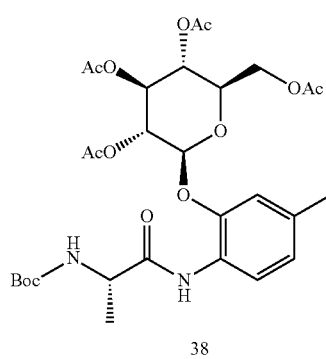
38
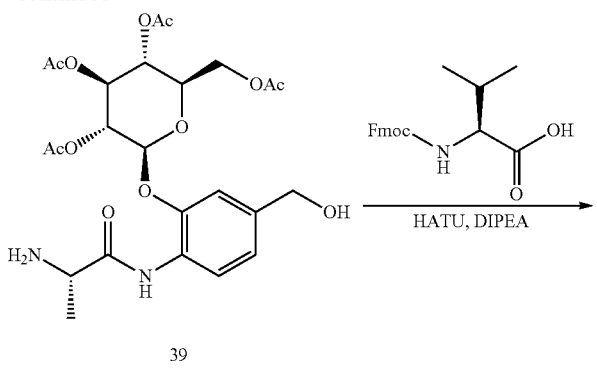
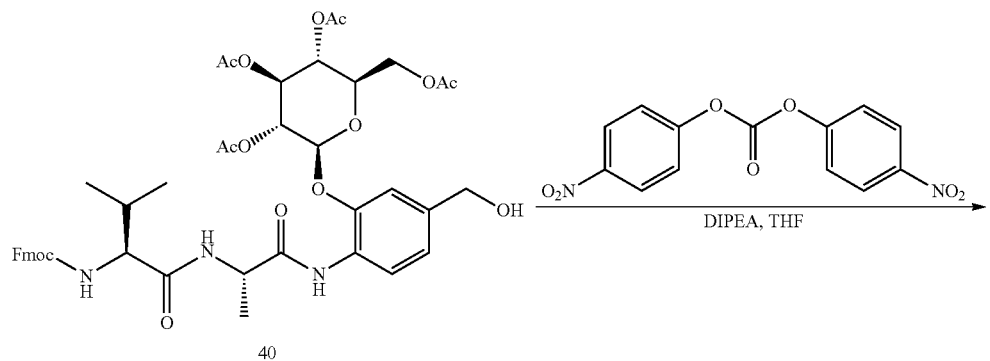
40
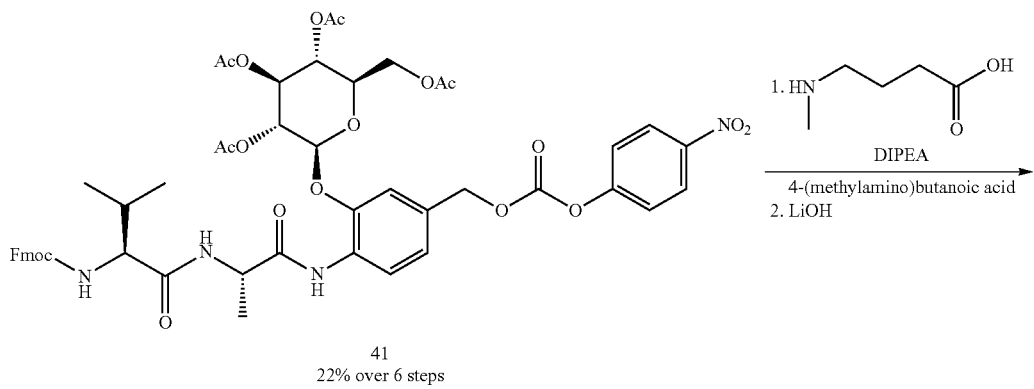
41
22% over 6 steps
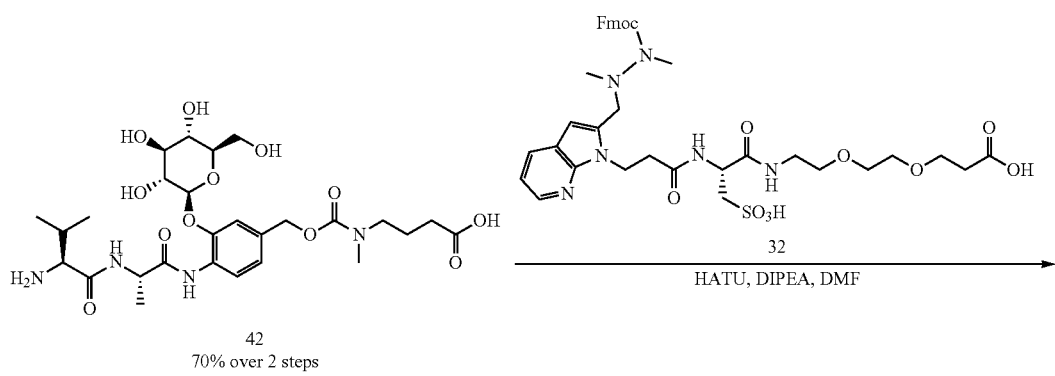
42
70% over 2 steps

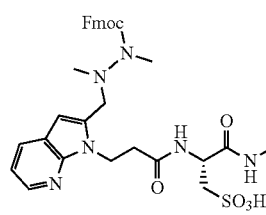
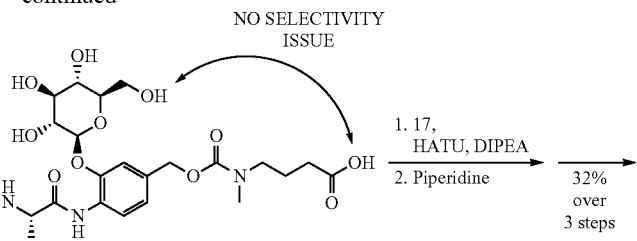
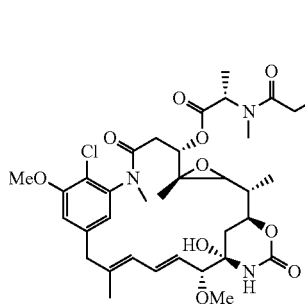

43

44
11 total steps
4.9% overall yield

Moreover, it was found that utilizing galactoside or glucoside allowed for consistently more efficient and high yielding synthesis of drug-linkers as compared to the glucuronide counterparts. Thus, the synthetic route to the P1'-galactoside MMAE construct 33 shown in the Scheme 6 produced the desired compound in excellent overall yield (9.4% vs 4.2% for the glucuronide construct, Table 1).

Scheme 6. Synthesis of P1'-galactoside MMAE construct 33.
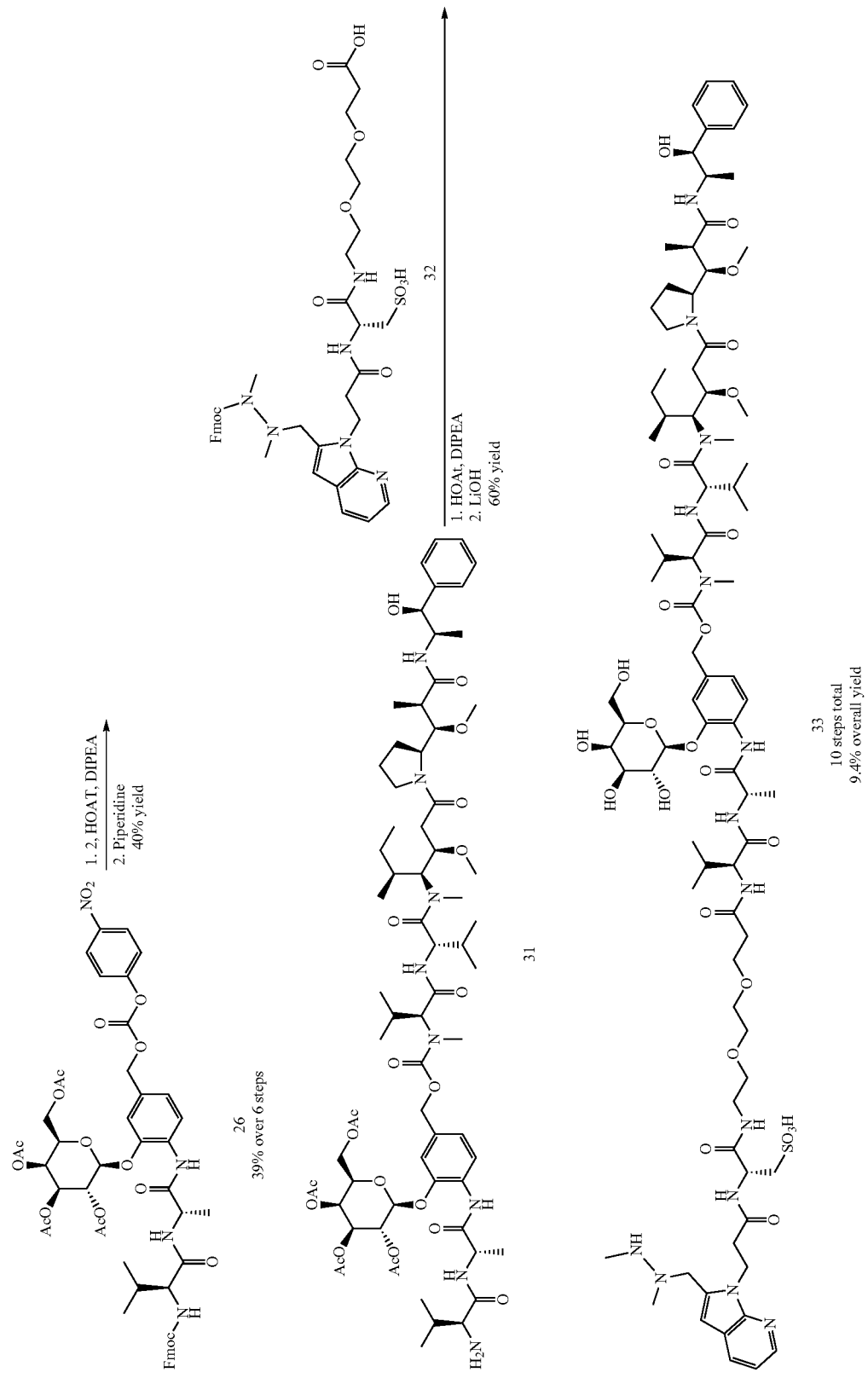

Similarly, the glucoside congener 46 was prepared following a modified synthetic route (Scheme 7) starting from the corresponding monosaccharide derivative 41 in a more efficient manner when compared to the glucuronide-bearing compound 4 (7.6% yield vs 4.2% for the glucuronide 5 construct, Table 1).

Scheme 7. Synthesis of glucoside MMAE construct 46.
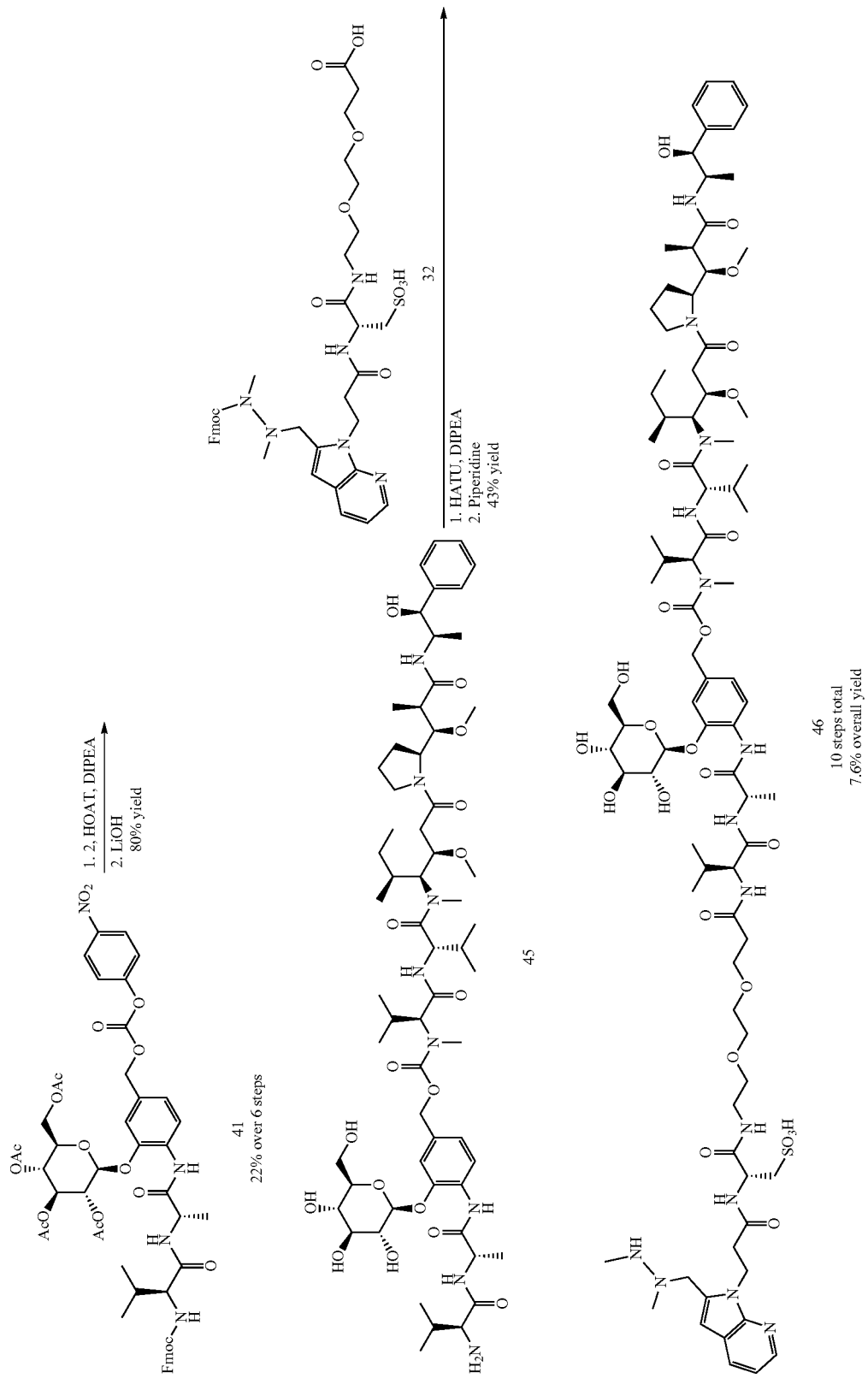

Furthermore, a comparison of materials cost revealed that on average the required galactose and glucose derivatives were 10-20 times less expensive than the corresponding glucuronic acid derivative (see Table 1).

TABLE 1

Comparison of synthesis efficiency and cost depending on the type of glycoside used.

| Entry | Construct | Cytotoxin | Glycoside type | Synthesis # of steps | Overall yield, % | Cost of glycoside* |
|---|---|---|---|---|---|---|
| 1 | 4 | MMAE | Glucuronide | 10 | 4.2 | 25 g/$740 |
| 2 | 16 | 4AP-Maytansine | Glucuronide | 17 | 1.8 | 25 g/$740 |
| 3 | 19 | NMC3-Maytansine | Glucuronide | Not feasible | | 25 g/$740 |
| 4 | 30 | NMC3-Maytansine | Galactoside | 11 | 7.5 | 100 g/$280 |
| 5 | 33 | MMAE | Galactoside | 10 | 9.4 | 100 g/$280 |
| 6 | 44 | NMC3-Maytansine | Glucoside | 11 | 4.9 | 500 g/$800 |
| 7 | 46 | MMAE | Glucoside | 10 | 7.6 | 500 g/$800 |

*Cost of acetate-protected bromide derivatives of glucuronic acid, galactose, and glucose (AK Scientific catalog, September 2020)

Figure 2:
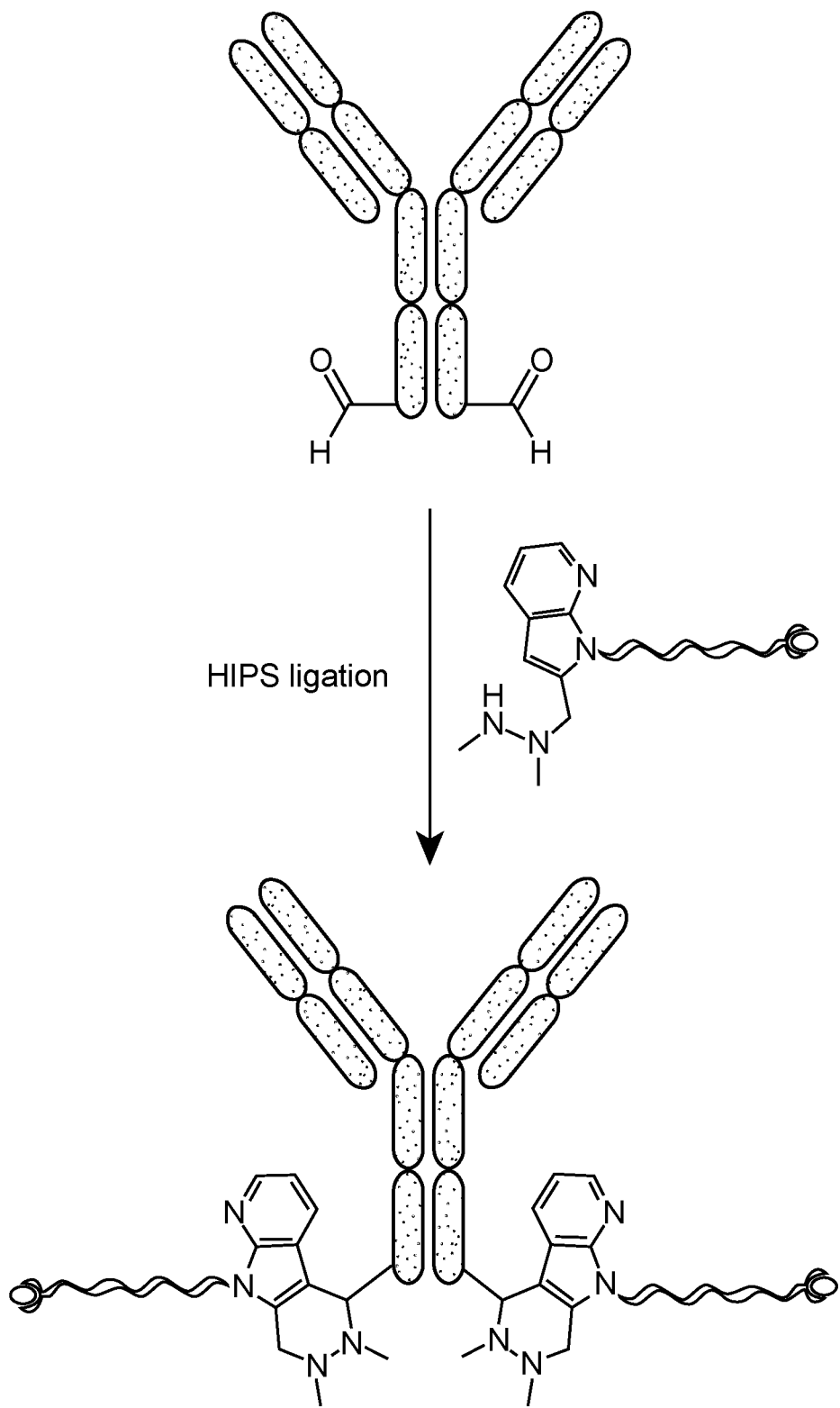
FIG. 2 shows HIPS ligation for the synthesis of antibody-drug conjugates (ADCs). Antibodies carrying aldehyde moieties were reacted with a Hydrazino-iso-Pictet-Spengler (HIPS) linker and payload to generate a site-specifically conjugated ADC with a stable azacarboline linkage.
Figure 3:
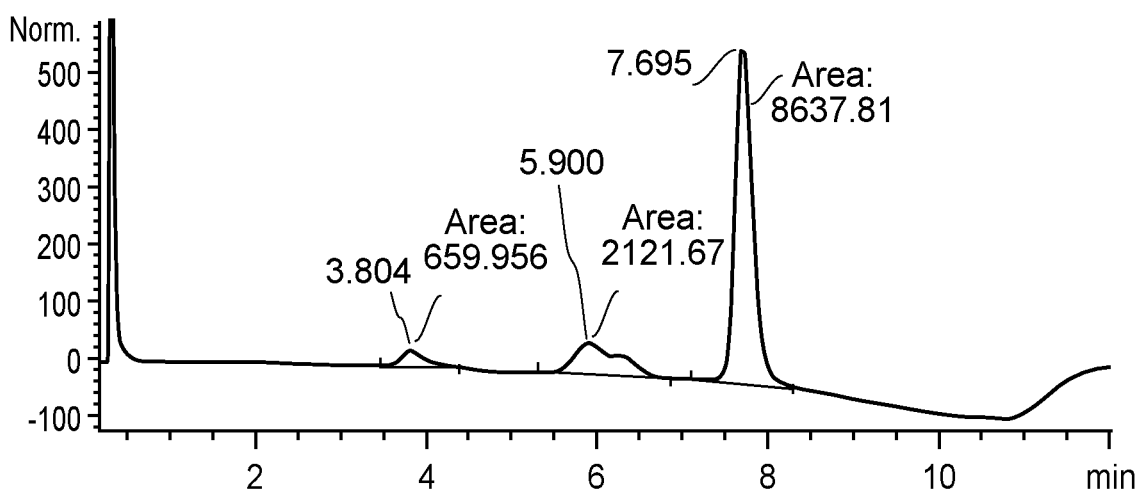
FIG. 3 shows a hydrophobic interaction column (HIC) trace of construct 30 trastuzumab conjugate, which yielded a DAR of 1.7 as determined by HIC.
Figure 4:
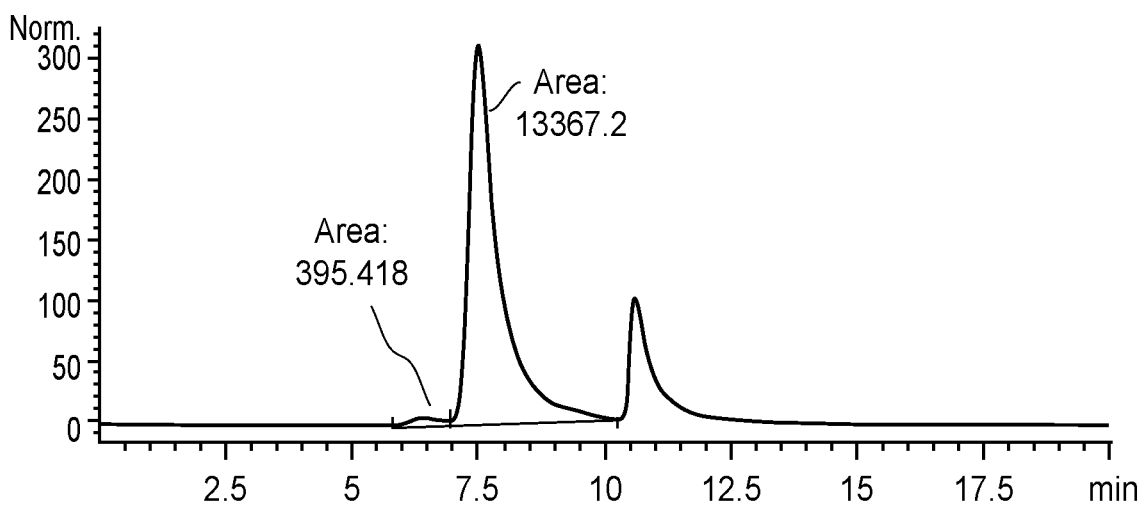
FIG. 4 shows an analytical size exclusion chromatography (SEC) trace of construct 30 trastuzumab conjugate, which indicated that the conjugate was 97.1% monomeric as determined by analytical SEC.
Figure 5:
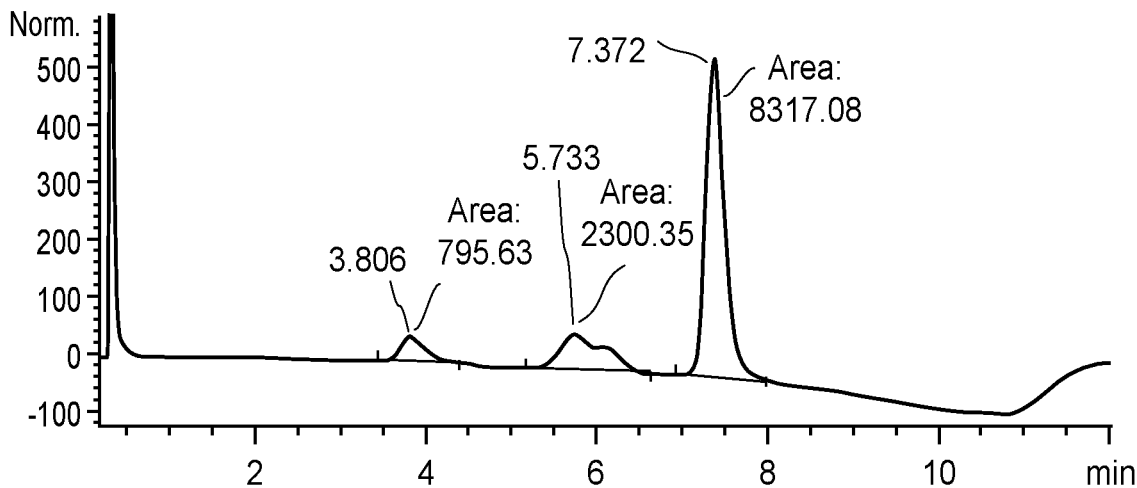
FIG. 5 shows an HIC trace of construct 33 trastuzumab conjugate, which yielded a DAR of 1.66 as determined by HIC.
Figure 6:
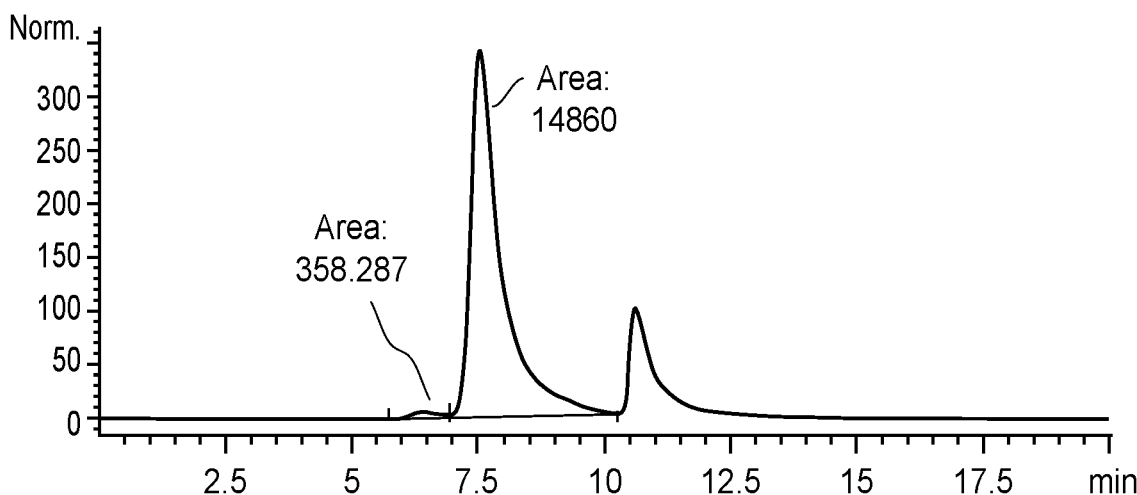
FIG. 6 shows an analytical SEC trace of construct 33 trastuzumab conjugate, which indicated that the conjugate was 97.6% monomeric as determined by analytical SEC.
Figure 7:
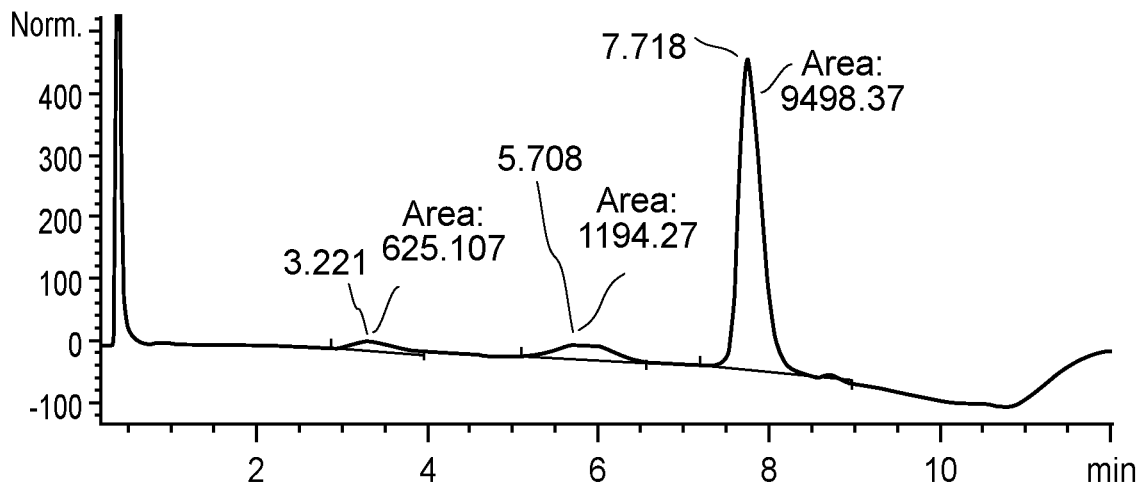
FIG. 7 shows an HIC trace of construct 30 polatuzumab conjugate, which yielded a DAR of 1.78 as determined by HIC.
Figure 8:
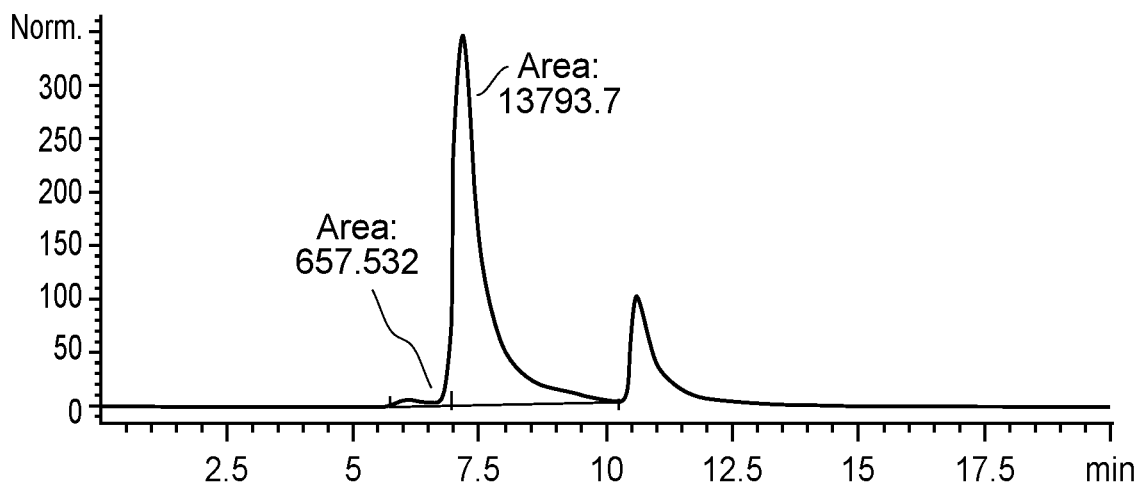
FIG. 8 shows an analytical SEC trace of construct 30 polatuzumab conjugate, which indicated that the conjugate was 95.4% monomeric as determined by analytical SEC.
Figure 9:
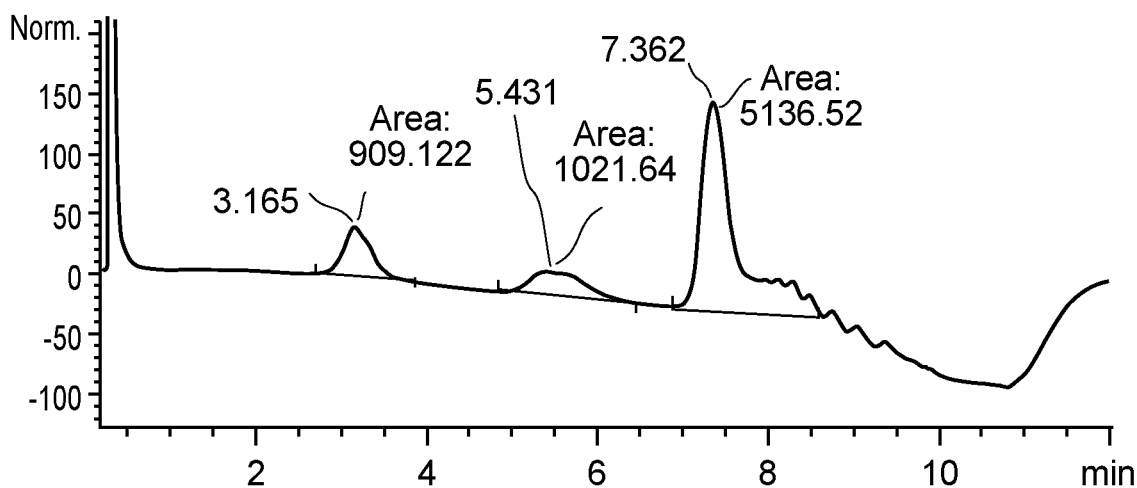
FIG. 9 shows an HIC trace of construct 33 polatuzumab conjugate, which yielded a DAR of 1.6 as determined by HIC.
Figure 10:
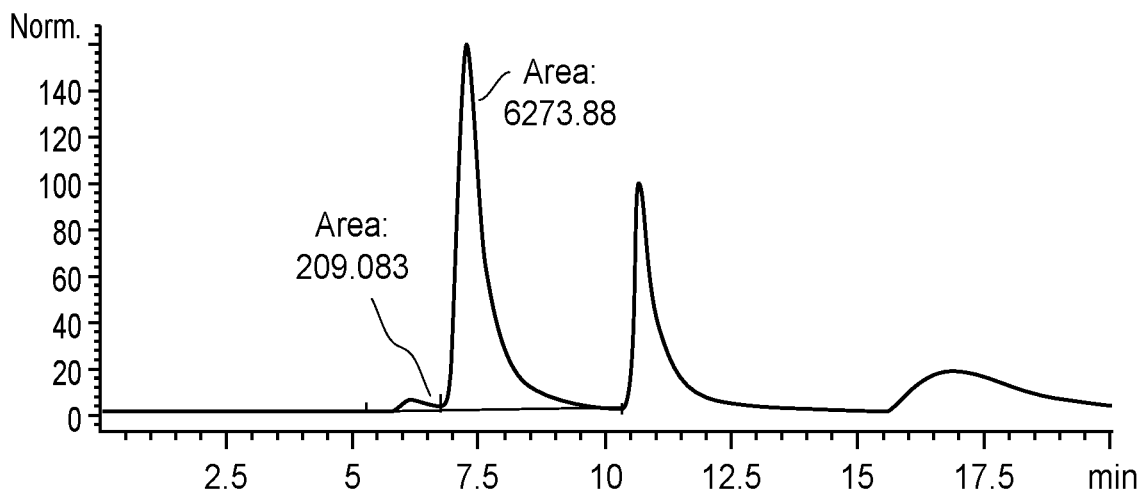
FIG. 10 shows an analytical SEC trace of construct 33 polatuzumab conjugate, which indicated that the conjugate was 96.8% monomeric as determined by analytical SEC.

When incorporated into a linker in proximity to an enzymatically-cleavable dipeptide, glycosides can serve as temporary protecting groups that prevent premature cleavage of the antibody-drug conjugate dipeptide linker in circulation. Once the ADC is trafficked into the lysosomal compartment of a cell, the glycoside moiety must be cleaved by lysosomal glycosidases to expose the dipeptide linker, which, in turn undergoes enzyme-mediated cleavage to release the payload. There are a number of human glycosidases, with different substrate preferences and distinct cell and tissue expression patterns. Whereas we had previously shown that a glucuronide moiety could be efficiently removed in a broad variety of cell types as a first step towards achieving payload liberation, it was not clear whether galactoside or glucoside moieties would be processed similarly or not. To address this question, constructs 30 and 33 were conjugated using HIPS ligation with aldehyde-tagged anti-HER2 and anti-CD79b antibodies, and constructs 44 and 46 were conjugated using HIPS ligation with aldehyde-tagged anti-FITC, anti-HER2, and anti-TROP-2 antibodies (FIG. 2). Analytical characterization of the resulting conjugates is shown in FIGS. 3-10 and 19-30.

Figure 11:
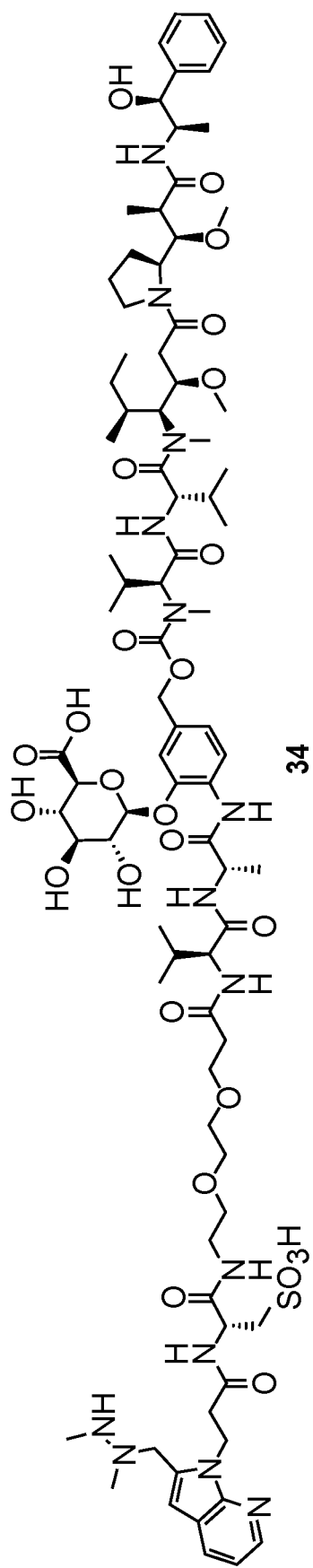
FIG. 11 shows structures of comparator molecules 35 (mono-cleavage Maytansine construct) and 34 (glucuronide dual-cleavage MMAE construct).
Figure 11:
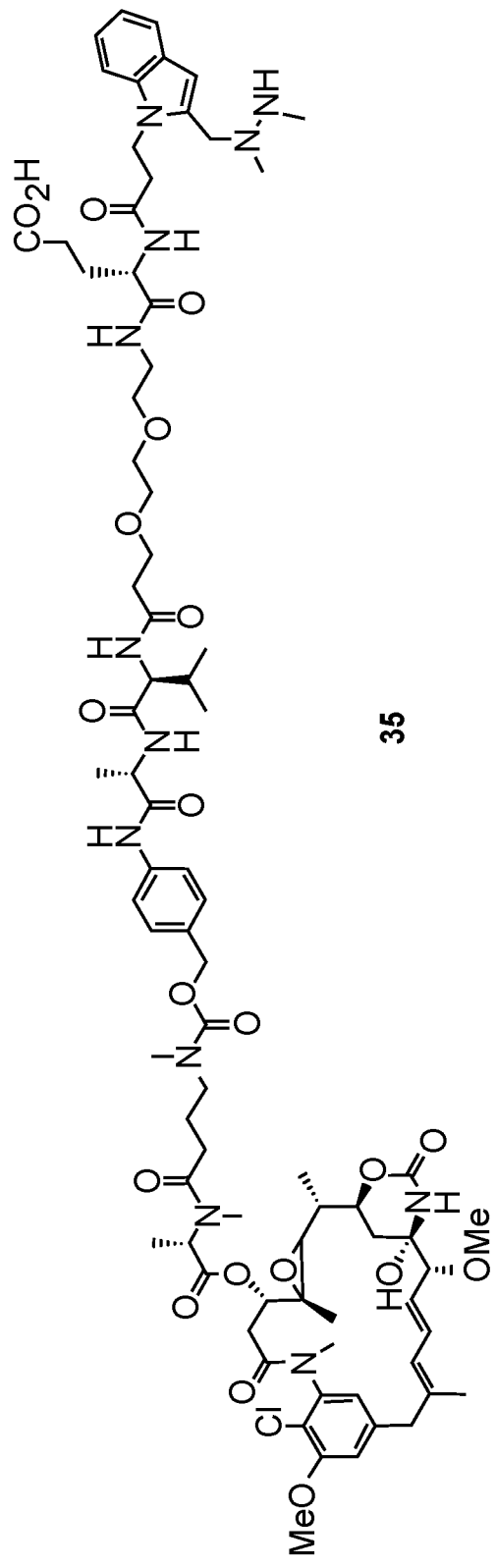
Figure 12:
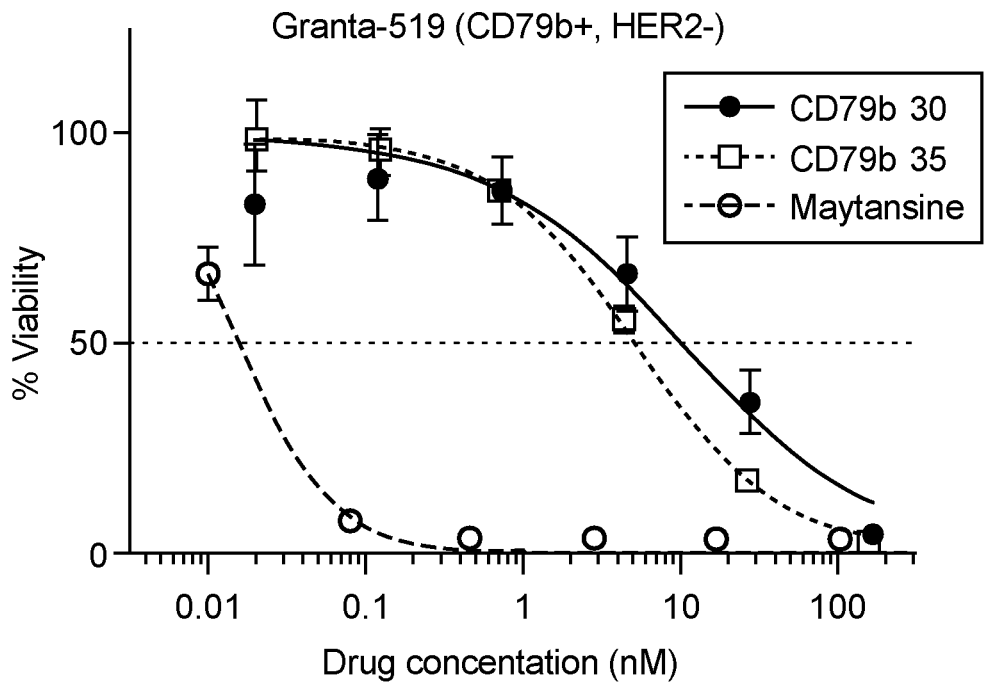
FIG. 12 shows a graph of in vitro potency of maytansine-conjugated ADCs carrying mono-cleavage (35) or galactoside-modified dual-cleavage linkers (30) against Granta-519 cells.
Figure 13:
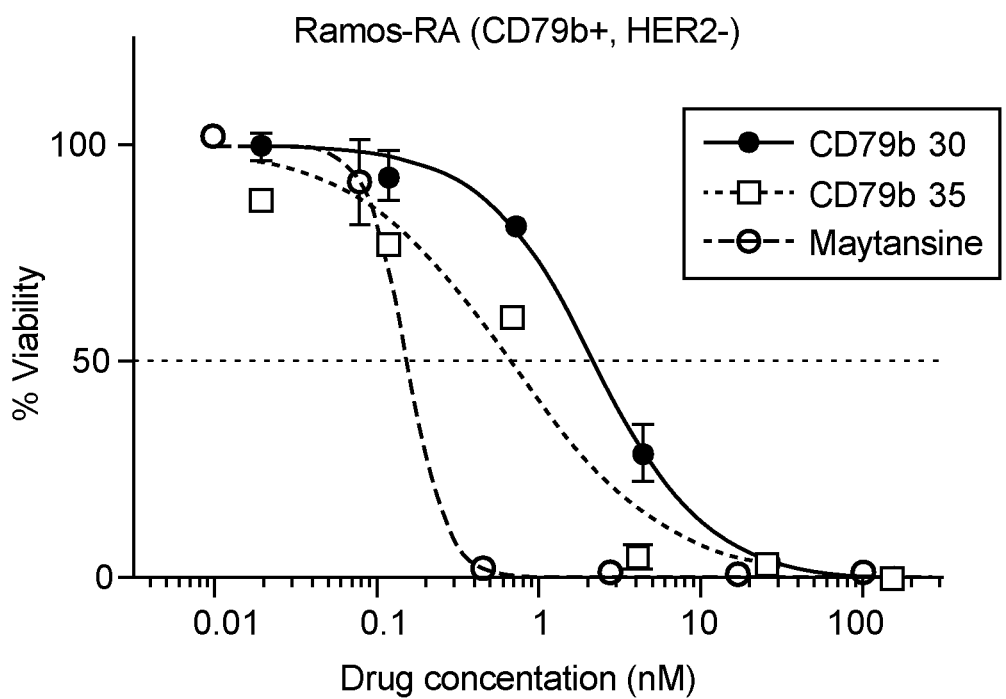
FIG. 13 shows a graph of in vitro potency of maytansine-conjugated ADCs carrying mono-cleavage (35) or galactoside-modified dual-cleavage linkers (30) against Ramos-RA cells.
Figure 14:
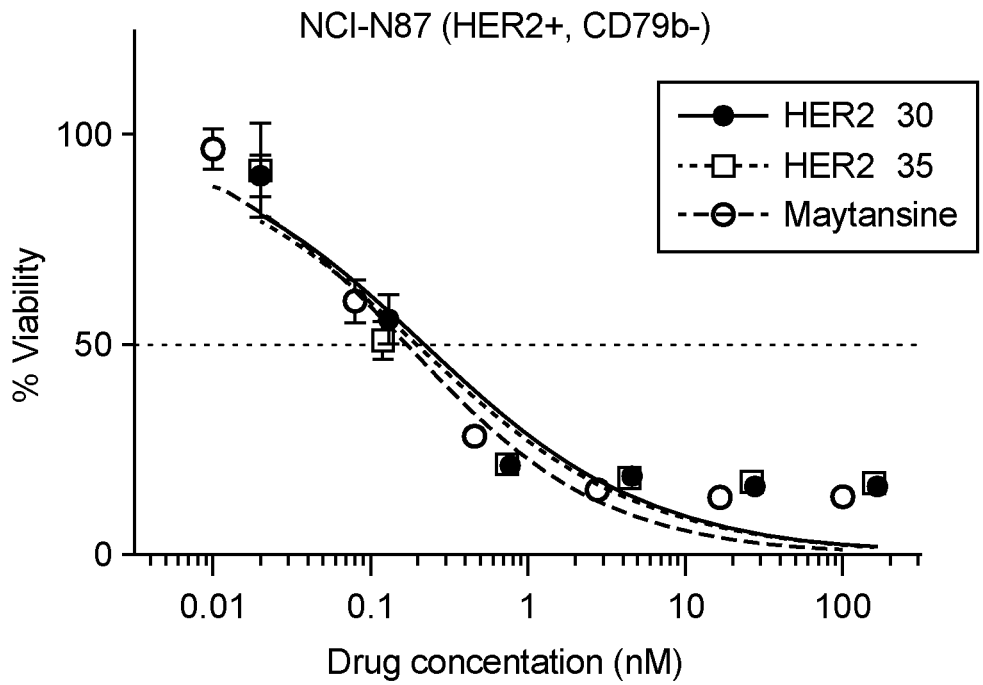
FIG. 14 shows a graph of in vitro potency of maytansine-conjugated ADCs carrying mono-cleavage (35) or galactoside-modified dual-cleavage linkers (30) against NCI-N87 cells.
Figure 15:
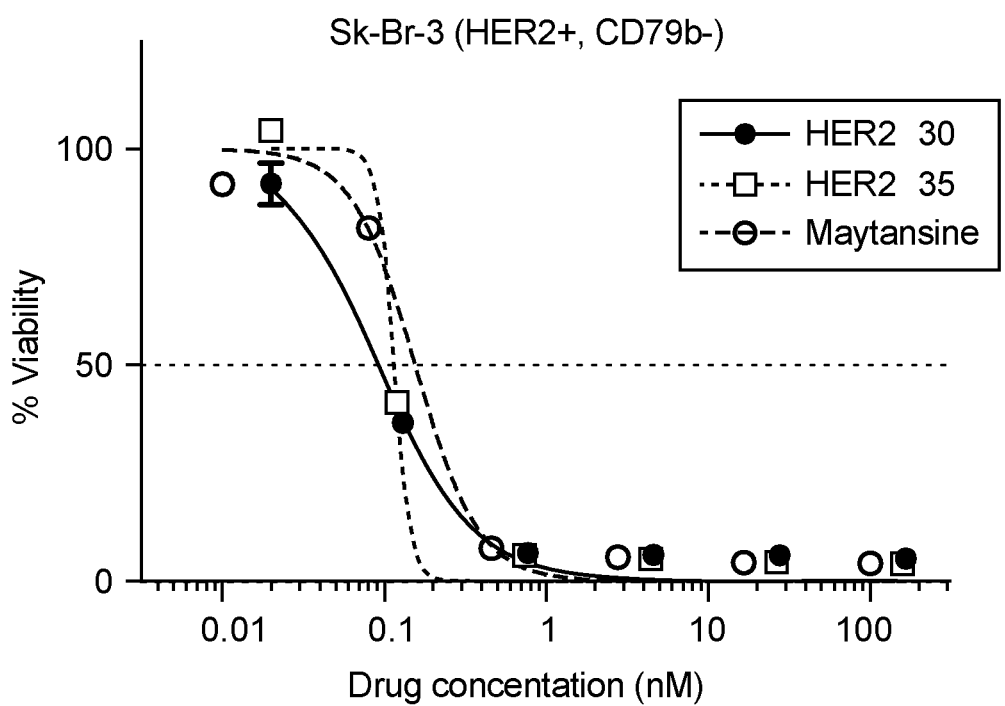
FIG. 15 shows a graph of in vitro potency of maytansine-conjugated ADCs carrying mono-cleavage (35) or galactoside-modified dual-cleavage linkers (30) against Sk-Br-3 cells.
Figure 16:
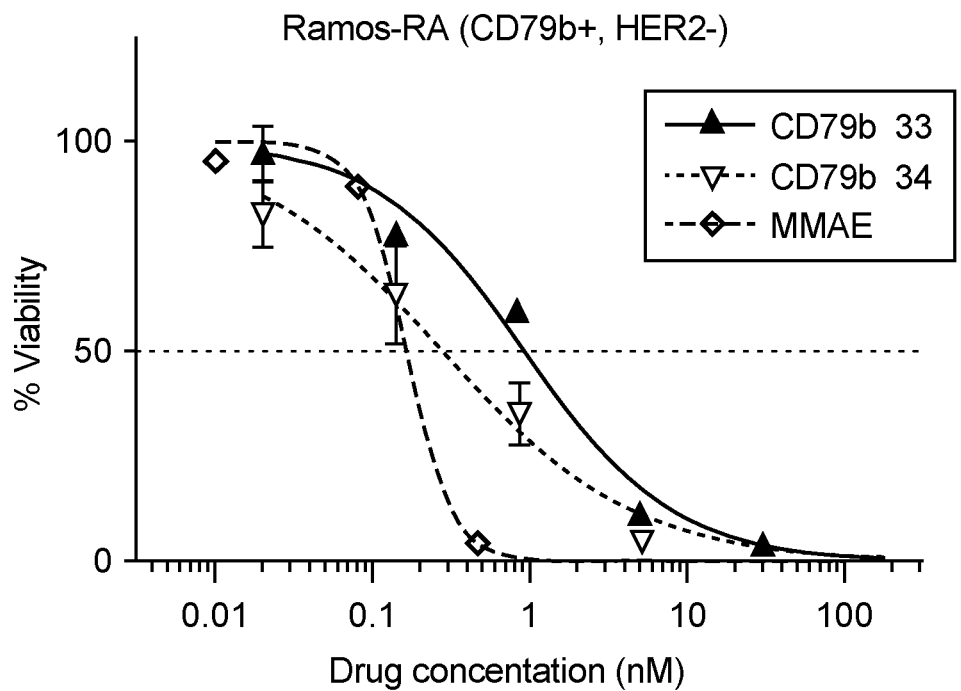
FIG. 16 shows a graph of in vitro potency of MMAE-conjugated ADCs carrying glucuronide-modified dual-cleavage linkers (34) or galactoside-modified dual-cleavage linkers (33) against Ramos-RA cells.
Figure 17:
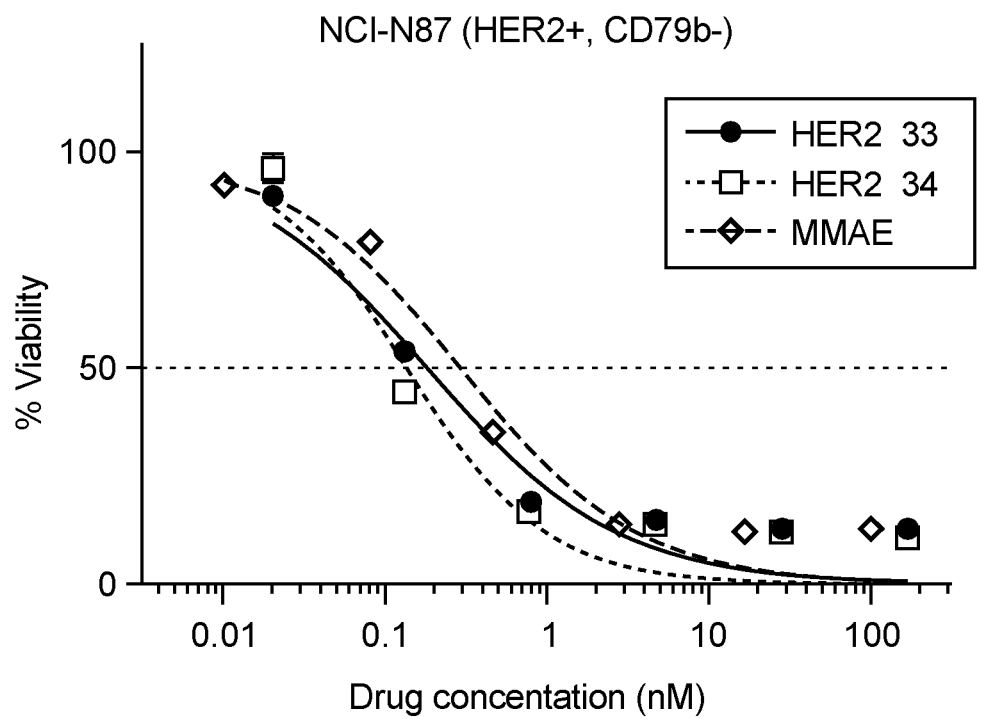
FIG. 17 shows a graph of in vitro potency of MMAE-conjugated ADCs carrying glucuronide-modified dual-cleavage linker (34) or galactoside-modified dual-cleavage linkers (33) against NCI-N87 cells.
Figure 18:
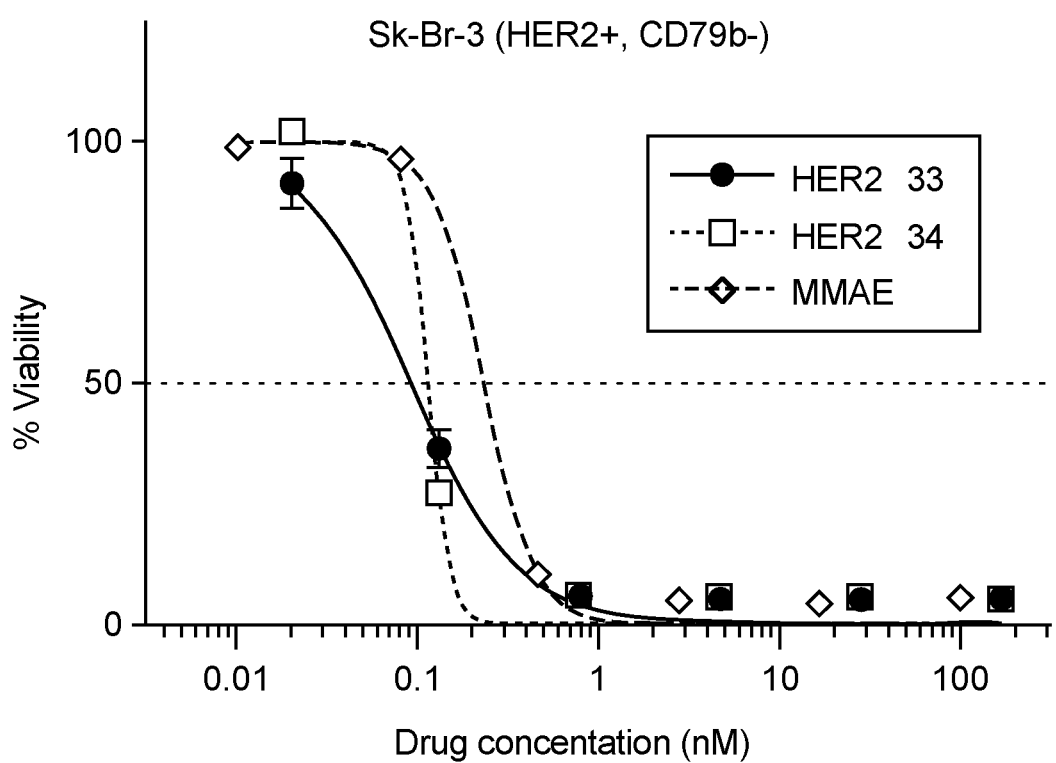
FIG. 18 shows a graph of in vitro potency of MMAE-conjugated ADCs carrying glucuronide-modified dual-cleavage linker (34) or galactoside-modified dual-cleavage linkers (33) against Sk-Br-3 cells.
Figure 19:
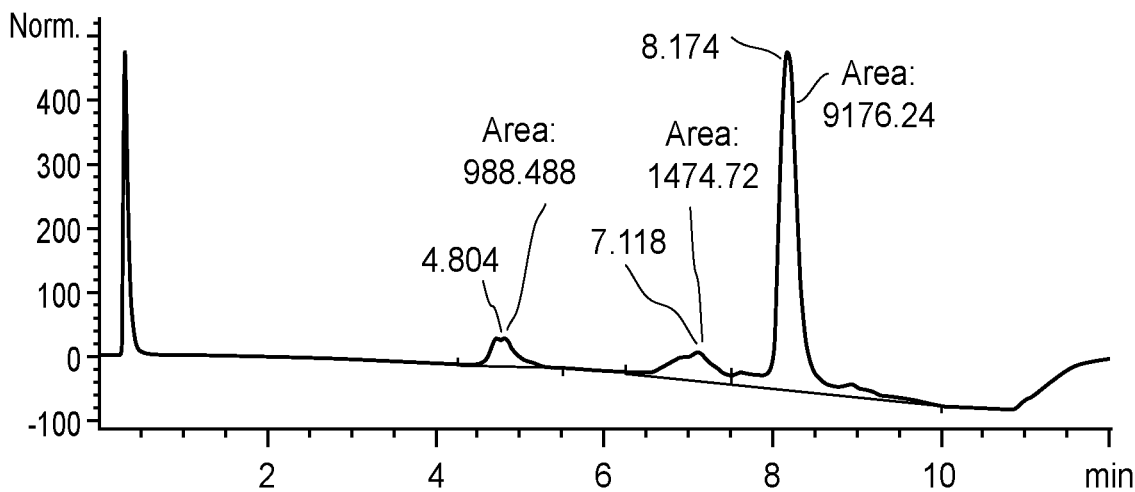
FIG. 19 shows a PLRP trace of construct 46 anti-FITC conjugate, which yielded a DAR of 1.70 as determined by PLRP.
Figure 20:
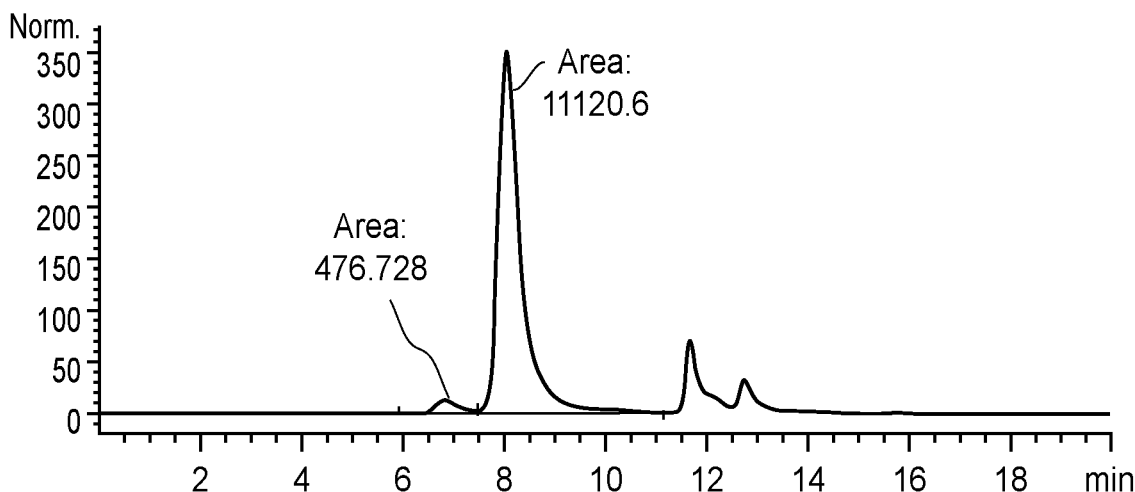
FIG. 20 shows an analytical SEC trace of construct 46 anti-FITC conjugate, which was 95.9% monomeric as determined by analytical SEC.
Figure 21:
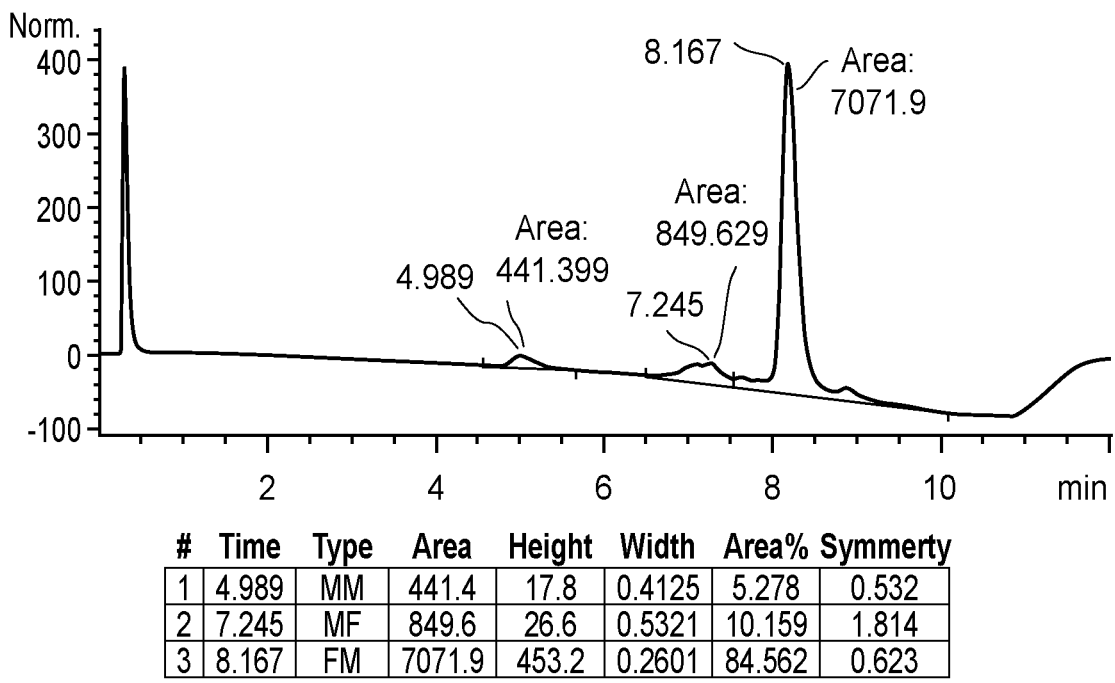
FIG. 21 shows a PLRP trace of construct 46 trastuzumab conjugate, which yielded a DAR of 1.79 as determined by PLRP.
Figure 22:
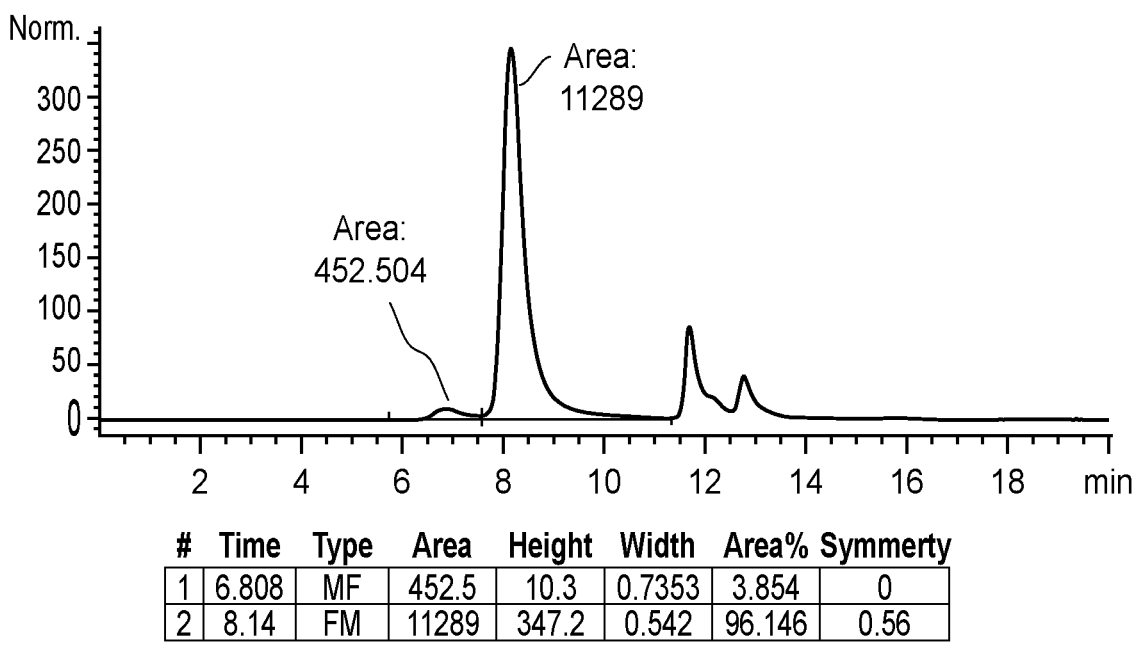
FIG. 22 shows an analytical SEC trace of construct 46 trastuzumab conjugate, which was 96.2% monomeric as determined by analytical SEC.
Figure 23:
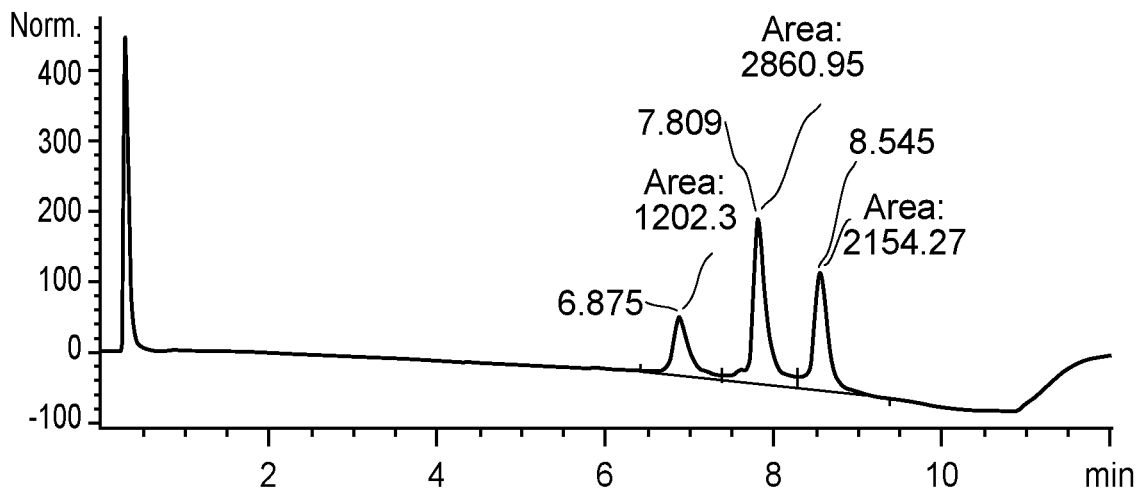
FIG. 23 shows a PLRP trace of construct 46 sacituzumab conjugate, which yielded a DAR of 1.15 as determined by PLRP.
Figure 24:
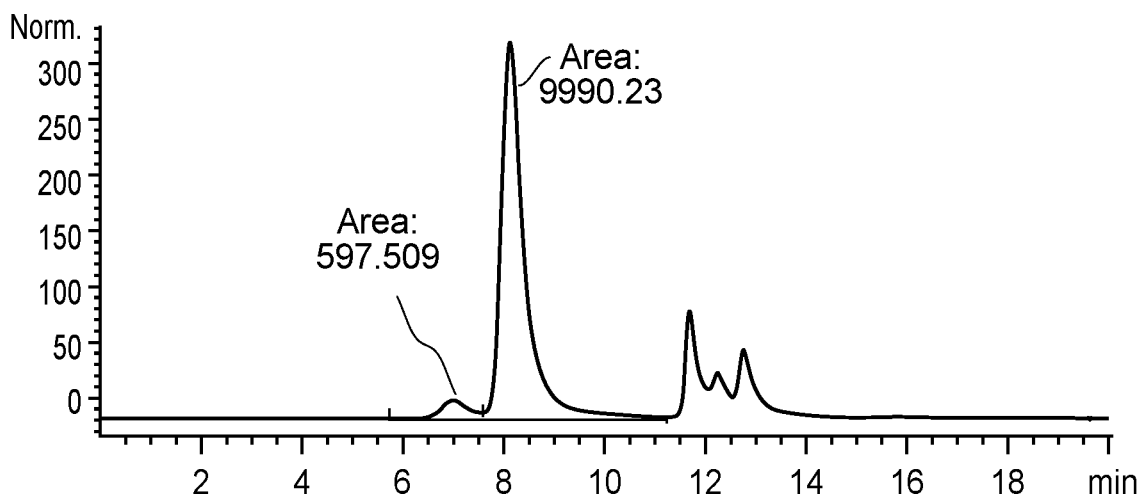
FIG. 24 shows an analytical SEC trace of construct 46 sacituzumab conjugate, which was 94.4% monomeric as determined by analytical SEC.
Figure 25:
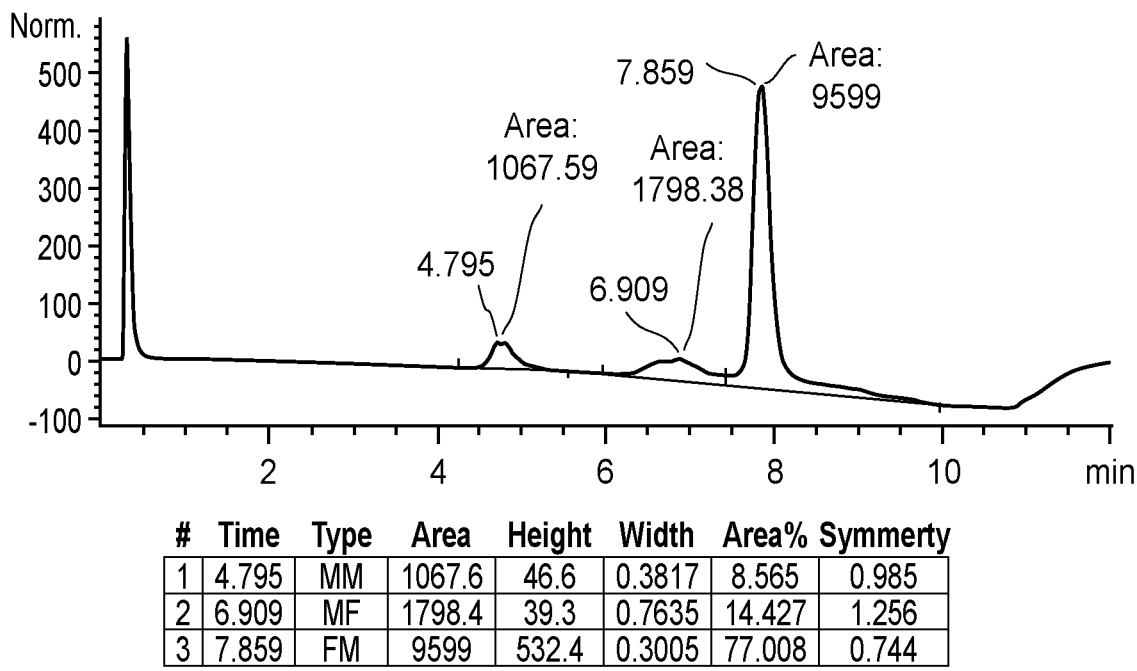
FIG. 25 shows a PLRP trace of construct 44 anti-FITC conjugate, which yielded a DAR of 1.68 as determined by PLRP.
Figure 26:
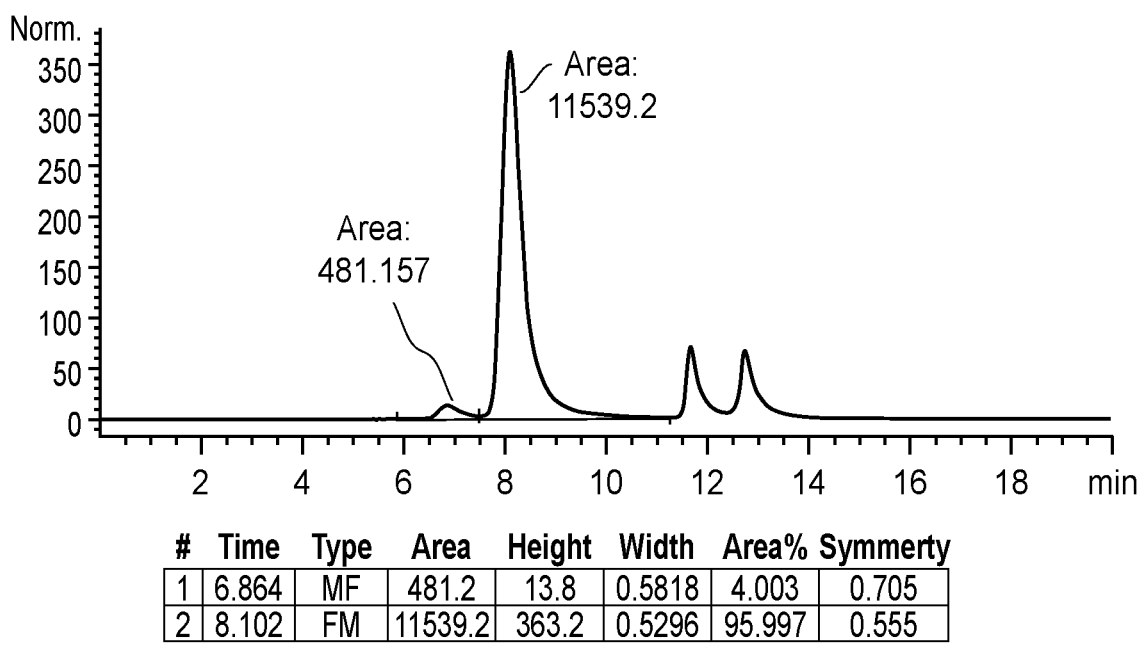
FIG. 26 shows an analytical SEC trace of construct 44 anti-FITC conjugate, which was 96.0% monomeric as determined by analytical SEC.
Figure 27:
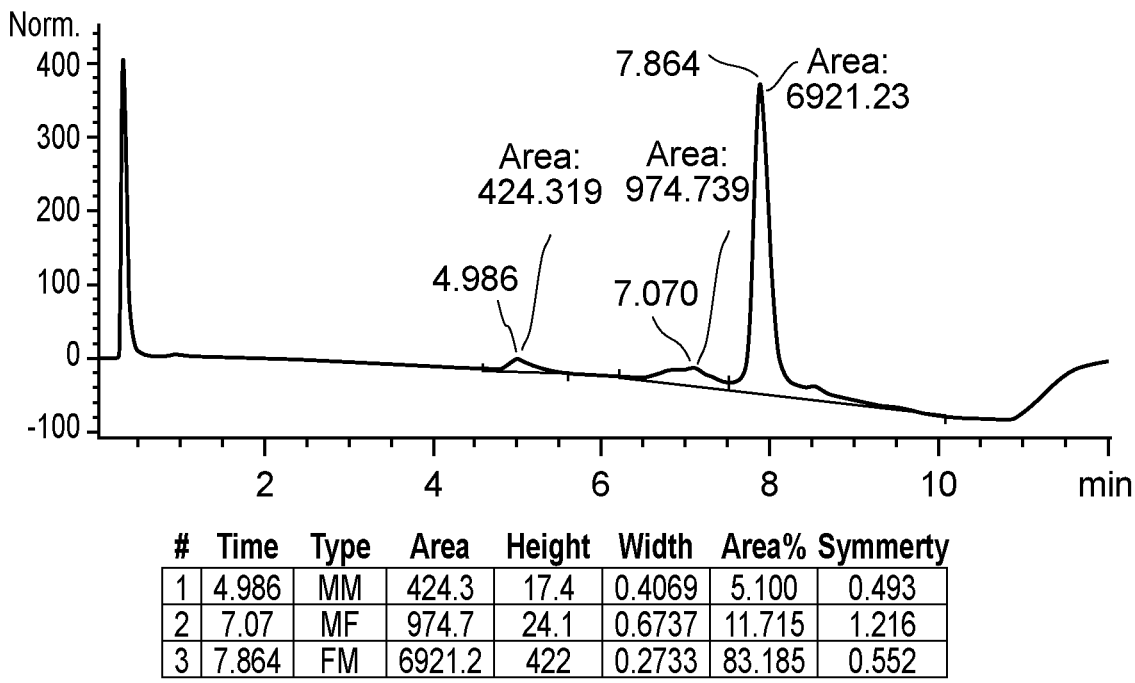
FIG. 27 shows a PLRP trace of construct 44 trastuzumab conjugate, which yielded a DAR of 1.78 as determined by PLRP.
Figure 28:
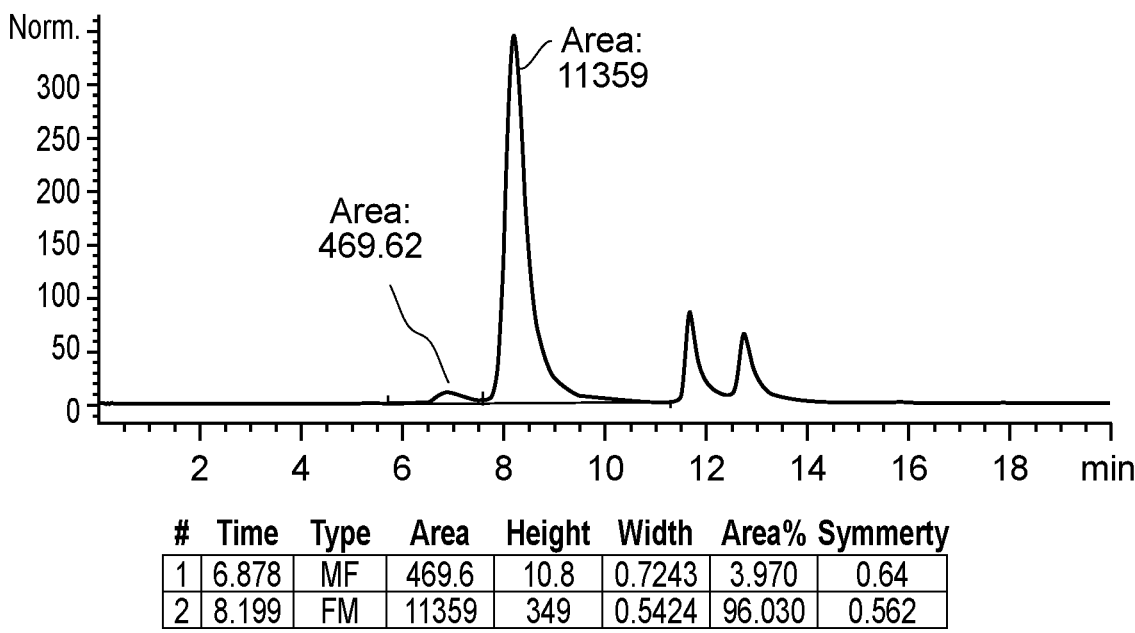
FIG. 28 shows an analytical SEC trace of construct 44 trastuzumab conjugate, which was 96.0% monomeric as determined by analytical SEC.
Figure 29:
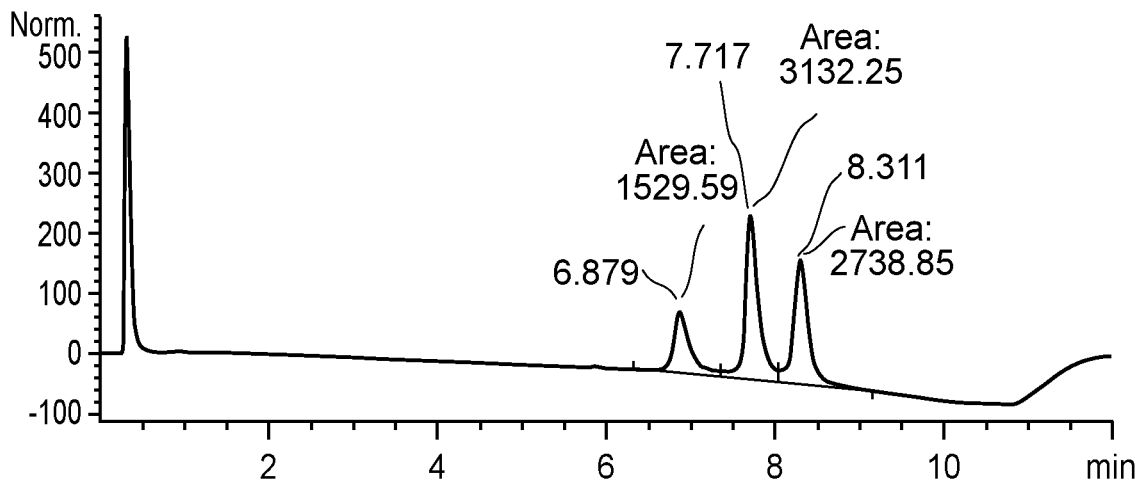
FIG. 29 shows a PLRP trace of construct 44 sacituzumab conjugate, which yielded a DAR of 1.16 as determined by PLRP.
Figure 30:
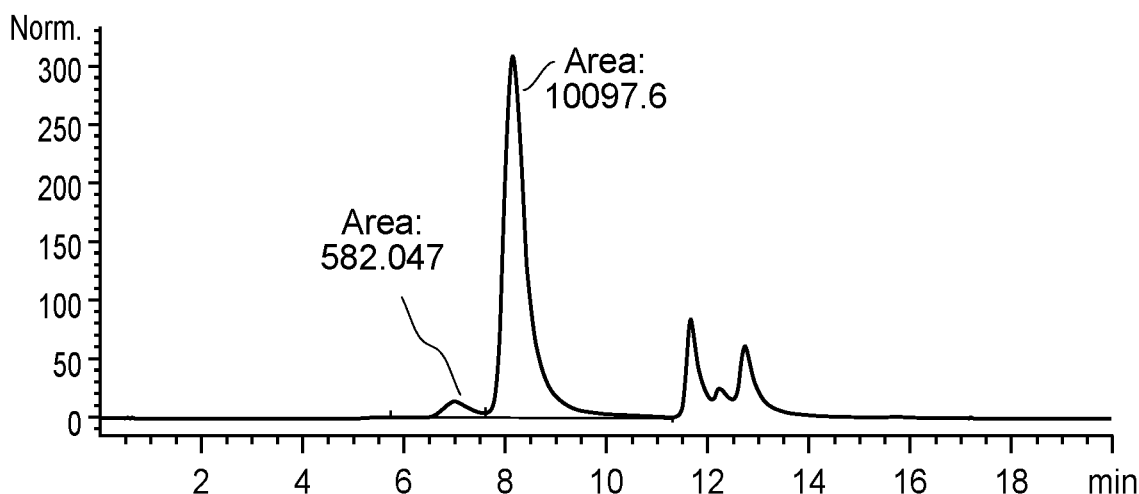
FIG. 30 shows an analytical SEC trace of construct 44 sacituzumab conjugate, which was 94.5% monomeric as determined by analytical SEC.
Figure 31:
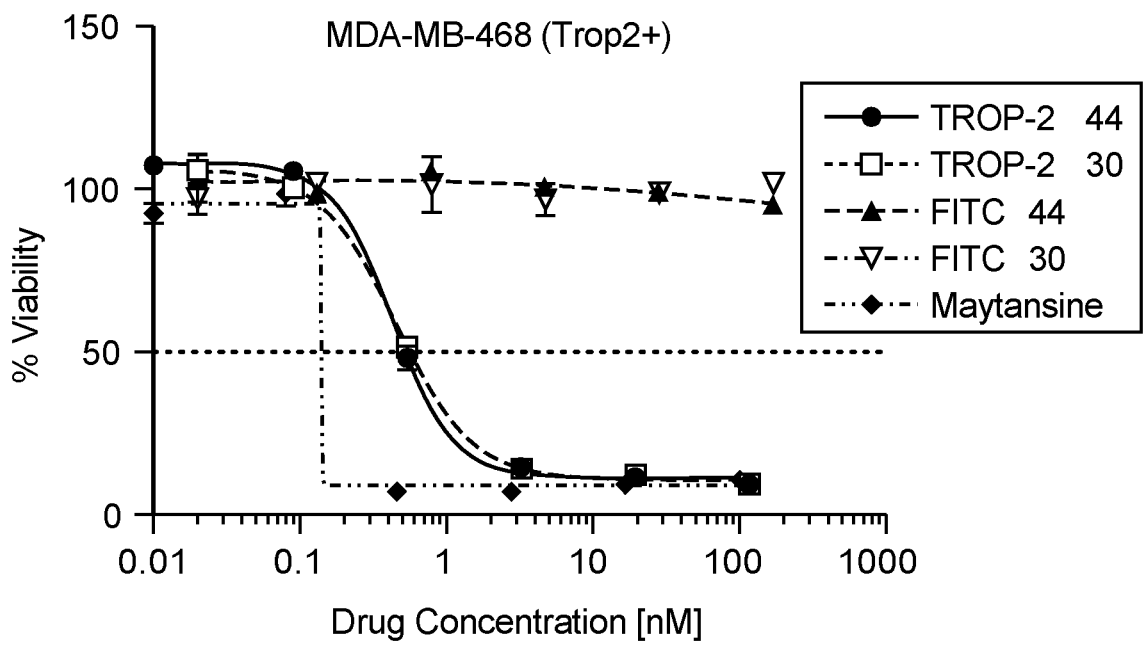
FIG. 31 shows a graph of in vitro potency of maytansine-conjugated ADCs carrying glucoside-modified (44) or galactoside-modified dual-cleavage linkers (30) against MDA-MB-468 cells.
Figure 32:
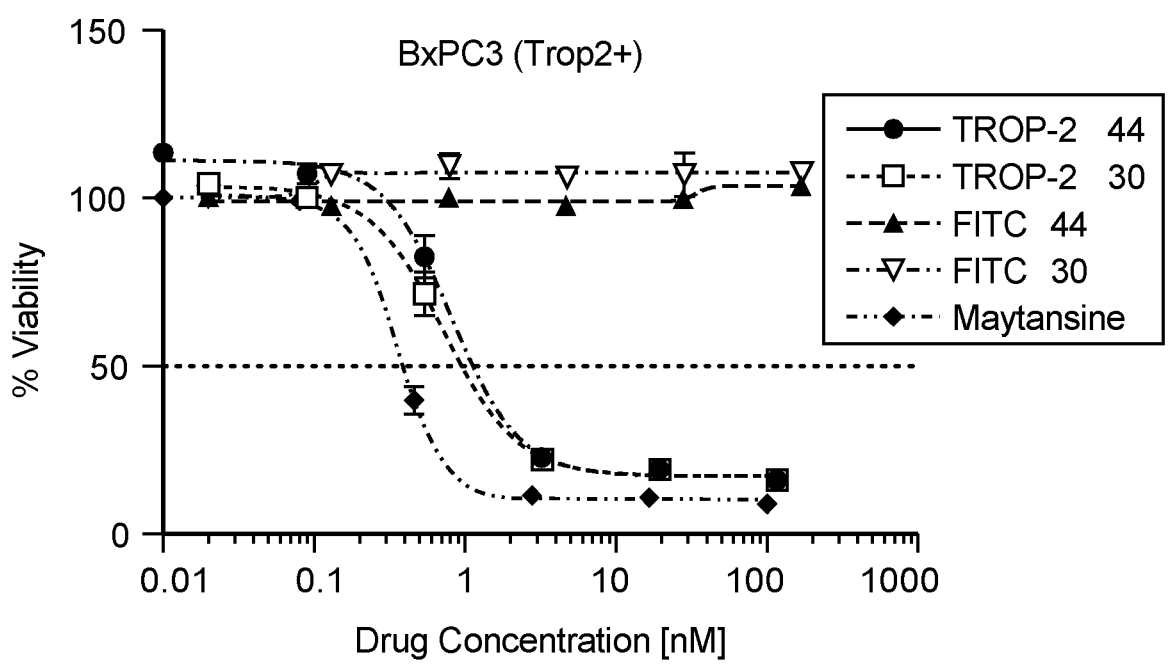
FIG. 32 shows a graph of in vitro potency of maytansine-conjugated ADCs carrying glucoside-modified (44) or galactoside-modified dual-cleavage linkers (30) against BxPC3 cells.
Figure 33:
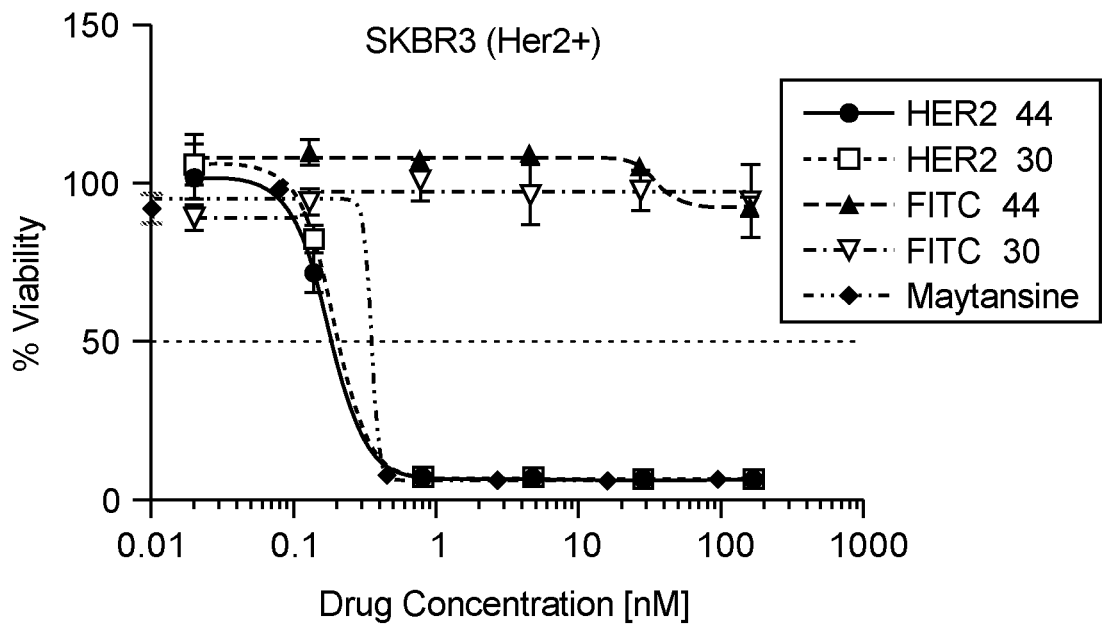
FIG. 33 shows a graph of in vitro potency of maytansine-conjugated ADCs carrying glucoside-modified (44) or galactoside-modified dual-cleavage linkers (30) against SKBR3 cells.
Figure 34:
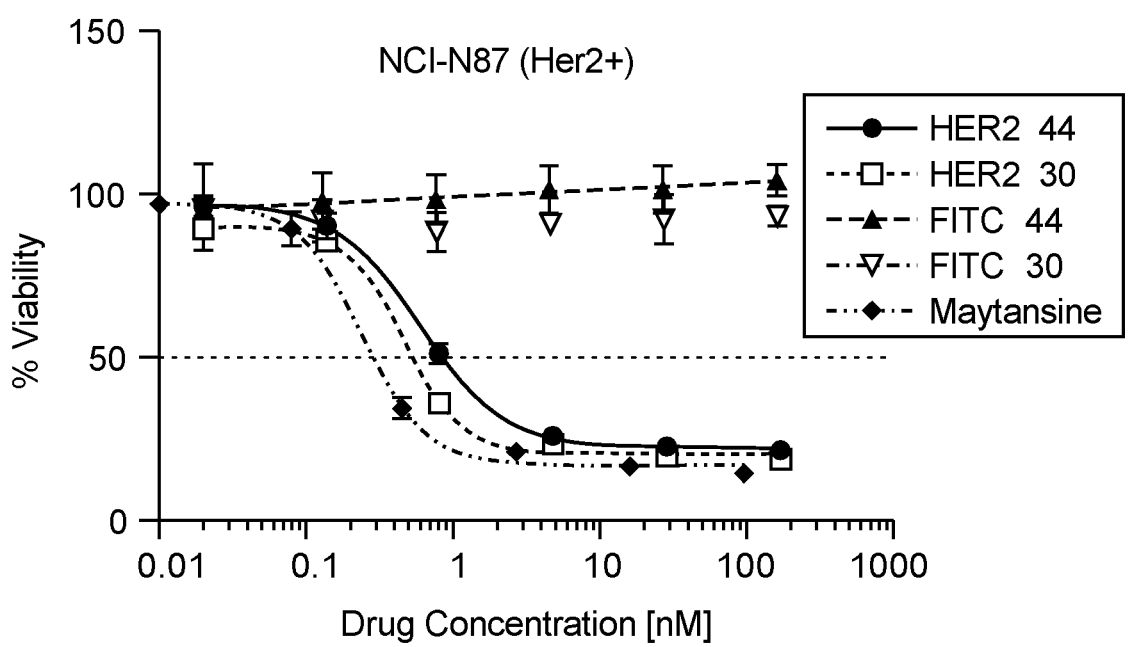
FIG. 34 shows a graph of in vitro potency of maytansine-conjugated ADCs carrying glucoside-modified (44) or galactoside-modified dual-cleavage linkers (30) against NCI-N87 cells.
Figure 35:
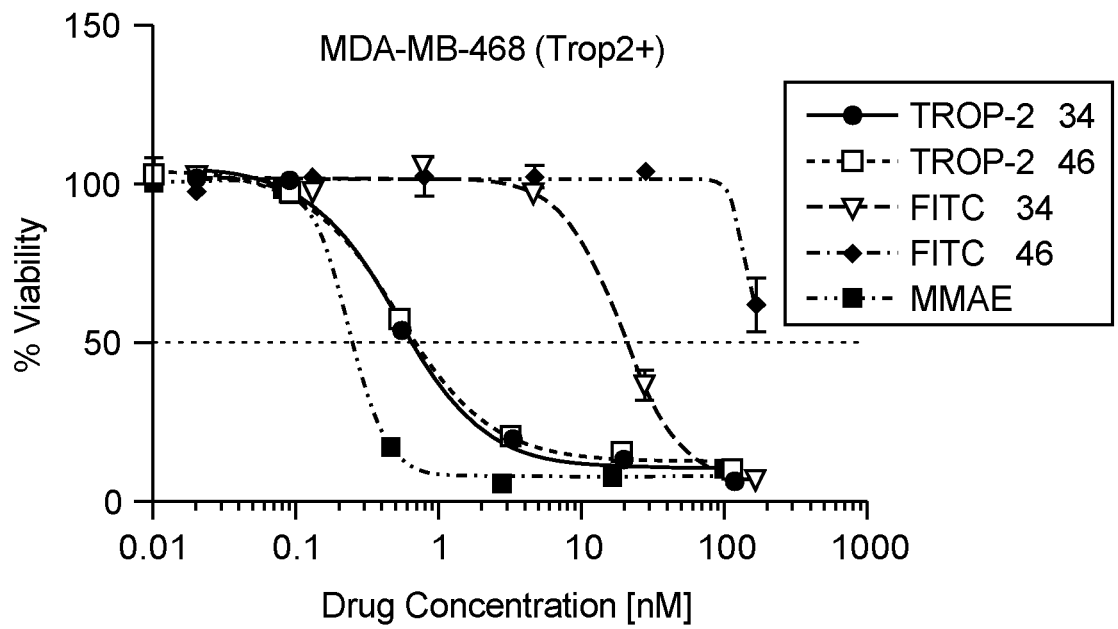
FIG. 35 shows a graph of in vitro potency of MMAE-conjugated ADCs carrying glucuronide-modified (34) or glucoside-modified dual-cleavage linkers (46) against MDA-MB-468 cells.
Figure 36:
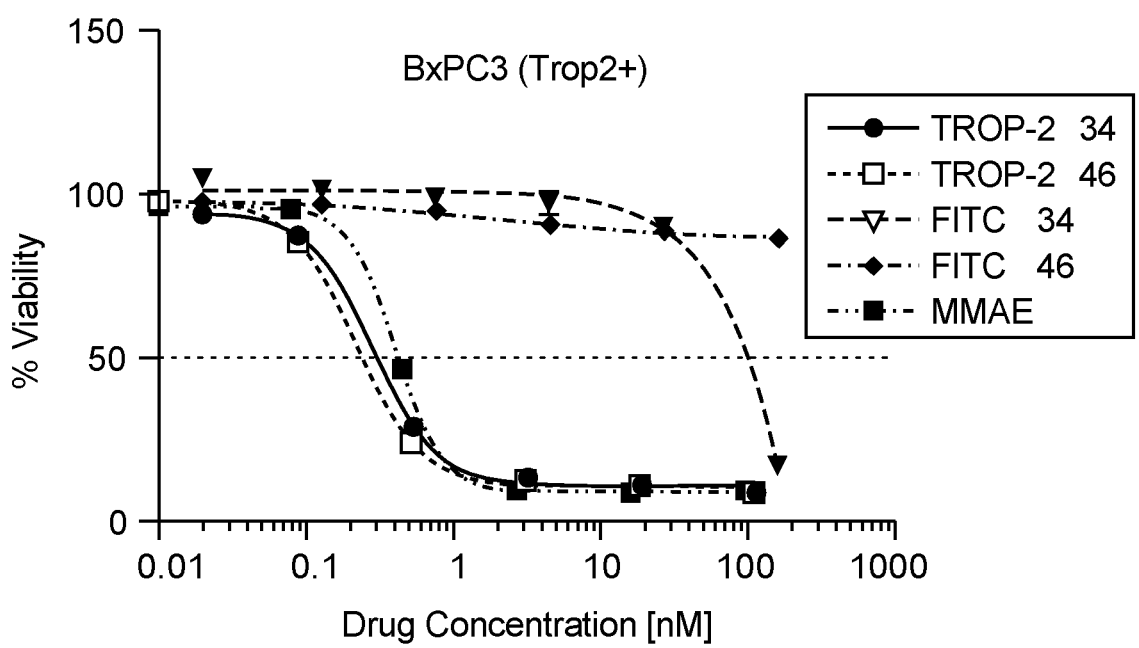
FIG. 36 shows a graph of in vitro potency of MMAE-conjugated ADCs carrying glucuronide-modified (34) or glucoside-modified dual-cleavage linkers (46) against BxPC3 cells.

The in vitro activity of the resulting conjugates was tested using HER2+ (NCI-N87, Sk-Br-3), CD79b+ (Granta-519, Ramos-RA), and TROP-2+ (MDA-MB-468, BxPC3) cancer cell lines. In some studies, the potency of maytansine-conjugated ADCs carrying a galactoside-modified dual-cleavage linker (30) was compared to the activity of the corresponding ADCs generated from the mono-cleavage linker-payload 35 (construct 35 shown in FIG. 11, in vitro potency data shown in FIGS. 12-15). In other studies, the potency of maytansine-conjugated ADCs carrying a galactoside-modified dual-cleavage linker (30) was compared to the activity of the corresponding ADCs generated using a glucoside-modified dual-cleavage linker 44 (in vitro potency data shown in FIGS. 31-34). With respect to the MMAE-conjugated ADCs, the in vitro potency of the galactoside-modified (33) or the glucoside-modified (46) dual-cleavage linkers was compared to that of the glucuronide-modified dual-cleavage linker 34 (construct 34 shown in FIG. 11, in vitro potency data shown in FIGS. 16-18, 35, and 36). Collectively, the results showed that across cell lines representing both solid (gastric, pancreatic, and breast cancers) and hematological tumor indications, ADCs made with the mono- and dual-cleavage linkers-including glucuronide, galactoside, and glucoside variants-provided similar levels of potency. The data suggest that—in spite of the unknowns of glycosidase expression patterns and substrate specificity-removal of the galactoside and glucoside moieties was robust and efficient, and the overall ADC catabolism and payload release was comparable for all linkers tested.

Materials and Methods

General

Synthetic reagents were purchased from Sigma-Aldrich, Acros, AK Scientific, or other commercial sources and were used without purification. Anhydrous solvents were obtained from commercial sources in sealed bottles. Acetobromo-α-D-galactose 21, acetobromo-α-D-glucose 36, MMAE 2, and Maytansine 17 were purchased from commercial sources. HIPS linker compound 32 was obtained commercially from Shanghai Medicilon and used without purification. Pentaflouro-ester 28 was synthesized from 32 using standard literature procedure. Synthesis of compounds 34 and 35 was previously described. In all cases, solvent was removed under reduced pressure with a Buchi Rotovapor R-114 equipped with a Buchi V-700 vacuum pump. Column chromatography was performed with a Biotage Isolera chromatography system. Preparative HPLC purifications were performed using Waters preparative HPLC unit equipped with Phenomenex Kinetex 5 μm EVO C18 150×21.2 mm column. HPLC analyses were conducted on an Agilent 1100 Series Analytical HPLC equipped with a Model G1322A Degasser, Model G1311A Quarternary Pump, Model G1329A Autosampler, Model G1314 Variable Wavelength Detector, Agilent Poroshell 120 SB C18, 4.6 mm×50 mm column at room temperature using a 10-100% gradient of water and acetonitrile containing 0.1% formic acid. HPLCs were monitored at 254 nm.

Synthesis of Constructs 30 and 33

Preparation of (2R,3S,4S,5R,6S)-2-(Acetoxymethyl)-6-(5-formyl-2-nitrophenoxy)tetrahydro-2H-pyran-3,4,5-triyl triacetate (21a)

A 50 mL round-bottom flask was loaded with 204 mg (1.22 mmol) of 3-hydroxy-4-nitrobenzaldehyde 20 and acetobromo-α-D-galalctose 21 (500 mg, 1.22 mmol), followed by 20 mL of anhydrous acetonitrile. The solution was treated with silver(I) oxide (986 mg, 4.3 mmol), and the resulting mixture was vigorously stirred at room temperature in the dark for 24 hours. After concentrating reaction mixture under vacuum, the residue was purified on silica gel using ethyl acetate-hexane mixture as eluent (0-100% gradient) to obtain 420 mg (0.85 mmol, 70% yield) of product as a light yellowish solid. LRMS (ESI): m/z 520.0 [M+Na]$^+$, Calcd for $C_{21}H_{23}NO_{13}$ m/z 520.1.

Preparation of (2R,3S,4S,5R,6S)-2-(Acetoxymethyl)-6-(2-amino-5-(hydroxymethyl)phenoxy)tetrahydro-2H-pyran-3,4,5-triyl triacetate (22)

To a solution of acetate-protected galactoside intermediate 21a (350 mg, 0.70 mmol) in 3 mL of ethyl acetate were added 30 mg of palladium on carbon (10% wt.) and 30 µL of triethylamine. After removal of air, the flask was equipped with hydrogen balloon, and the reaction mixture was stirred at room temperature for 48 hours. After filtration through a pad of celite, solvents were removed under vacuum, the residue was dried under high vacuum to give 300 mg of crude product 22 as white solid, which was used further in synthesis without additional purification. LRMS (ESI): m/z 470.1 [M+H]$^+$, Calcd for $C_{21}H_{27}NO_{11}$ m/z 470.2.

Preparation of (2R,3R,4S,5S,6S)-2-(2-((S)-2-((S)-2-((((9H-Fluoren-9-yl)methoxy)carbonyl)amino)-3-methylbutanamido)propanamido)-5-((((4-nitrophenoxy)carbonyl)oxy)methyl)phenoxy)-6-(acetoxymethyl)tetrahydro-2H-pyran-3,4,5-triyl triacetate (26)

Boc-L-alanine (220 mg, 1.11 mmol) and aniline derivative 22 (520 mg, 1.16 mmol) were combined in 5 mL of anhydrous dichloromethane and 0.50 mL of anhydrous methanol. The resulting solution was treated with EEDQ (280 mg, 1.13 mmol) at room temperature. Reaction mixture was stirred in the dark for one hour, then solvents were removed in vacuum. The resulting crude compound 23 was dried under high vacuum for one hour and dissolved in 6 mL of 1:1 TFA-DCM mixture at room temperature. The solution was allowed to stand for one hour, then solvents were removed, and the resulting crude amine 24 was kept under high vacuum for a few hours.

In a separate 20 mL scintillation vial, Fmoc-L-valine (375 mg, 1.1 mmol) was mixed with HATU (420 mg, 1.1 mmol) and DIPEA (375 µL, 2.15 mmol) in 3 mL of anhydrous DMF. The mixture was stirred at room temperature for 30 minutes, combined with crude compound 24, and stirring continued overnight until reaction was judged complete by LCMS analysis. Reaction mixture was directly purified on reversed-phase C18 column ($CH_3CN$—$H_2O$/0.05% TFA, 0-80% gradient) to give compound 25 as a mixture with minor impurities. Product was thoroughly dried under high vacuum and subjected to the next step without additional purification.

Compound 25 was dissolved in 6 mL of anhydrous DCM and treated with DIPEA (375 µL, 2.15 mmol), followed by 686 mg (2.26 mmol) of bis(4-nitrophenyl) carbonate in one portion at room temperature. The reaction mixture was stirred for one hour, then solvent was removed under vacuum, and the residue was purified by column chromatography on silica gel (EtOAc-hexanes, 10-100% gradient) to yield p-nitrophenyl carbonate product 26 (640 mg, 0.62 mmol, 56% yield over 4 steps) as a yellowish solid. LRMS (ESI): m/z 1049.3 [M+Na]$^+$, Calcd for $C_{51}H_{54}N_4O_{19}$ m/z 1049.3.

Preparation of 4-((((4-((S)-2-((S)-2-Amino-3-methylbutanamido)propanamido)-3-(((2R,3R,4S,5R,6S)-3,4,5-trihydroxy-6-(hydroxymethyl)tetrahydro-2H-pyran-2-yl)oxy)benzyl)oxy)carbonyl)(methyl)amino)butanoic acid (27)

To a 20 mL scintillation vial were added 4-(methylamino)butanoic acid (61 mg, 0.52 mmol), 61 µL (0.35 mmol) of DIPEA, and 1 mL of anhydrous DMF. The resulting solution was combined with 180 mg (0.175 mmol) of PNP-carbonate 26 at room temperature. Reaction mixture was stirred for one hour, until PNP-carbonate was fully consumed as judged by LCMS analysis. Solvents were removed under vacuum, and the residue was dissolved in 3 mL of methanol. The obtained solution was cooled down to 0° C. and treated with 3 mL of 1M aqueous lithium hydroxide. The reaction mixture was stirred for 30 minutes, then warmed up to room temperature and concentrated under vacuum. The residue was directly purified on reversed-phase C18 column ($CH_3CN$—$H_2O$/0.05% TFA, 0-50% gradient) to obtain 90 mg (0.146 mmol, 83% yield over 2 steps) of compound 27 as a yellow oil. LRMS (ESI): m/z 615.3 [M+H]$^+$, Calcd for $C_{27}H_{42}N_4O_{12}$ m/z 615.3.

Preparation of (2S,5S,18R)-1-((4-((((4-(((S)-1-(((1$^4$S,1$^6$S,3$^2$R,3$^3$R,2R,4S,10E,12E,14R)-8$^6$-Chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-1-oxopropan-2-yl)(methyl)amino)-4-oxobutyl)(methyl)carbamoyl)oxy)methyl)-2-(((2R,3R,4S,5R,6S)-3,4,5-trihydroxy-6-(hydroxymethyl)tetrahydro-2H-pyran-2-yl)oxy)phenyl)amino)-18-(3-(2-((1,2-dimethylhydrazinyl)methyl)-1H-pyrrolo[2,3-b]pyridin-1-yl)propanamido)-5-isopropyl-2-methyl-1,4,7,17-tetraoxo-10,13-dioxa-3,6,16-triazanonadecane-19-sulfonic acid (30)

To a 20 mL scintillation vial were added compound 27 (84 mg, 0.14 mmol), 1 mL of anhydrous DMF, and DIPEA (48 µL, 0.28 mmol), followed by 130 mg (0.14 mmol) of pentafluoro ester 28. The resulting mixture was stirred for 30 minutes until coupling was judged complete (LCMS). Maytansine 17 (89 mg, 0.14 mmol) was added directly to the reaction mixture as a solution in 0.5 mL of DMF, followed by addition of HATU (52 mg, 0.14 mmol). After 30 minutes, reaction mixture was purified on reversed-phase C18 column ($CH_3CN$—$H_2O$/0.05% TFA, 10-95% gradient). After complete removal of solvents, the resulting intermediate 29 was dissolved in 3 mL of DMF and treated with 150 µL of piperidine at room temperature. After 30 minutes, reaction mixture was directly purified on reversed-phase preparative HPLC (C18 column, $CH_3CN$—$H_2O$/0.05% TFA, 0-50% gradient). Pure fractions were lyophilized to give 58 mg (0.032 mmol, 23% yield over 3 steps) of compound 30. LRMS (ESI): m/z 1801.8 [M+H]$^+$, Calcd for $C_{82}H_{118}ClN_{13}O_{28}S$ m/z 1800.8.

Preparation of (2R,3S,4S,5R,6S)-2-(Acetoxymethyl)-6-(2-((S)-2-((S)-2-amino-3-methylbutanamido)propanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)tetrahydro-2H-pyran-3,4,5-triyl triacetate (31)

In a 4 mL glass vial were mixed MMAE 2 (13.4 mg of TFA salt, 0.016 mmol), DIPEA (3.8 µL, 0.022 mmol), and 1 mL of anhydrous DMF. The resulting solution was treated with PNP-carbonate 26 (15 mg, 0.015 mmol) and HOAt (1.0 mg, 0.008 mmol). After stirring overnight at room temperature, piperidine (30 µL) was added directly to the reaction mixture. After 30 minutes, reaction mixture was purified on reversed-phase preparative HPLC (C18 column, CH$_3$CN—H$_2$O/0.05% TFA, 0-50% gradient). Pure fractions were lyophilized to obtain 8 mg (0.006 mmol, 40% yield over 2 steps) of compound 31 as an off-white solid. LRMS (ESI): m/z 1383.5 [M+H]$^+$, Calcd for C$_{69}$H$_{106}$N$_8$O$_{21}$ m/z 1383.8.

Preparation of (2S,5S,18R)-1-((4-((5S,8S,11S,12R)-1-((S)-sec-Butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)-2-(((2R,3R,4S,5R,6S)-3,4,5-trihydroxy-6-(hydroxymethyl)tetrahydro-2H-pyran-2-yl)oxy)phenyl)amino)-18-(3-(2-((1,2-dimethylhydrazinyl)methyl)-1H-pyrrolo[2,3-b]pyridin-1-yl)propanamido)-5-isopropyl-2-methyl-1,4,7,17-tetraoxo-10,13-dioxa-3,6,16-triazanonadecane-19-sulfonic acid (33)

In a 4 mL glass vial were combined compound 31 (8 mg, 0.006 mmol), HIPS linker compound 32 (4.5 mg, 0.006 mmol), DIPEA (1.5 µL, 0.009 mmol), and 2.3 mg (0.06 mmol) of HATU in 1 mL DMF. Reaction mixture was stirred for 30 minutes at room temperature, then DMF was removed in vacuum, the residue was dissolved in 1 mL of methanol. To this solution, 1 mL of 1M aqueous lithium hydroxide solution was added, and the resulting mixture was stirred overnight at room temperature. Reaction mixture was directly purified on reversed-phase preparative HPLC (C18 column, CH$_3$CN—H$_2$O/0.05% TFA, 10-60% gradient), pure fractions were lyophilized to give 6 mg (0.0033 mmol, 60% yield over 2 steps) of compound 33 as off-white powder. LRMS (ESI): m/z 1770.9 [M+H]$^+$, Calcd for C$_{84}$H$_{132}$N$_{14}$O$_{25}$S m/z 1769.9.

Synthesis of Constructs 44 and 46

Preparation of (2R,3R,4S,5R,6S)-2-(acetoxymethyl)-6-(2-amino-5-(hydroxymethyl)phenoxy)tetrahydro-2H-pyran-3,4,5-triyl triacetate (37)

To a mixture of compound 20 (5.0 g, 29.9 mmol, 1.7 eq.) and compound 36 (7.23 g, 17.6 mmol, 1 eq.) in anhydrous acetonitrile (100 mL) were added silver(I) oxide (15.6 g, 87.9 mmol, 5 eq.). The mixture was stirred at 25° C. in the dark for 24 hours under nitrogen. Reaction mixture was diluted with EtOAc (100 mL), filtered and concentrated under reduced pressure. The residue was purified by silica gel chromatography (0-30% hexane-EtOAc). To a mixture of intermediate aldehyde (5.61 g, 11.3 mmol) and triethylamine (2.5 mL) in EtOAc (80 mL) were added palladium on carbon (10 wt. %, 800 mg, 0.75 mmol) in one portion. The reaction mixture was stirred at 25° C. for 24 h under H$_2$ atmosphere. The solids were filtered off, and the resulting filtrate was concentrated to give 5.2 g (11.1 mmol, 98% yield) of product 37 as a white solid, which was used into next step without further purification.

Preparation of (2R,3R,4S,5R,6S)-2-(acetoxymethyl)-6-(2-((S)-2-((tert-butoxycarbonyl)amino)propanamido)-5-(hydroxymethyl)phenoxy)tetrahydro-2H-pyran-3,4,5-triyl triacetate (38)

A mixture of compound 37 (5.20 g, 11.1 mmol), Boc-L-Ala-OH (1.75 g, 9.25 mmol) and EEDQ (2.3 g, 9.25 mmol) in anhydrous DCM (40 mL) and MeOH (4 mL) was stirred at room temperature in the dark for 1 h. The reaction mixture was concentrated to give 5.5 g of crude product 38 as a yellow solid. The crude product was used in the next step without further purification.

Preparation of (2R,3R,4S,5R,6S)-2-(acetoxymethyl)-6-(2-((S)-2-aminopropanamido)-5-(hydroxymethyl) phenoxy)tetrahydro-2H-pyran-3,4,5-triyl triacetate (39)

Crude compound 38 (5.5 g, 8.6 mmol) was dissolved in TFA (23 mL). The resulting solution was stirred at room temperature for 10 min and concentrated in vacuum. The residue was purified by reversed-phase chromatography (C18 column, 0-75% acetonitrile-water with 0.05% TFA). Pure fractions were combined and concentrated to give 4.0 g of product amine 39 as a yellow oil (7.5 mmol, 66% yield over 3 steps).

Preparation of (2S,3R,4S,5R,6R)-2-(2-((S)-2-((S)-2-((((9H-fluoren-9-yl)methoxy)carbonyl)amino)-3-methylbutanamido)propanamido)-5-(hydroxymethyl)phenoxy)-6-(acetoxymethyl)tetrahydro-2H-pyran-3,4,5-triyl triacetate (40)

To a mixture of Fmoc-L-valine (3.1 g, 9.2 mmol) and DIPEA (3.9 mL, 22.2 mmol) in anhydrous DMF (20 mL) were added HATU (3.5 g, 9.2 mmol) in one portion at room temperature. The resulting mixture was stirred at room temperature for 30 min and then combined with amine 39 (4.0 g, 7.5 mmol). Reaction mixture was stirred for 16 hours and concentrated in vacuum. The residue was purified by silica gel chromatography (hexane: EtOAc, 0-100%) to give compound 40 (4.5 g, 5.2 mmol, 70% yield) as a white solid.

Preparation of (2S,3R,4S,5R,6R)-2-(2-((S)-2-((S)-2-((((9H-fluoren-9-yl)methoxy)carbonyl)amino)-3-methylbutanamido)propanamido)-5-((((4-nitrophenoxy)carbonyl)oxy)methyl)phenoxy)-6-(acetoxymethyl)tetrahydro-2H-pyran-3,4,5-triyl triacetate (41)

To a mixture of alcohol 40 (4.5 g, 5.2 mmol) and DIPEA (4.5 mL, 26.1 mmol, 5 equiv) in anhydrous THF (20 mL) were added bis(4-nitrophenyl) carbonate (7.9 g, 26.1 mmol, 5 equiv). The resulting mixture was stirred at room temperature for 24 h and concentrated under vacuum. The residue was purified by reversed-phase chromatography (acetonitrile-water 0-70% with 0.05% TFA) to give 4-nitrophenyl carbonate product 41 as a white solid (3.9 g, 73% yield). LRMS (ESI): m/z 1027.3 [M+H]$^+$, Calcd for C$_{51}$H$_{54}$N$_4$O$_{19}$ m/z 1027.3.

Preparation of 4-(((((4-((S)-2-((S)-2-amino-3-methylbutanamido)propanamido)-3-(((2S,3R,4S,5R,6R)-3,4,5-trihydroxy-6-(hydroxymethyl)tetrahydro-2H-pyran-2-yl)oxy)benzyl)oxy)carbonyl)(methyl)amino) butanoic acid (42)

To a mixture of p-nitrophenyl carbonate 41 (380 mg, 0.37 mmol, 1 equiv) and 4-(methylamino)butanoic acid (55 mg, 0.47 mmol, 1.25 equiv) in anhydrous DMF (2 mL) were added DIPEA (190 µL, 1.11 mmol, 3 equiv). The resulting mixture was stirred for 16 h, concentrated under vacuum, and the residue was re-dissolved in THF (2 mL). To the THF solution were added 2 mL of 1M aqueous LiOH at room temperature and stirred for 2 h until hydrolysis was judged complete by HPLC analysis. Reaction mixture was quenched with 1M HCl (2 mL), diluted with DMF (1 mL), and purified by reversed-phase chromatography (C18 column, acetonitrile-water 0-75% MeCN with 0.05% TFA). Pure fractions were collected, concentrated under reduced pressure, and lyophilized to give compound 42 as a white solid (160 mg, 0.26 mmol, 70% yield over two steps). LRMS (ESI): m/z 615.3 [M+H]$^+$, Calcd for $C_{27}H_{42}N_4O_{12}$ m/z 615.3.

Preparation of 4-((((4-((2S,5S,18R)-5-isopropyl-2-methyl-4,7,17,20-tetraoxo-18-(sulfomethyl)-22-(2-((1,2,2-trimethylhydrazineyl)methyl)-1H-pyrrolo[2,3-b]pyridin-1-yl)-10,13-dioxa-3,6,16,19-tetraazadocosanamido)-3-(((2S,3R,4S,5R,6R)-3,4,5-trihydroxy-6-(hydroxymethyl)tetrahydro-2H-pyran-2-yl)oxy)benzyl)oxy)carbonyl)(methyl)amino) butanoic acid (43)

To a solution of compound 32 (97 mg, 0.12 mmol, 1 equiv) in DMF (2 mL) were added HATU (40 mg, 0.1 mmol, 0.85 equiv), followed by DIPEA (63 µL, 0.36 mmol, 3 equiv) at room temperature. The resulting mixture was stirred for 1 h and then combined with 0.1M solution of compound 42 in DMF (1.22 mL, 0.12 mmol, 1 equiv). The reaction mixture was stirred for 30 mins until all the starting materials were consumed as judged by HPLC analysis. The mixture was directly purified by reversed-phase chromatography (C18 column, acetonitrile-water 0-75% MeCN with 0.05% TFA). Pure fractions were collected and lyophilized to give product 43 as a white solid (107 mg, 0.08 mmol, 67% yield). LRMS (ESI): m/z 1391.6 [M+H]$^+$, Calcd for $C_{65}H_{86}N_{10}O_{22}S$ m/z 1391.6.

Preparation of (2S,5S,18R)-1-((4-((((4-(((S)-1-(((14S,16S,32R,33R,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl)oxy)-1-oxopropan-2-yl)(methyl)amino)-4-oxobutyl)(methyl)carbamoyl)oxy)methyl)-2-(((2S,3R,4S,5R,6R)-3,4,5-trihydroxy-6-(hydroxymethyl)tetrahydro-2H-pyran-2-yl)oxy)phenyl)amino)-18-(3-(2-((1,2-dimethylhydrazineyl)methyl)-1H-pyrrolo[2,3-b]pyridin-1-yl)propanamido)-5-isopropyl-2-methyl-1,4,7,17-tetraoxo-10,13-dioxa-3,6,16-triazanonadecane-19-sulfonic acid (44)

To a mixture of compound 43 (35 mg, 25 µmol) and maytansine 17 (16 mg, 25 µmol) in DMF (2 mL) were added HATU (19 mg, 51 µmol, 2 equiv) at room temperature, followed by DIPEA (13 µL, 76 µmol, 3 equiv). The reaction mixture was stirred for 30 min until all starting materials were consumed as judged by HPLC analysis. Piperdine (49 µL, 0.5 mmol, 20 equiv) was then added directly to the solution at room temperature in one shot, and the reaction mixture was stirred for 30 min. The mixture was purified by prep HPLC (C18 column, acetonitrile-water 0-75% MeCN with 0.05% TFA). Pure fractions were combined and lyophilized to give compound 44 as a white solid (21 mg, 12 µmol, 48% yield). LRMS (ESI): m/z 1800.7 [M+H]$^+$, Calcd for $C_{82}H_{118}ClN_{13}O_{28}S$ 1800.8.

Preparation of 4-((S)-2-((S)-2-amino-3-methylbutanamido)propanamido)-3-(((2S,3R,4S,5S,6R)-3,4,5-trihydroxy-6-(hydroxymethyl)tetrahydro-2H-pyran-2-yl)oxy)benzyl ((S)-1-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl) pyrrolidin-1-yl)-3-methoxy-5-methyl-1-oxoheptan-4-yl)(methyl)amino)-3-methyl-1-oxobutan-2-yl) amino)-3-methyl-1-oxobutan-2-yl)(methyl) carbamate (45)

A solution of monomethyl auristatin A 2 (50 mg, 70 µmol) in anhydrous DMF (2 mL) was treated with HOAt (9.5 mg, 70 µmol) and DIPEA (36 µL, 209 µmol) at room temperature. To this mixture, compound 41 (72 mg, 70 µmol, 1 equiv) was added as a solid in one portion at room temperature. Reaction mixture was stirred for 4 hours until all the starting materials were consumed as judged by LCMS analysis. Solvent was removed in vacuum and the residue was re-dissolved in THF (2 mL). The THF solution was treated with aqueous 1M LiOH solation (2 mL) at room temperature and stirred for 2 h until hydrolysis was complete. Reaction mixture was quenched with 1M HCl (2 mL), diluted with DMF (1 mL) and purified by reversed-phase chromatography (C18 column, acetonitrile-water 0-75% MeCN with 0.05% TFA). Pure fractions were combined, concentrated under reduced pressure, and lyophilized to give product 45 as white solid (68 mg, 56 µmol, 80% yield).

Preparation of (2S,5S,18R)-1-((4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)-2-(((2S,3R,4S,5S,6R)-3,4,5-trihydroxy-6-(hydroxymethyl)tetrahydro-2H-pyran-2-yl)oxy)phenyl)amino)-18-(3-(2-((1,2-dimethylhydrazineyl)methyl)-1H-pyrrolo[2,3-b]pyridin-1-yl)propanamido)-5-isopropyl-2-methyl-1,4,7,17-tetraoxo-10,13-dioxa-3,6,16-triazanonadecane-19-sulfonic acid (46)

To a solution of carboxylic acid 32 (50 mg, 63 µmol) in DMF (2 mL) were added HATU (24 mg, 63 µmol), followed by DIPEA (33 µL, 189 µmol) at room temperature. The resulting mixture was stirred for 1 h and combined with compound 45 (68 mg, 63 µmol). Reaction mixture was stirred for 5 hours until all the starting materials were consumed as judged by HPLC analysis. Piperdine (110 µL, 20 equiv) was then added to the solution at room temperature in one shot, and the reaction mixture was stirred for 30 mins, diluted with pH 4.7 0.5M acetate buffer until the solution turned acidic, and purified by prep HPLC (C18 column, acetonitrile-water 0-75% MeCN with 0.05% TFA). Pure fractions were collected and lyophilized to give compound 46 as a white solid (47 mg, 43% yield).). LRMS (ESI): m/z 1769.9 [M+H]$^+$, Calcd for $C_{84}H_{132}N_{14}O_{25}S$ 1769.9.

Example 2

Bioconjugation, Purification and HPLC Analytics Methods

C-terminally aldehyde tagged antibody (15 mg/mL) was conjugated to linker-payloads 30, 33, 44, and 46 at 0.85 mM (8 mol. equivalents drug:antibody) for 72 h at 37° C. in 20 mM sodium citrate, 50 mM NaCl pH 5.5 (20/50 buffer)

containing 0.85% DMA. Free drug was removed using a 30 kD MWCO 0.5 mL Amicon spin concentrator. Samples were added to the spin concentrator, centrifuged at 15,000×g for 7 min, then diluted with 450 µL 20 mM sodium citrate, 50 mM NaCl pH 5.5 and centrifuged again. The process was repeated 10 times. To determine the DAR of the final product, ADCs were examined by analytical HIC (Tosoh #14947) with mobile phase A: 1.5 M ammonium sulfate, 25 mM sodium phosphate pH 7.0, and mobile phase B: 25% isopropanol, 18.75 mM sodium phosphate pH 7.0. To determine aggregation, samples were analyzed using analytical size exclusion chromatography (SEC; Tosoh #08541) with a mobile phase of 300 mM NaCl, 25 mM sodium phosphate pH 6.8.

Results

αHER2 (trastuzumab) and αCD79b (polatuzumab) antibodies modified to contain the aldehyde tag at the heavy chain C-terminus (CT) were conjugated to the Maytansine- and MMAE-bearing linker-payloads, 30 and 33, respectively. These reactions were high yielding, with nearly quantitative conjugation efficiency and >95% total yield. The resulting ADCs had drug-to-antibody ratios (DARs) of 1.79-1.89 and were predominately monomeric. FIGS. 3-10 show representative ADCs with respect to DAR as determined by HIC and monomeric integrity as determined by SEC.

αHER2 (trastuzumab), αTROP-2 (sacituzumab), and anti-FITC antibodies modified to contain the aldehyde tag at the heavy chain C-terminus (CT) were conjugated to the Maytansine- and MMAE-bearing linker-payloads, 44 and 46, respectively. These reactions were generally high yielding. The resulting ADCs had drug-to-antibody ratios (DARs) of 1.15-1.79 and were predominately monomeric. FIGS. 19-30 document representative ADCs with respect to DAR as determined by PLRP and monomeric integrity as determined by SEC.

Example 3

In Vitro Cytotoxicity

Methods

The CD79b-positive B-cell lymphoma cell lines (Granta 519 and Ramos-RA), HER2+ gastric and breast cancer cell lines (NCI-N87 and SKBR3), and TROP-2+ pancreatic and breast cancer cell lines (BxPC3 and MDA-MB-468) were obtained from the DSMZ and ATCC cell banks. The cells were maintained in growth media as recommended by the vendor. 24 h prior to plating, cells were passaged to ensure log-phase growth. On the day of plating, 5000 cells/well were seeded onto 96-well plates in 100 µL normal growth medium. Cells were treated at various concentrations with 20 µL of diluted analytes, and the plates were incubated at 37° C. in an atmosphere of 5% $CO_2$. After 5 d, 100 µL/well of Cell Titer-Glo reagent (Promega) was added, and luminescence was measured using a Molecular Devices SpectraMax M5 plate reader. GraphPad Prism software was used for data analysis.

Results

Galactoside- and glucoside-modified dual-cleavage linkers exhibited potent (sub-nanomolar) in vitro cytotoxicity against antigen-positive cell lines, with activity comparable to that of free payload and of ADCs carrying mono-cleavage linkers or glucuronide-modified dual-cleavage linkers (FIGS. 12-18 and 31-36).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A conjugate comprising:
   an antibody;
   a drug; and
   a cleavable linker that links the antibody to the drug and comprises a first enzymatically cleavable moiety and a second enzymatically cleavable moiety comprising a glycoside selected from the group consisting of a galactoside and a glucoside, and
   wherein the conjugate is of formula (I):

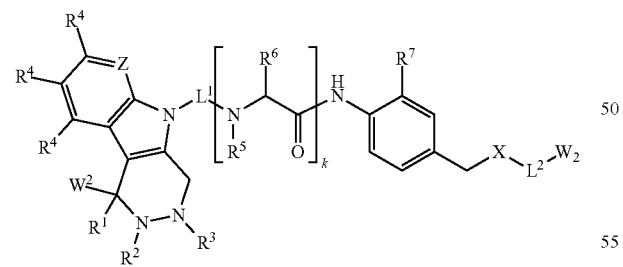

wherein
Z is $CR^4$ or N;
X is O or $NR^4$;
$R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;

each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

each $R^5$ is independently selected from hydrogen, alkyl, substituted alkyl, alkenyl, substituted alkenyl, alkynyl, and substituted alkynyl;

each $R^6$ is independently selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

k is an integer from 1 to 10;
$R^7$ comprises the second enzymatically cleavable moiety;
$L^1$ is a first linker;
$L^2$ is a second linker;
$W^1$ is a maytansine; and
$W^2$ is the antibody.

2. The conjugate of claim 1, wherein:
k is 2; and
the conjugate is of formula (Ia):

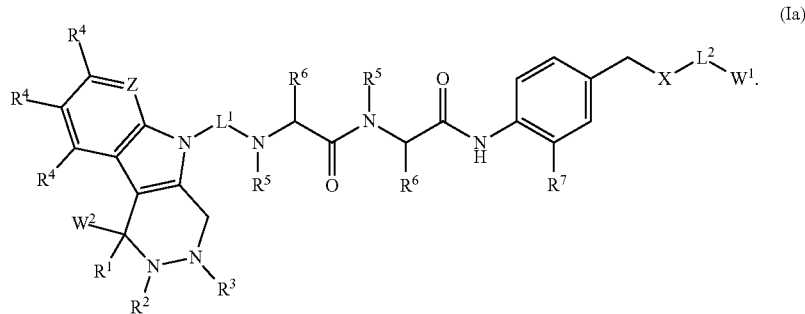
(Ia)

3. The conjugate of claim 1, wherein the second enzymatically cleavable moiety comprises a galactoside.

4. The conjugate of claim 1, wherein the second enzymatically cleavable moiety comprises a glucoside.

5. The conjugate of claim 2, wherein the conjugate is of formula (Ib):

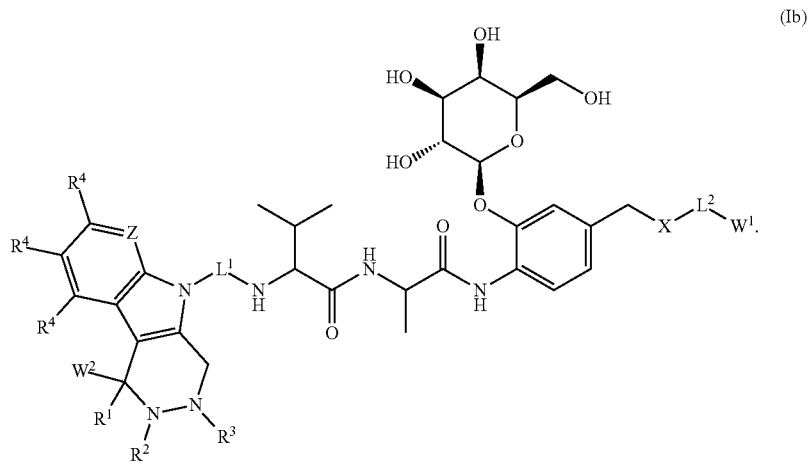
(Ib)

6. The conjugate of claim 2, wherein the conjugate is of formula (Ic):

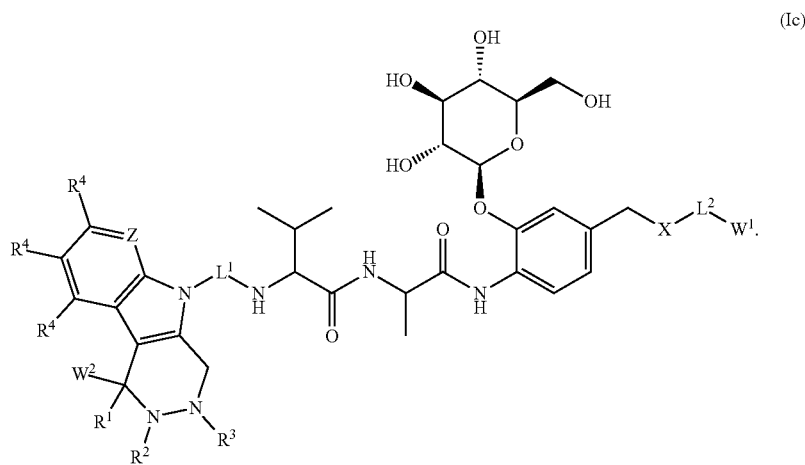
(Ic)

7. The conjugate of claim 1, wherein $L^1$ comprises:

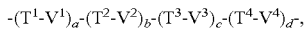

wherein
a, b, c and d are each independently 0 or 1;
$T^1$, $T^2$, $T^3$ and $T^4$ are each independently selected from a covalent bond, $(C_1$-$C_{12})$alkyl, substituted $(C_1$-$C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)$ p, —$(CR^{13}OH)_m$—, 4-amino-piperidine (4AP), an acetal group, a hydrazine, a disulfide, and an ester, wherein EDA is an ethylene diamine moiety, PEG is a polyethylene glycol, and AA is an amino acid residue or an amino acid analog, wherein each w is an integer from 1 to 20, each n is an integer from 1 to 30, each p is an integer from 1 to 20, and each m is an integer from 1 to 12;
$V^1$, $V^2$, $V^3$ and $V^4$ are each independently selected from the group consisting of a covalent bond, —CO—, —$NR^{15}$—, —$NR^{15}$ $(CH_2)_q$—, —$NR^{15}$ $(C_6H_4)$—, —$CONR^{15}$—, —$NR^{15}CO$—, —C(O)O—, —OC(O)—, —O—, —S—, —S(O)—, —$SO_2$—, —$SO_2NR^{15}$—, —$NR^{15}SO_2$— and —P(O)OH—, wherein each q is an integer from 1 to 6;
each $R^{13}$ is independently selected from hydrogen, an alkyl, a substituted alkyl, an aryl, and a substituted aryl; and
each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

8. The conjugate of claim 1, wherein $L^2$ comprises:

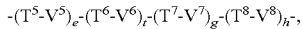

wherein
e, f, g and h are each independently 0 or 1;
$T^5$, $T^6$, $T^7$ and $T^8$ are each independently selected from a covalent bond, $(C_1$-$C_{12})$alkyl, substituted $(C_1$-$C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, —$(CR^{13}OH)_m$—, 4-amino-piperidine (4AP), an acetal group, a hydrazine, a disulfide, and an ester, wherein EDA is an ethylene diamine moiety, PEG is a polyethylene glycol, and AA is an amino acid residue or an amino acid analog, wherein each w is an integer from 1 to 20, each n is an integer from 1 to 30, each p is an integer from 1 to 20, and each m is an integer from 1 to 12;
$V^5$, $V^6$, $V^7$ and $V^8$ are each independently selected from the group consisting of a covalent bond, —CO—, —$NR^{15}$—, —$NR^{15}$ $(CH_2)_q$—, —$NR^{15}$ $(C_6H_4)$—, —$CONR^{15}$—, —$NR^{15}CO$—, —C(O)—, —OC(O)—, —O—, —S—, —S(O)—, —$SO_2$—, —$SO_2NR^{15}$—, —$NR^{15}SO_2$— and —P(O)OH—, wherein each q is an integer from 1 to 6;
each $R^{13}$ is independently selected from hydrogen, an alkyl, a substituted alkyl, an aryl, and a substituted aryl; and
each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

9. The conjugate of claim 7, wherein:
$T^1$ is selected from a $(C_1$-$C_{12})$alkyl and a substituted $(C_1$-$C_{12})$alkyl;
$T^2$, $T^3$, and $T^4$ are each independently selected from aryl, substituted aryl, heteroaryl, substituted heteroaryl, cycloalkyl, substituted cycloalkyl, heterocyclyl, and substituted heterocyclyl, $(EDA)_w$, $(PEG)_n$, $(C_1$-$C_{12})$alkyl, substituted $(C_1$-$C_{12})$alkyl, $(AA)_p$, —$(CR^{13}OH)_m$—, 4-amino-piperidine (4AP), an acetal group, a hydrazine, and an ester; and
$V^1$, $V^2$, $V^3$ and $V^4$ are each independently selected from the group consisting of a covalent bond, —CO—, —$NR^{15}$—, —$NR^{15}$ $(CH_2)_q$—, —$NR^{15}$ $(C_6H_4)$—, —$CONR^{15}$—, —$NR^{15}CO$—, —C(O)O—, —OC(O)—, —O—, —S—, —S(O)—, —$SO_2$—, —$SO_2NR^{15}$—, —$NR^{15}SO_2$—, and —P(O)OH—;
wherein:
$(PEG)_n$ is

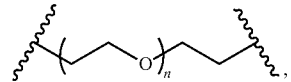

where n is an integer from 1 to 30;
EDA is an ethylene diamine moiety having the following structure:

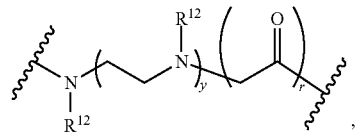

where y is an integer from 1 to 6 and r is 0 or 1;
4-amino-piperidine (4AP) is

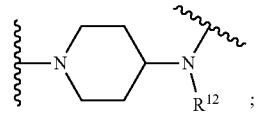

each $R^{12}$ and $R^{15}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring; and
$R^{13}$ is selected from hydrogen, an alkyl, a substituted alkyl, an aryl, and a substituted aryl.

10. The conjugate of claim 7, wherein:
$T^1$ is $(C_1$-$C_{12})$alkyl and $V^1$ is —CO—;
$T^2$ is an amino acid analog and $V^2$ is —NH—;
$T^3$ is (PEG) n and $V^3$ is —CO—; and
d is 0.

11. The conjugate of claim 8, wherein:
$T^5$ is a covalent bond and $V^5$ is —CO—; and
f, g and h are 0.

12. The conjugate of claim 8, wherein:
$T^5$ is a covalent bond and $V^5$ is —$CONR^{15}$—;
$T^6$ is $(C_1$-$C_{12})$alkyl and $V^6$ is —CO—; and
g and h are 0.

13. A pharmaceutical composition comprising:
   a conjugate gate of claim 1; and
   a pharmaceutically-acceptable excipient.

14. A method of administering a conjugate to a subject, the method comprising:
   administering to a subject a conjugate of claim 1.

15. A method of treating cancer in a subject, the method comprising:
   administering to a subject a therapeutically effective amount of a pharmaceutical composition comprising a conjugate of claim 1, wherein the administering is effective to treat cancer in the subject.

* * * * *